US010668049B2

(12) United States Patent
Kaufer et al.

(10) Patent No.: US 10,668,049 B2
(45) Date of Patent: Jun. 2, 2020

(54) METHODS OF TREATING COGNITIVE DECLINE WITH TRANSFORMING GROWTH FACTOR BETA INHIBITORS

(71) Applicants: The Regents of the University of California, Oakland, CA (US); Ben-Gurion University of the Negev, Beer-Sheva (IL)

(72) Inventors: Daniela Kaufer, Oakland, CA (US); Alon Friedman, Gedera (IL); Luisa Cacheaux, Berkeley, CA (US)

(73) Assignees: The Regents of the University of California, Oakland, CA (US); Ben-Gurion University of the Negev, Beer-Sheva (IL)

( * ) Notice: Subject to any disclaimer, the term of this patent is extended or adjusted under 35 U.S.C. 154(b) by 0 days.

(21) Appl. No.: 15/258,862

(22) Filed: Sep. 7, 2016

(65) Prior Publication Data
US 2016/0367530 A1 Dec. 22, 2016

Related U.S. Application Data

(62) Division of application No. 13/132,290, filed as application No. PCT/US2009/066856 on Dec. 4, 2009, now Pat. No. 9,468,649.

(60) Provisional application No. 61/120,218, filed on Dec. 5, 2008.

(51) Int. Cl.
*A61K 31/4178* (2006.01)
*A61K 31/00* (2006.01)
*A61K 31/70* (2006.01)
*A61K 9/00* (2006.01)
*A61K 31/4439* (2006.01)
*A61K 45/06* (2006.01)
*C07K 16/28* (2006.01)
*C12N 15/113* (2010.01)

(52) U.S. Cl.
CPC ........ *A61K 31/4178* (2013.01); *A61K 9/0019* (2013.01); *A61K 9/0053* (2013.01); *A61K 9/0085* (2013.01); *A61K 31/00* (2013.01); *A61K 31/4439* (2013.01); *A61K 31/70* (2013.01); *A61K 45/06* (2013.01); *C07K 16/2863* (2013.01); *C12N 15/1136* (2013.01); *C07K 2317/76* (2013.01)

(58) Field of Classification Search
CPC ...... A61K 45/06; A61K 9/0019; A61K 31/70; A61K 9/0053; A61K 9/0085; A61K 31/4439; A61K 31/4178; A61K 31/00; C07K 2317/76; C07K 16/2803; C12N 15/113
See application file for complete search history.

(56) References Cited

U.S. PATENT DOCUMENTS

| 6,319,955 | B1 | 11/2001 | Alessandrini et al. |
|---|---|---|---|
| 2005/0227936 | A1 | 10/2005 | McSwiggen et al. |
| 2007/0202551 | A1 | 8/2007 | Gudkov et al. |
| 2007/0212738 | A1 | 9/2007 | Haley et al. |
| 2008/0081791 | A1 | 4/2008 | Huang et al. |

FOREIGN PATENT DOCUMENTS

| EP | 1947116 | 7/2008 |
|---|---|---|
| WO | WO 2003/037368 | 5/2003 |
| WO | WO 2008/006583 | 1/2008 |
| WO | WO 2008/066626 | 6/2008 |

OTHER PUBLICATIONS

Hampel et al. The future of Alzheimer's disease: the next 10 years. Prog Neurobiol. Dec. 2011;95(4):718-28. Epub Nov. 22, 2011.*
Bar-Klein, et al.; "Losartan Prevents Acquired Epilepsy via TGF-b Signaling Suppression"; Annals of Neurology; vol. 75, No. 6, pp. 864-875 (2014).
Friedman, et al.; "Should losartan be administered following brain injury?"; Expert Rev. Neurother.; vol. 14, No. 12, pp. 1365-1375 (2014).
GeneCards, "Mitogen-Activated Protein Kinase Kinase", Feb. 23, 2010, http://www.genecards.org/cgi-bin/carddisp.pl?gene=MAP2K1&search=mek1.
Ivens, et al., "TGF-b Receptor-Mediated Albumin Uptake into Astrocytes is Involved in Neocortical Epileptogenesis", Brain, 2007, 130:535-547.
Korpal et al. Targeting the transforming growth factor-beta signalling pathway in metastatic cancer. Eur J Cancer. May 2010; 46(7):1232-40. Epub Mar. 20, 2010.
Perrin et al. Multi modal techniques for diagnosis and prognosis of Alzheimer's disease. Nature Oct. 15, 2009; 461(7266):916-22, Published online Oct. 14, 2009.
Ranaivoa, et al., "Albumin Activates Astrocytes and Microglia Through Mitogen-Activated Protein Kinase Pathways", Brain Research, 2009, 1313:222-231.
Vickers. A vaccine against Alzheimer's disease: developments to date. Drugs Aging 2002; 19(7):487-94.
Weissberg, et al.; "Albumin induces excitatory synaptogenesis through astrocytic TGF-β/ALK5 signaling in a model of acquired epilepsy following blood-brain barrier dysfunction"; Neurobiology of Disease; vol. 78, pp. 115-125 (2015).
Xie, et al., "Regulation of TGF-beta 1-induced Connective Tissue Growth Factor Expression in Airway Smooth Muscle Cells", Am J Physiol Lung Cell Mol Physiol, 2005, 288:L68-L76.
Byfield, et al.; "SB-505124 Is a Selective Inhibitor of Transforming Growth Factor-β Type I Receptors ALK4, ALK5, and ALK7"; Molecular Pharmacology; vol. 65, No. 3, pp. 744-752 (2004).

(Continued)

*Primary Examiner* — Gregory S Emch
(74) *Attorney, Agent, or Firm* — Bozocevic Field & Francis, LLP; Paula A. Borden

(57) ABSTRACT

The present invention provides methods of treating epilepsy and other neurological disorders. The methods generally involve administering to an individual in need thereof an effective amount of an agent that blocks a transforming growth factor-beta pathway.

16 Claims, 22 Drawing Sheets

Specification includes a Sequence Listing.

(56) References Cited

OTHER PUBLICATIONS

Clausi, et al.; "Delayed ALK5 inhibition improves functional recovery in neonatal brain injury"; Journal of Cerebral Blood Flow & Metabolism; vol. 37, No. 3, pp. 787-800 (2017).

Manaenko, et al.; "Inhibition of TGF-β Attenuates Brain Injury and Neurological Deficits in a Rat Model of GMH"; Stroke; vol. 45, No. 3, pp. 828-834 (Mar. 2014).

Uhl, et al.; "SD-208, a Novel Transforming Growth Factor β Receptor I Kinase Inhibitor, Inhibits Growth and Invasiveness and Enhances Immunogenicity of Murine and Human Glioma Cells In vitro and In vivo"; Cancer Research; vol. 64, pp. 7954-7961 (Nov. 1, 2004).

Boyle, P.A., Wilson, R.S., Yu, L., Barr, A.M., Honer, W.G., Schneider, J.A., and Bennett, D.A. (2013). Much of late life cognitive decline is not due to common neurodegenerative pathologies. Ann. Neurol. 74, 478-489.

Ghezzi, L., Scarpini, E., and Galimberti, D. (2013). Disease-modifying drugs in Alzheimer's disease. Drug Des. Devel. Ther. 7, 1471-1479.

Herrup, K. (2015). The case for rejecting the amyloid cascade hypothesis. Nat. Neurosci. 18, 794-799.

Hung, S.-Y., and Fu, W.-M. (2017). Drug candidates in clinical trials for Alzheimer's disease. J. Biomed. Sci. 24, 47.

Jack, C.R., Wiste, H.J., Weigand, S.D., Rocca, W.A., Knopman, D.S., Mielke, M.M., Lowe, V.J., Senjem, M.L., Gunter, J.L., Preboske, G.M., et al. (2014). Age-specific population frequencies of cerebral β-amyloidosis and neurodegeneration among people with normal cognitive function aged 50-89 years: a cross-sectional study. Lancet Neurol. 13, 997-1005.

Jack, C.R., Therneau, T.M., Wiste, H.J., Weigand, S.D., Knopman, D.S., Lowe, V.J., Mielke, M.M., Vemuri, P., Roberts, R.O., Machulda, M.M., et al. (2016). Transition rates between amyloid and neurodegeneration biomarker states and to dementia: a population-based, longitudinal cohort study. Lancet Neurol. 15, 56-64.

Mostafavi, S., Gaiteri, C., Sullivan, S.E., White, C.C., Tasaki, S., Xu, J., Taga, M., Klein, H.-U., Patrick, E., Komashko, V., et al. (2018). A molecular network of the aging human brain provides insights into the pathology and cognitive decline of Alzheimer's disease. Nat. Neurosci. 21, 811-819.

Onos, K.D., Sukoff Rizzo, S.J., Howell, G.R., and Sasner, M. (2016). Toward more predictive genetic mouse models of Alzheimer's disease. Brain Res. Bull. 122, 1-11.

Puzzo, D., Lee, L., Palmeri, A., Calabrese, G., and Arancio, O. (2014). Behavioral assays with mouse models of Alzheimer's disease: practical considerations and guidelines. Biochem. Pharmacol. 88, 450-467.

Wyss-Coray, T., Lin, C., Yan, F., Yu, G.-Q., Rohde, M., McConlogue, L., Masliah, E., and Mucke, L. (2001). TGF-beta1 promotes microglial amyloid-beta clearance and reduces plaque burden in transgenic mice. Nat. Med. 7, 612-618.

\* cited by examiner evoked activity
aCSF aCSF + TGF-ß1

Spontaneous activity aSERUM aCSF + Albumin

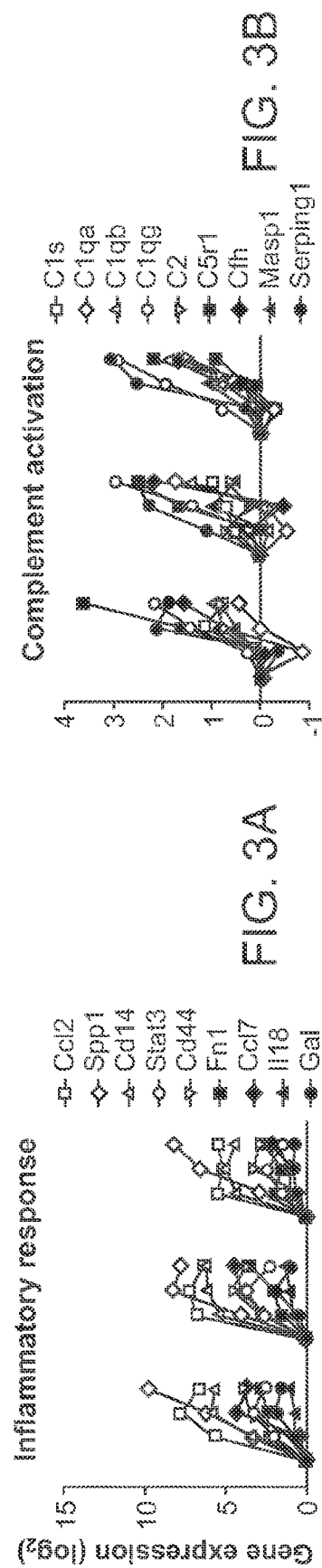
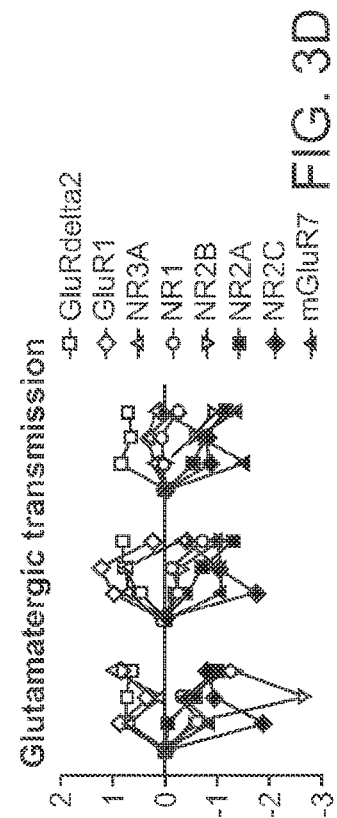
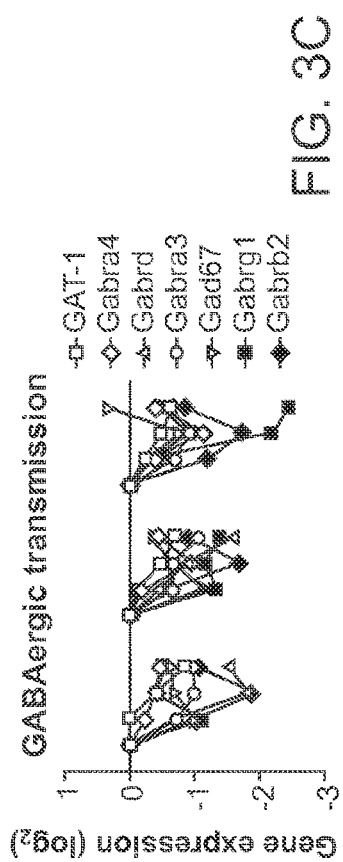
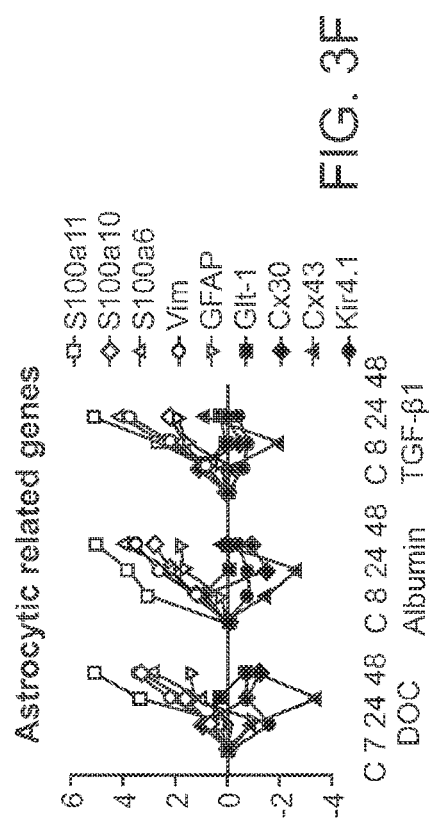
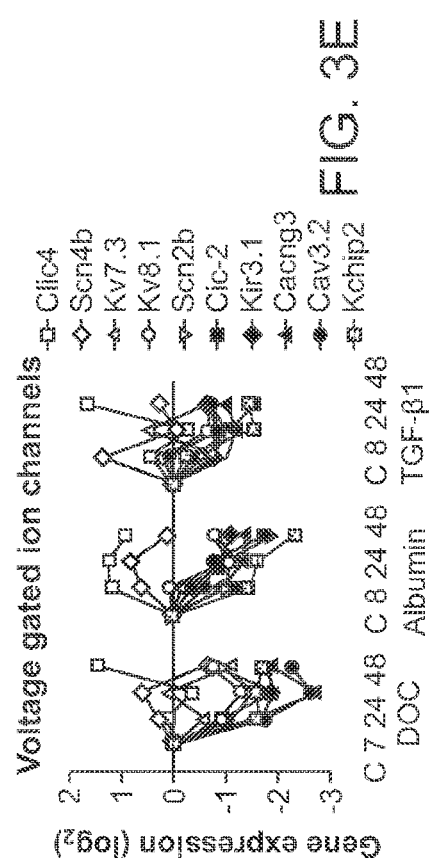
FIG. 3A  FIG. 3B  FIG. 3C  FIG. 3D  FIG. 3E  FIG. 3F

| Albumin | Albumin + blockers | GO Term | # genes | % | p-value |
|---|---|---|---|---|---|
| | | unattenuated response - downregulation | | | |
| | | transferase activity, transferring nitrogenous groups | 3 | 3.2 | 5.3E-03 |
| | | developmental process | 16 | 17.0 | 4.1E-02 |
| | | binding | 41 | 43.6 | 1.3E-02 |
| | | unattenuated response - upregulation | | | |
| | | translation regulator activity | 9 | 5.6 | 7.8E-07 |
| | | protein binding | 62 | 38.5 | 4.7E-06 |
| | | nucleotide binding | 29 | 18.0 | 1.6E-04 |
| | | intracellular signaling cascade | 23 | 14.3 | 2.3E-04 |
| | | isomerase activity | 6 | 3.7 | 2.2E-03 |
| | | cell motility | 9 | 5.6 | 1.0E-02 |
| | | nucleobase metabolic process | 3 | 1.9 | 1.1E-02 |
| | | intracellular transport | 12 | 7.5 | 1.2E-02 |
| | | cell death | 12 | 7.5 | 2.1E-02 |
| | | cytoskeleton organization & biogenesis | 9 | 5.6 | 2.4E-02 |
| | | cell proliferation | 12 | 7.5 | 2.5E-02 |
| | | transferase activity | 20 | 12.4 | 3.6E-02 |
| | | nucleic acid binding | 27 | 16.8 | 4.8E-02 |
| | | attenuated response - downregulation | | | |
| | | oxidoreductase activity | 28 | 8.6 | 9.5E-06 |
| | | vitamin binding | 8 | 2.5 | 4.9E-04 |
| | | nervous system development | 23 | 7.0 | 6.8E-04 |
| | | organic acid metabolic process | 18 | 5.5 | 9.0E-04 |
| | | ion transport | 22 | 6.7 | 9.2E-04 |
| | | electron transport | 15 | 4.6 | 1.8E-03 |
| | | cation binding | 49 | 15.0 | 2.1E-03 |
| | | transporter activity | 29 | 8.9 | 2.4E-03 |
| | | glutathione transferase activity | 4 | 1.2 | 6.7E-03 |
| | | extracellular matrix structural constituent | 5 | 1.5 | 1.3E-02 |
| | | cell growth | 7 | 2.1 | 1.7E-02 |
| | | cell adhesion | 15 | 4.6 | 2.8E-02 |
| | | transmission of nerve impulse | 12 | 3.7 | 4.0E-02 |
| | | cell proliferation | 17 | 5.2 | 4.1E-02 |
| | | phospholipase activity | 4 | 1.2 | 4.3E-02 |

FIG. 6A

| Gene symbol | fold change | |
|---|---|---|
| | albumin | albumin + blockers |
| TGF-β signaling | | |
| Spp1 | 85.4 | 10.8 |
| PAI-1 | 6.4 | 1.4 |
| Stat3 | 6.0 | 1.3 |
| Fos | 4.7 | 1.0 |
| Tgfb2 | 2.9 | 1.3 |
| Tgif | 2.7 | 1.6 |
| Smad1 | 2.7 | 1.5 |
| Jun | 2.3 | 1.0 |
| Bmp6 | -2.5 | -1.2 |
| Immune response | | |
| Ccl2 | 356.2 | 30.5 |
| Ccl7 | 59.2 | 4.2 |
| CD14 | 36.3 | 3.4 |
| Tnfrsf12a | 29.2 | 5.7 |
| CD44 | 28.6 | 5.9 |
| Gal | 9.4 | 1.8 |
| C5r1 | 5.2 | 1.2 |
| Il1rap | 4.9 | 1.0 |
| Il1r2 | 2.1 | 1.1 |
| Fn1 | 1.7 | 1.1 |
| Ion and cellular transport | | |
| Scn7a | 13.9 | 2.4 |
| Clic4 | 2.5 | 1.4 |
| Kir61 | 1.9 | 1.2 |
| SK2 | -1.5 | -1.2 |
| Cx43 | -1.6 | -1.1 |
| Chrm3 | -2.0 | 1.0 |
| Atp1a2 | -3.0 | 1.0 |
| Cx30 | -5.4 | -1.4 |
| Cx26 | -22.1 | -2.0 |
| Cell Cycle | | |
| Fosl1 | 26.1 | 1.6 |
| Gadd45g | 15.6 | 1.8 |
| Myc | 11.6 | 2.2 |
| Gadd45a | 6.7 | 2.4 |
| Cdkn1a | 4.0 | 1.7 |
| Nek6 | 3.7 | 1.8 |
| Cited2 | 1.9 | 1.3 |
| Ccnl1 | 1.8 | 1.2 |
| Tp53 | 1.7 | 1.1 |
FIG. 6B
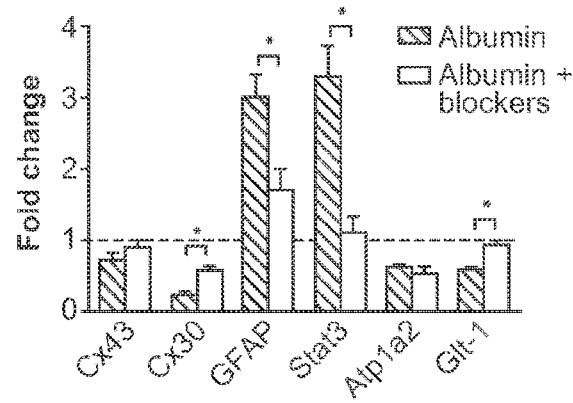
FIG. 6C
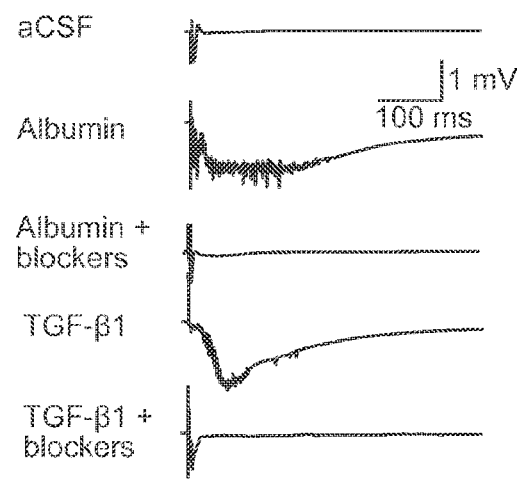
FIG. 6D
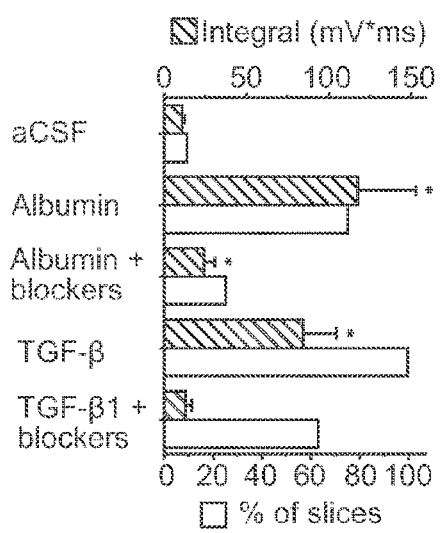
FIG. 6E a - Sham; b - treated with BSA; c - treated with a mixture of BSA and losartan potassium.

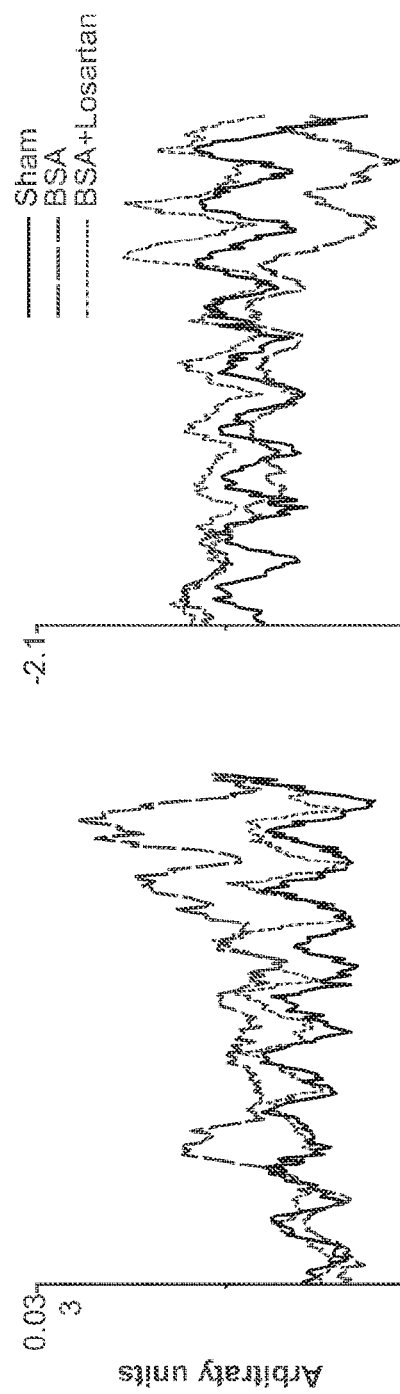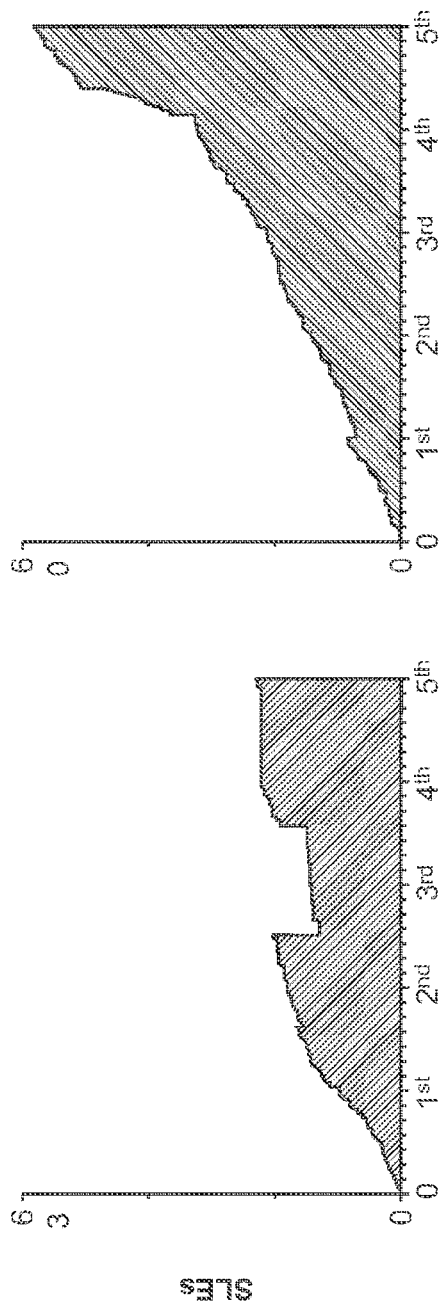
FIG. 9A  FIG. 9B  FIG. 9C  FIG. 9D

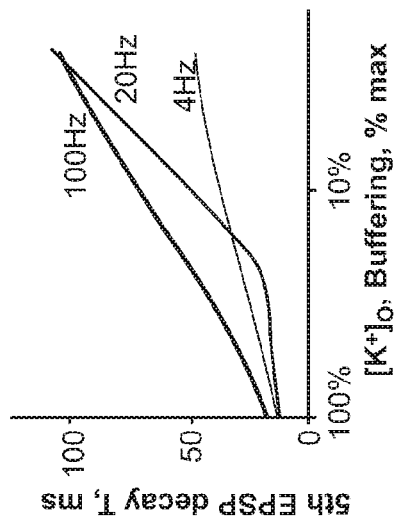
FIG. 13F
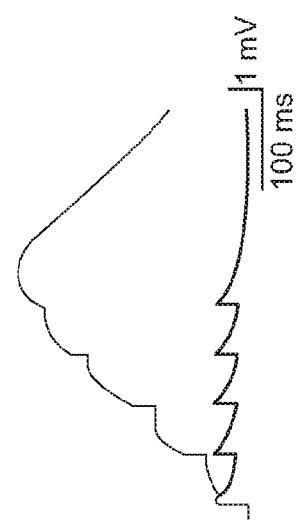
FIG. 13E
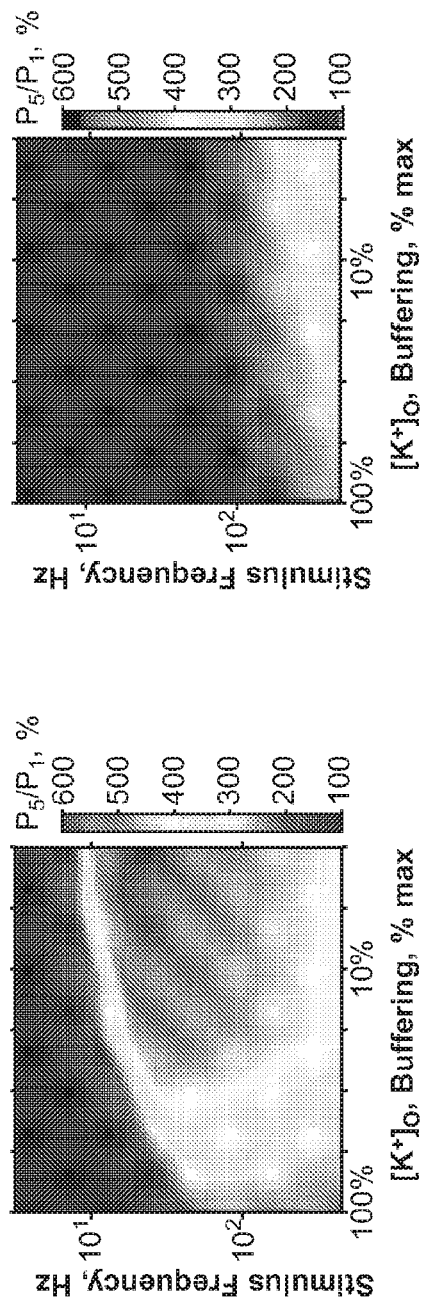
FIG. 13G
FIG. 13H

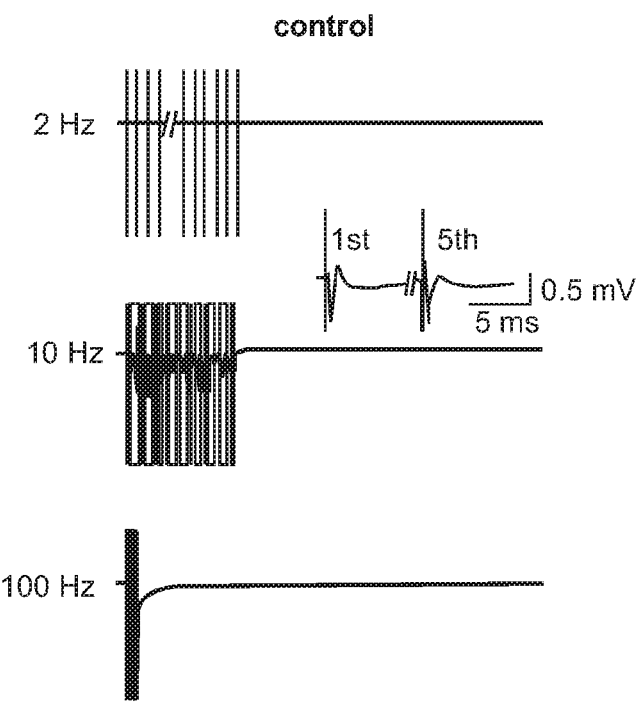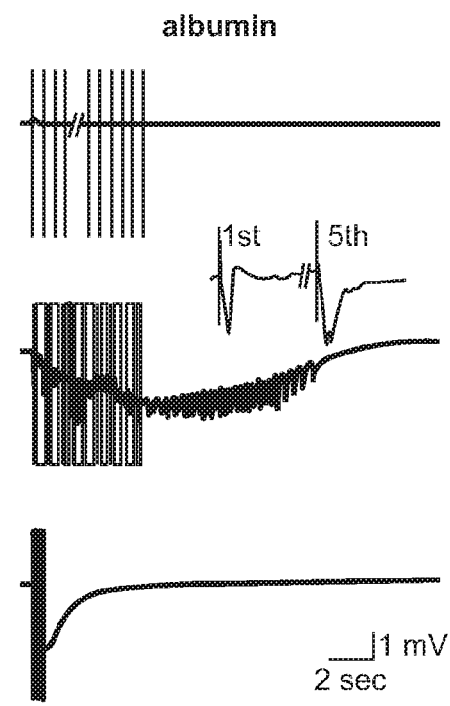
FIG. 16A  FIG. 16B
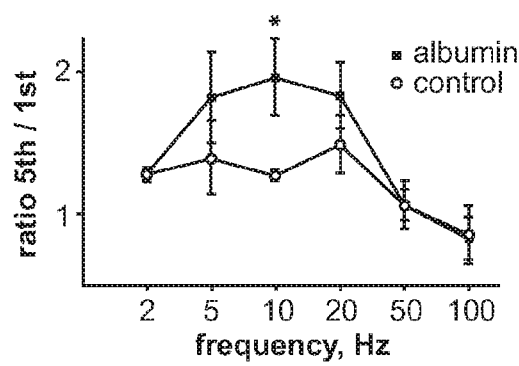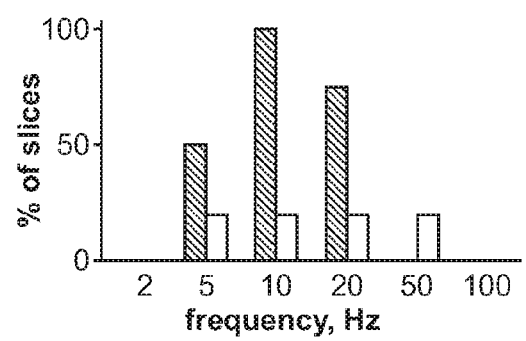
FIG. 16C  FIG. 16D

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Synthetic primer -continued

<400> SEQUENCE: 1
ccatccaatc ggtagtagcg                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
gtaacccgtt gaaccccatt                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
gaggccatgg agactctgac                                                    20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
cgaagcacat ggagaagaca                                                    20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
agcgacatgt acctccatcc                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
tacagctgtg cctcaggttg                                                    20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
gagacgacgc agacagagag                                                    20

<210> SEQ ID NO 8

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
ccactgcatg tcaatgaagg                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
ggtttgtgat gtgagcatgg                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
ctcagcacac caaggatgaa                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
gccaagatga gtcacagcaa                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
tcagagctgg atcacaatcg                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
tccttggtgt ctctcgcttt                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
```

```
tttggagatc cgcagtcttt                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
ggtcaatgta gtgggcgatt                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
ggactgcgtc ttggtcattt                                              20
```

METHODS OF TREATING COGNITIVE DECLINE WITH TRANSFORMING GROWTH FACTOR BETA INHIBITORS

CROSS-REFERENCE

This application is a divisional application of U.S. patent application Ser. No. 13/132,290, filed Nov. 11, 2011, now U.S. Pat. No. 9,468,649, which is a national stage filing under 35 U.S.C. § 371 PCT/US2009/066856, filed Dec. 4, 2009, which claims the benefit of U.S. Provisional Patent Application No. 61/120,218, filed Dec. 5, 2008, each of which applications is incorporated herein by reference in its entirety.

BACKGROUND

Epilepsy, affecting 0.5-2% of the population worldwide, is one of the most common neurological disorders. While the characteristic electrical activity in the epileptic cortex has been extensively studied, the mechanisms underlying epileptogenesis are poorly understood. Focal neocortical epilepsy often develops following traumatic, ischemic or infectious brain injury. Under these conditions, local compromise of blood-brain barrier (BBB) integrity is common, as revealed by ultrastructural studies of animal and human epileptic tissue in multiple forms of epilepsy, raising the possibility that primary vascular damage, and specifically BBB opening, may serve as an initial event leading to epilepsy. This hypothesis has been confirmed by animal studies, in which opening of the BBB was sufficient to induce delayed epileptiform activity. Subsequent studies have shown that albumin, the most common serum protein, is sufficient to recapitulate the epileptiform activity induced by BBB disruption, and that albumin is selectively taken up by astrocytes (Ivens et al., 2007).

LITERATURE

Ivens et al. (2007) *Brain* 130:535-547; WO 2008/06583; WO 2008/066626.

SUMMARY OF THE INVENTION

The present invention provides methods of preventing and treating epilepsy and other neurological disorders. The methods generally involve administering to an individual in need thereof an effective amount of an agent that blocks a transforming growth factor-beta pathway.

BRIEF DESCRIPTION OF THE DRAWINGS

FIGS. 3A-F depict gene ontology annotation analysis.

FIGS. 6A-E depict the effect of blocking TGF-β signaling on albumin-induced gene expression and epileptiform activity.

FIGS. 9A-D depict EEG changes during epileptogenesis.

FIGS. 13*a-h* illustrate application of NEURON-based model to determine the effects of [K+]o accumulation.

FIG. 16*a-d* depict in vitro recording showing frequency-dependent increased neuronal excitability and hyper-synchronous network activity during albumin-mediated epileptogenesis.

DEFINITIONS

Figure 1A:
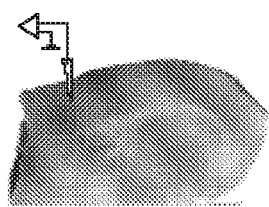
FIGS. 1A-E depict the effect of serum albumin on epileptiform activity and TGF-β pathway activation.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as laving it; (b) inhibiting the disease, i.e., arresting its development; and (c) relieving the disease, i.e., causing regression of the disease.

The terms "individual," "subject," and "patient," used interchangeably herein, refer to a mammal, including, but not limited to, murines, simians, humans, mammalian farm animals, mammalian sport animals, and mammalian pets.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a TGF-β receptor antagonist" includes a plurality of such antagonists and reference to "the active agent" includes reference to one or more active agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides methods of treating epilepsy and other neurological disorders. The methods generally involve administering to an individual in need thereof an effective amount of an agent that blocks a transforming growth factor-beta (TGF-β) pathway.

In some embodiments, an "effective amount" of an agent that blocks a TGF-β pathway is an amount that is effective to reduce the incidence of an epileptic seizure in an individual by at least about 10%, at least about 15%, at least about 20%, at least about 25%, at least about 30%, at least about 40%, at least about 50%, or more than 50%, compared to the incidence of epileptic seizure in the individual in the absence of treatment with the agent.

In some embodiments, an "effective amount" of an agent that blocks a TGF-β pathway is an amount that is effective to reduce the duration and/or severity of an epileptic seizure in an individual by at least about 10%, at least about 15%, at least about 20%, at least about 25%, at least about 30%, at least about 40%, at least about 50%, at least about 60%, at least about 70%, at least about 80%, or more than 80%, compared to the duration and/or severity in the individual in the absence of treatment with the agent.

In some embodiments, an "effective amount" of an agent that blocks a TGF-β pathway is an amount that is effective to return an astrocyte from an activated state to a resting state. In some embodiments, an "effective amount" of an agent that blocks a TGF-β pathway is an amount that is effective to reduce astrocyte dysfunction by at least about 10%, at least about 15%, at least about 20%, at least about 25%, at least about 30%, at least about 40%, at least about 50%, at least about 60%, at least about 70%, at least about 80%, or more than 80%, compared to the astrocyte dysfunction in the absence of the agent. Astrocyte function can be assessed using electrophysiological assays (e.g., current recordings, voltage clamp recordings), assays designed to test extracellular K+ concentrations (e.g., using electrodes that measure extracellular K+ levels), and the like.

In some embodiments, an "effective amount" of an agent that blocks a TGF-β pathway is an amount that is effective to increase cognitive function, e.g., in an individual having reduced cognitive function as a result of a neurodegenerative disorder such as Alzheimer's Disease (AD). In some embodiments, an "effective amount" of an agent that blocks a TGF-β pathway is an amount that is effective to increase cognitive function in an individual having reduced cognitive function as a result of AD by at least about 10%, at least about 15%, at least about 20%, at least about 25%, at least about 30%, at least about 40%, at least about 50%, at least about 60%, at least about 70%, at least about 80%, at least about 2-fold, at least about 5-fold, or at least about 10-fold, or more, compared to the cognitive function in the individual in the absence of treatment with the agent.

A subject method is suitable for treating various disorders including, e.g., epilepsy, traumatic brain injury, stroke, and neurodegenerative diseases. A subject method is suitable for treating epilepsy (including posttraumatic epilepsy and post-ischemic epilepsy (i.e. after stroke). Parkinson's disease, psychosis, migraine, cerebral ischemia, Alzheimer's disease and other degenerative diseases such as neurological deficits associated with acquired immunodeficiency syndrome, traumatic brain injury, inappropriate neuronal activity resulting in neurodysthesias in diseases such as diabetes, neurological complications of diabetes mellitus, multiple sclerosis (MS) and motor neuron disease, ataxias, muscular rigidity (spasticity), and antyotrophic lateral sclerosis (ALS).

TGF-β Pathway Blockers

Suitable agents that block a TGF-β pathway include, e.g., TGF-β receptor (TGF-β-R) antagonists; agents that inhibit the activity of a TGF-β pathway element downstream of a TGF-β-R; and agents that reduce the level of a TGF-β pathway element downstream of a TGF-β-R. TGF-β pathway inhibitors include, e.g., agents that inhibit phosphorylation of a TGF-β-R; agents that inhibit a kinase activity of a TGF-β-R; agents that inhibit phosphorylation of a TGF-β pathway element downstream of a TGF-β-R; and the like. TGF-β pathway elements that are downstream of a TGF-β-R and that are targets of therapeutic agents as described herein include, e.g., NFκB, Smad1, Smad2, Smad6. Stat3. Stat1, Jak1, MAPK, Noggin, Thbs1 (thrombospondin 1), bone morphogenic protein-4 (BMP4), bone morphogenic protein-6 (BMP6), spp-1 (secreted phosphoprotein 1), Pal-1, TGFB-induced factor homeobox 1 (Tgif1), Tumor necrosis factor (TNF), and ENG.

TGF-β Receptor Antagonists

Suitable TGF-β-R antagonists include inhibitors of kinase activity of a TGF-β-R. TGF-β receptors include, e.g., TGF-βI, TGF-β-II, ALK1, and ALK5.

Suitable TGF-β-R antagonists include, e.g., a Sm2 peptide as disclosed in U.S. Patent Publication No. 2005/0136043; inhibitors of aldosterone; anti-TGFβ antibodies, renin inhibitors, angiotensin converting enzyme (ACE) inhibitors; angiotensin II (AII) receptor antagonists; anti-TGF-β-R antibodies; and proteoglycans. Proteoglycans include, e.g., decorin, biglycan, fibromodulin, lumican, betaglycan and endoglin.

Aldosterone inhibitors include, e.g., eplerenone (Inspra™): (7α, 11α, 17α)-pregn-4-ene-7,21-dicarboxylic acid,9,11-epoxy-17-hydroxy-3-oxo-,γ-lactone, methyl ester and compounds related thereto (U.S. Pat. No. 4,559,332); spironolactone (Aldactone™): 7α-acetylthio-3-oxo-17α- pregn-4-ene-21,17-carbolactone and compounds related thereto; and a compound as described in, e.g., U.S. Pat. No. 6,410,524.

AII receptor antagonists include, e.g., losartan (Cozaar™): 2-butyl-4-chloro-1-[p-(o-1H-tetrazol-5-ylphenyl) benzyl]imidazole-5-methanol, monopotassium salt and the various substituted imidazole derivatives and other compounds related thereto (see, e.g., U.S. Pat. No. 5,138,069; and WO 2007/020533); valsartan, (Diovan™): N-[p-(o-1H-tetrazol-5-yl-phenyl)benzyl]-N-valeryl-L-valine and compounds related thereto (U.S. Pat. No. 5,399,578); irbesartan (Avapro™): 2-n-butyl-4-spirocyclopentane-1-((2'-tetrazol-5-yl)biphenyl4-yl)-2-imidazolin-5-one and compounds related thereto (U.S. Pat. Nos. 5,270,317 and 5,352,788); candesartan (Amias™, Atacand™): 1-(cyclohexyloxycarbonyloxy)ethyl-2-ethoxy-1-[[2'-(1H-tetrazol-5-yl)biphenyl-4-yl]methyl]benzimidazole-7-carboxylate and compounds related thereto (in U.S. Pat. No. 5,196,444); telmisartan (Micardis™): 4'-[(1,4'-dimethyl-2'-propyl[2,6-bi-1H-benzimidazol]-1-yl)methyl]-[1,1'-biphenyl]-2-carboxylic acid and compounds related thereto (European Pat. Application No. 6502314); tasosartan (Verdia™): 5,8-dihydro-2,4-dimethyl-8-[p-(o-1H-tetrazol-5-ylphenyl]pyrido[2,3-d]pyrimidin-7(6H)-one and compounds related thereto (U.S. Pat. No. 5,149,699); eprosartan (Teveten™): 4-([2-butyl-5-[2-carboxy-2-(thiophen-2-ylmethyl)eth-1-en-1-yl]-1H-imidazol-1-yl]methyl)benzoic acid and compounds related thereto (U.S. Pat. No. 5,185,351); saralasin: 1-(N-methylglycine)-5-L-valine-8-L-alanineangiotensin II (an octapeptide analog of Ang II (bovine) with amino acids 1 and 8 replaced with sarcosine and alanine, respectively; and a compound as disclosed in. e.g., U.S. Pat. Nos. 5,484,780; 6,028,091; and 6,329,384.

ACE inhibitors include, e.g., benazepril (Lotensin™, Lotrel™): 3-[[1-(ethoxy-carbonyl)-3-phenyl-(1S)-propyl]amino]-2,3,4,5-tetrahydro-2-oxo-1H-1-(3S)-benzazepine-1-acetic acid monohydrochloride and its metabolite benazeprilat and compounds related thereto (U.S. Pat. No. 4,410, 520); captopril (Capoten™): 1-[(2S)-3-mercapto-2-methylpropionyl]-L-proline and compounds related thereto (U.S. Pat. No. 4,105,776); enalapril (Vasotec™): 1-[N-[(S)-1-carboxy-3-phenylpropyl]-L-alanyl]-L-proline-1'-ethyl ester; lisinopril (Zestril™, Privinil™): 1-[N.sub.2-[(S)-1-carboxy-3-phenylpropyl]-L-lysyl]-L-proline and the various carboxyalkyl dipeptide derivatives and compounds related thereto (U.S. Pat. Nos. 4,374,829, 6,468,976, and 6,465, 615); perindopril erbumine (Aceon™, Coversyl™): (2S, 3αS,7αS)-1-[(S)—N-[(S)-1-carboxy-butyl]alanyl]hexahydro-2-indolinecarboxylic acid, 1-ethyl ester and compounds related thereto; quinapril (Accupril™): (3S)-2-[N-[(S)-1-ethoxycarbonyl-3-phenylpropyl]-L-alanyl]-1,2,3, 4-tetrahydro-isoquinoline-3-carboxylique monochlorhydrate and compounds related thereto; ramipril (Altace™): (2S,3αS,6αS)-1[(S)—N-[(S)-1-carboxy-3-phenylpropyl]alanyl]octahydrocyclopenta[β]pyrrole-2-carboxylic acid, 1-ethyl ester and compounds related thereto; trandolapril (Mavik™): (2S,3αR,7αS)-1-[(S)—N-[(S)-Carboxy-3-phenylpropyl]alanyl]hexa-hydro-2-indolinecarboxylic acid, 1-ethyl ester and compounds related thereto; fosinopril (Monopril™): L-proline, 4-cyclohexyl-1-[[[2-methyl-1-(1-oxopropoxy)propoxyl](4-phenylbutyl) phosphinyl]acetyl] sodium salt, trans-, and compounds related thereto; moexipril (Univasc™): 3S-[2[R*(R*)],3R*]]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid monohydrochloride and compounds related thereto; and imidapril (Tanatril™): (−)-4S)-3-[(2S)-2-[[(1S)-1-ethoxycarbonyl-3-phenylpropyl]amino]-propionyl-]-1-methyl-2-oxoimidazolidine-4-carboxylic acid hydrochloride and compounds related thereto.

Renin inhibitors include, e.g., aliskiren (SPP100): 2(S),4 (S),5(S),7(S)—N-(2-carbamoyl-2-methylpropyl)-5-amino-4-hydroxy-2,7-diisopropyl-8-[4-methoxy-3-(3-methoxypropoxy)phenyl]-octanamid hemifumarate and compounds related thereto as disclosed in U.S. Pat. No. 5,719,141 and WO 01/09079; enalkiren: [1S-(1R*,2S*,3R*)]-N-(3-amino-3-methyl-1-oxobutyl)-O-methyl-L-tyrosyl-N-[1-(cyclohexylmethyl)-2,3-dihydroxy-5-methylhexyl]-L-histidinamide and compound related thereto; and remikiren: (S)-2-tert-Butylsulphonylmethyl-N-[(S)-1-[(1S,2R,3S)-1-cyclo-hexylmethyl-3-cyclopropyl-2,3-dihydroxypropylcarbamoyl]-2-(H-imidazol-4-yl)methyl]-3-phenlylpropionamide and compound related thereto.

Suitable TGF-β pathway inhibitors include selective inhibitors of TGF-β-RII.

NFκB Inhibitors

Suitable NKκB inhibitors include, e.g., caffeic acid phenylethyl ester (CAPE), DM-CAPE, SN-50 peptide, hymenialdisine, and pyrrolidone dithiocarbamate.

MAPK Inhibitors

Mitogen-activated protein kinase (MAPK) inhibitor compounds suitable for the invention include, for example, 4-(4-fluorophenyl)-2-(4-methylsulfinylphenyl)-5-(4-pyridyl)-1H-imidazole (SB203580), 4-(3-Iodophenyl)-2-(4-methylsulfinylphenyl)-5-(4-pyridyl)-1H-imidazole (SB203580-iodo), 4-(4-fluorophenyl)-2-(4-hydroxyphenyl)-5-(4-pyridyl)-1H-imidazole (SB202190), 5-(2-amino-4-pyrimidyl)-4-(4-fluorophenyl)-1-(4-piperidinyl)imidazole (SB220025), 4-(4-fluorophenyl)-2-(4-nitrophenyl)-5-(4-pyridyl)-1H-imidazole (PD 169316), and 2'-amino-3'-methoxyflavone (PD98059).

Smad Inhibitors

Suitable Smad inhibitors include, e.g., A-83-01 (3-(6-Methylpyridin-2-yl)-1-phenylthiocarbamoyl-4-quinolin-4-ylpyrazole; Alk-5 inhibitor, Masayoshi et al, 2005), GW6604 (2-phenyl-4-(3-pyridin-2-yl-1H-pyrazol-4-yl) pyridine; Alk-5 inhibitor. Sawyer et al, 2003), and SB-431542 (4-(5-benzo[1,3]dioxol-5-yl-4-pyridin-2-yl-1H-imidazol-2-yl)-benzamide). Also suitable for use is a pyrimidine derivative as described in WO 2008/006583.

Interfering Nucleic Acids

In some embodiments, an agent that inhibits TGF-β signaling is an inhibitory (or "interfering") nucleic acid. Interfering nucleic acids (RNAi) include nucleic acids that provide for decreased levels of a TGF-β pathway element in a cell, e.g., a neuronal cell. Interfering nucleic acids include, e.g., a short interfering nucleic acid (siNA), a short interfering RNA (siRNA), a double-stranded RNA (dsRNA), a micro-RNA (miRNA), and a short hairpin RNA (shRNA) molecule.

The term "short interfering nucleic acid," "siNA," "short interfering RNA," "siRNA." "short interfering nucleic acid molecule," "short interfering oligonucleotide molecule," or "chemically-modified short interfering nucleic acid molecule" as used herein refers to any nucleic acid molecule capable of inhibiting or down regulating gene expression, for example by mediating RNA interference "RNAi" or gene silencing in a sequence-specific manner. Design of RNAi molecules when given a target gene is routine in the art. See also US 2005/0282188 (which is incorporated herein by reference) as well as references cited therein. See, e.g., Pushparaj et al. Clin Exp Pharmacol Physiol. 2006 May-June; 33(5-6):504-10; Lutzelberger et al. Handb Exp Pharmacol. 2006; (173):243-59; Aronin et al. Gene Ther. 2006

March; 13(6):509-16; Xie et al. Drug Discov Today. 2006 January; 11(1-2):67-73; Grunweller et al. Curr Med Chem. 2005; 12(26):3143-61; and Pekaraik et al. Brain Res Bull. 2005 Dec. 15; 68(1-2):115-20. Epub 2005 Sep. 9.

Methods for design and production of siRNAs to a desired target are known in the art, and their application to TGF-β pathway element-encoding nucleic acids will be readily apparent to the ordinarily skilled artisan, as are methods of production of siRNAs having modifications (e.g., chemical modifications) to provide for, e.g., enhanced stability, bioavailability, and other properties to enhance use as therapeutics. In addition, methods for formulation and delivery of siRNAs to a subject are also well known in the art. See, e.g., US 2005/0282188; US 2005/0239731; US 2005/0234232; US 2005/0176018; US 2005/0059817; US 2005/020525; US 2004/0192626; US 2003/0073640; US 2002/0150936; US 2002/0142980; and US2002/0120129, each of which are incorporated herein by reference.

Publicly available tools to facilitate design of siRNAs are available in the art. See, e.g., DEQOR: Design and Quality Control of RNAi (available on the internet at cluster-1.mpi-cbg.de/Deqor/deqor.html). See also, Henschel et al. Nucleic Acids Res. 2004 Jul. 1; 32(Web Server issue):W113-20. DEQOR is a web-based program which uses a scoring system based on state-of-the-art parameters for siRNA design to evaluate the inhibitory potency of siRNAs. DEQOR, therefore, can help to predict (i) regions in a gene that show high silencing capacity based on the base pair composition and (ii) siRNAs with high silencing potential for chemical synthesis. In addition, each siRNA arising from the input query is evaluated for possible cross-silencing activities by performing BLAST searches against the transcriptome or genome of a selected organism. DEQOR can therefore predict the probability that an mRNA fragment will cross-react with other genes in the cell and helps researchers to design experiments to test the specificity of siRNAs or chemically designed siRNAs.

siNA molecules can be of any of a variety of forms. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. siNA can also be assembled from two separate oligonucleotides, where one strand is the sense strand and the other is the antisense strand, wherein the antisense and sense strands are self-complementary. In this embodiment, each strand generally comprises nucleotide sequence that is complementary to nucleotide sequence in the other strand; such as where the antisense strand and sense strand form a duplex or double stranded structure, for example wherein the double stranded region is about 15 base pairs to about 30 base pairs. e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 nucleotides to about 25 or more nucleotides of the siNA molecule are complementary to the target nucleic acid or a portion thereof).

Alternatively, the siNA can be assembled from a single oligonucleotide, where the self-complementary sense and antisense regions of the siNA are linked by a nucleic acid-based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof.

The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (e.g., where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, Cell., 110, 563-574 and Schwarz et al., 2002, Molecular Cell, 10, 537-568), or 5',3'-diphosphate.

In certain embodiments, the siNA molecule contains separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. In certain embodiments, the siNA molecules comprise nucleotide sequence that is complementary to nucleotide sequence of a target gene. In another embodiment, the siNA molecule interacts with nucleotide sequence of a target gene in a manner that causes inhibition of expression of the target gene.

As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. siNAs do not necessarily require the presence of nucleotides having a 2'-hydroxy group for mediating RNAi and as such, siNA molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'—OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON."

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence a target gene at the post-transcriptional level and/or at the pre-transcriptional level. In a non-limiting example, epigenetic regulation of gene expression by siNA molecules of the invention can result from siNA mediated modification of chromatin structure or methylation pattern to alter gene expression (see, for example, Verdel et al., 2004. Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science. 297, 2232-2237).

siNA molecules contemplated herein can comprise a duplex forming oligonucleotide (DFO) see, e.g., WO 05/019453; and US 2005/0233329, which are incorporated herein by reference). siNA molecules also contemplated herein include multifunctional siNA, (see, e.g., WO 05/019453 and US 2004/0249178). The multifunctional siNA can comprise sequence targeting, for example, two regions of Skp2.

siNA molecules contemplated herein can comprise an asymmetric hairpin or asymmetric duplex. By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

Stability and/or half-life of siRNAs can be improved through chemically synthesizing nucleic acid molecules with modifications (base, sugar and/or phosphate) can prevent their degradation by serum ribotnucleases, which can increase their potency (see e.g., Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra all of which are incorporated by reference herein, describing various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, TIBS. 17, 34; Usman et al., 1994. Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Earnshaw and Gait, 1998, Biopolymers (Nucleic Acid Sciences), 48, 39-55; Verma and Eckstein, 1998, Annu. Rev. Biochem., 67, 99-134; and Burlina et al., 1997. Bioorg. Med. Chem., 5, 1999-2010; each of which are hereby incorporated in their totality by reference herein). In view of such teachings, similar modifications can be used as described herein to modify the siNA nucleic acid molecules of disclosed herein so long as the ability of siNA to promote RNAi is cells is not significantly inhibited.

Short interfering nucleic acid (siNA) molecules having chemical modifications that maintain or enhance activity are contemplated herein. Such a nucleic acid is also generally more resistant to nucleases than an unmodified nucleic acid. Accordingly, the in vitro and/or in vivo activity should not be significantly lowered. Nucleic acid molecules delivered exogenously are generally selected to be stable within cells at least for a period sufficient for transcription and/or translation of the target RNA to occur and to provide for modulation of production of the encoded mRNA and/or polypeptide so as to facilitate reduction of the level of the target gene product.

Production of RNA and DNA molecules can be accomplished synthetically and can provide for introduction of nucleotide modifications to provide for enhanced nuclease stability. (see, e.g., Wincott et al., 1995, Nucleic Acids Res. 23, 2677; Caruthers et al., 1992, Methods in Enzymology 211, 3-19, incorporated by reference herein. In one embodiment, nucleic acid molecules of the invention include one or more (e.g., about 1, 2, 3, 4, 5, 6, 7, 8, 9, 10, or more) G-clamp nucleotides, which are modified cytosine analogs which confer the ability to hydrogen bond both Watson-Crick and Hoogsteen faces of a complementary guanine within a duplex, and can provide for enhanced affinity and specificity to nucleic acid targets (see, e.g., Lin et al. 1998, J. Am. Chem. Soc., 120, 8531-8532). In another example, nucleic acid molecules can include one or more (e.g., about 1, 2, 3, 4, 5, 6, 7, 8, 9, 10, or more) LNA "locked nucleic acid" nucleotides such as a 2',4'-C methylene bicyclo nucleotide (see, e.g., Wengel et al., WO 00/66604 and WO 99/14226).

siNA molecules can be provided as conjugates and/or complexes, e.g., to facilitate delivery of siNA molecules into a cell. Exemplary conjugates and/or complexes include those composed of an siNA and a small molecule, lipid, cholesterol, phospholipid, nucleoside, antibody, toxin, negatively charged polymer (e.g., protein, peptide, hormone, carbohydrate, polyethylene glycol, or polyamine). In general, the transporters described are designed to be used either individually or as part of a multi-component system, with or without degradable linkers. These compounds can improve delivery and/or localization of nucleic acid molecules into cells in the presence or absence of serum (see, e.g., U.S. Pat. No. 5,854,038). Conjugates of the molecules described herein can be attached to biologically active molecules via linkers that are biodegradable, such as biodegradable nucleic acid linker molecules.

BBB Disruption

In some embodiments, an individual who is being considered for treatment with a subject method is first assessed for blood-brain barrier (BBB) disruption. Where the individual is determined to have BBB disruption, the individual is treated with an effective amount of an agent that inhibits a TGF-β pathway. Methods of determining whether an individual has BBB disruption are known in the art.

Formulations, Dosages, and Routes of Administration

An agent that blocks a TGF-β pathway can be provided together with a pharmaceutically acceptable excipient. Pharmaceutically acceptable excipients are known to those skilled in the art, and have been amply described in a variety of publications, including, for example, A. Gennaro (1995) "Remington: The Science and Practice of Pharmacy", 19th edition, Lippincott, Williams. & Wilkins Formulations An agent that blocks a TGF-β pathway is also referred to herein as an "active agent," "agent," or "drug." In the subject methods, the active agent(s) may be administered to the host using any convenient means capable of resulting in the desired reduction in disease symptoms.

An active agent can be incorporated into a variety of formulations for therapeutic administration. More particularly, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, an active agent may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an active agent calculated in an amount sufficient to produce the desired effect in association with a pharmaceutically acceptable diluent, carrier or vehicle. The specifications for the active agents depend on the particular compound employed and the effect to be achieved, and the pharmacodynamics associated with each compound in the host.

Other modes of administration will also find use with the subject invention. For instance, an active agent can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), or about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An active agent can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Oral Formulations

In some embodiments, an active agent is formulated for oral delivery to an individual in need of such an agent.

For oral delivery, a subject formulation comprising an active agent will in some embodiments include an enteric-soluble coating material. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™, and shellac.

As one non-limiting example of a suitable oral formulation, an active agent is formulated with one or more pharmaceutical excipients and coated with an enteric coating, as described in U.S. Pat. No. 6,346,269. For example, a solution comprising an active agent and a stabilizer is coated onto a core comprising pharmaceutically acceptable excipients, to form an active agent-coated core; a sub-coating layer is applied to the active agent-coated core, which is then coated with an enteric coating layer. The core generally includes pharmaceutically inactive components such as lactose, a starch, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin, and castor oil. Suitable solvents for the active agent include aqueous solvents. Suitable stabilizers include alkali-metals and alkaline earth metals, bases of phosphates and organic acid salts and organic amines. The sub-coating layer comprises one or more of an adhesive, a plasticizer, and an anti-tackiness agent. Suitable anti-tackiness agents include talc, stearic acid, stearate, sodium stearyl fumarate, glyceryl behenate, kaolin and aerosil. Suitable adhesives include polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalates (CAP), xanthan gum, alginic acid, salts of alginic acid, Eudragit™, copolymer of methyl acrylic acid/methyl methacrylate with polyvinyl acetate phthalate (PVAP). Suitable plasticizers include glycerin, polyethylene glycol, triethyl citrate, tributyl citrate, propanyl triacetate and castor oil. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™ and shellac.

Suitable oral formulations also include an active agent, formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) Biomaterials 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly(lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B.V.).

Suitable oral formulations also include an active agent formulated with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVIT™ (Mistral Pharma Inc.); RingCap™ (Alza Corp.); Smartrix® (Smartrix Technologies, Inc.); SQZgel™ (MacroMed, Inc.); Geomatrix™ (Skye Pharma, Inc.); Oros® Tri-layer (Alza Corporation); and the like.

Also suitable for use are formulations such as those described in U.S. Pat. No. 6,296,842 (Alkermes Controlled Therapeutics, Inc.); U.S. Pat. No. 6,187,330 (Scios, Inc.); and the like.

Also suitable for use herein are formulations comprising an intestinal absorption enhancing agent. Suitable intestinal absorption enhancers include, but are not limited to, calcium chelators (e.g., citrate, ethylenediamine tetracetic acid); surfactants (e.g., sodium dodecyl sulfate, bile salts, palmitoylcarnitine, and sodium salts of fatty acids); toxins (e.g., zonula occludens toxin); and the like.

Controlled Release Formulations

In some embodiments, an active agent is formulated in a controlled release formulation.

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms,* 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, Controlled Release Technologies: Methods, Theory and Applications, 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, Novel Drug Delivery Systems, 1992 (Marcel Dekker, Inc.). Some of these formulations will now be discussed in more detail.

Enteric coatings are applied to tablets to prevent the release of drugs in the stomach either to reduce the risk of unpleasant side effects or to maintain the stability of the drug which might otherwise be subject to degradation of expose to the gastric environment. Most polymers that are used for this purpose are polyacids that function by virtue or the fact that their solubility in aqueous medium is pH-dependent, and they require conditions with a pH higher than normally encountered in the stomach.

One exemplary type of oral controlled release structure is enteric coating of a solid or liquid dosage form. The enteric coatings are designed to disintegrate in intestinal fluid for ready absorption. Delay of absorption of the active agent that is incorporated into a formulation with an enteric coating is dependent on the rate of transfer through the gastrointestinal tract, and so the rate of gastric emptying is an important factor. Some investigators have reported that a multiple-unit type dosage form, such as granules, may be superior to a single-unit type. Therefore, in one exemplary embodiment, an active agent is contained in an enterically coated multiple-unit dosage form. In an exemplary embodiment, an active agent dosage form is prepared by spray-coating granules of an active agent-enteric coating agent solid dispersion on an inert core material. These granules can result in prolonged absorption of the drug with good bioavailability.

Suitable enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa. Application of solid dispersions of Nifedipine with enteric coating agent to prepare a sustained-release dosage form, Chem Pharm. Bull. 33: 1615-1619 (1985). Various enteric coating materials may be selected on the basis of testing to achieve an enteric coated dosage form designed ab initio to have an optimal combination of dissolution time, coating thicknesses and diametral crushing strength. S. C. Porter et al., The Properties of Enteric Tablet Coatings Made From Polyvinyl Acetate-phthalate and Cellulose acetate Phthalate, J. Pharm. Pharmacol. 22:42p (1970).

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method. Akihiko Hasegawa, Super Saturation Mechanism of Drugs from Solid Dispersions with Enteric Coating Agents, (Chem. Pharm. Bull. 36: 4941-4950 (1998). The solid dispersions may be also called solid-state dispersions. The term "coprecipitates" may also be used to refer to those preparations obtained by the solvent methods.

The selection of the carrier may have an influence on the dissolution characteristics of the dispersed drug (e.g., active agent) because the dissolution rate of a component from a surface may be affected by other components in a multiple component mixture. For example, a water-soluble carrier may result in a fast release of the drug from the matrix, or a poorly soluble or insoluble carrier may lead to a slower release of the drug from the matrix. The solubility of the active agent may also be increased owing to some interaction with the carriers.

Examples of carriers useful in solid dispersions include, but are not limited to, water-soluble polymers such as polyethylene glycol, polyvinylpyraolidone, and hydroxypropylmethyl-cellulose. Alternative carriers include phosphatidylcholine. Phosphatidylcholine is an amphoteric but water-insoluble lipid, which may improve the solubility of otherwise insoluble active agents in an amorphous state in phosphatidylcholine solid dispersions.

Other carriers include polyoxyethylene hydrogenated castor oil. Poorly water-soluble active agents may be included in a solid dispersion system with an enteric polymer such as hydroxypropylmethylcellulose phthalate and carboxymethylethylcellulose, and a non-enteric polymer, hydroxypropylmethylcellulose. Another solid dispersion dosage form includes incorporation of the drug of interest (e.g., an active agent) with ethyl cellulose and stearic acid in different ratios.

There are various methods commonly known for preparing solid dispersions. These include, but are not limited to, the melting method, the solvent method and the melting-solvent method.

Another controlled release dosage form is a complex between an ion exchange resin and an active agent. Ion exchange resin-drug complexes have been used to formulate sustained-release products of acidic and basic drugs. In one exemplary embodiment, a polymeric film coating is provided to the ion exchange resin-drug complex particles, making drug release from these particles diffusion controlled. Se Y. Raghunathan et al., *Sustained-released drug delivery system I: Coded ion-exchange resin systems for phenylpropanolamine and other drugs*, J. Pharm. Sciences 70: 379-384 (1981).

Injectable microspheres are another controlled release dosage form. Injectable micro spheres may be prepared by non-aqueous phase separation techniques, and spray-drying techniques. Microspheres may be prepared using polylactic acid or copoly(lactic/glycolic acid). Shigeyuki Takada. *Utilization of an Amorphous Form of a Water-Soluble GPIIb/IIIa Antagonist for Controlled Release From Biodegradable Micro spheres*, Pharm. Res. 14:1146-1150 (1997), and ethyl cellulose, Yoshiyuki Koida, *Studies on Dissolution Mechanism of Drugs from Ethyl Cellulose Microcapsules*, (Chem. Pharm. Bull. 35:1538-1545 (1987).

Other controlled release technologies that may be used include, but are not limited to, SODAS (Spheroidal Oral Drug Absorption System), INDAS (Insoluble Drug Absorption System), IPDAS (Intestinal Protective Drug Absorption System), MODAS (Multiporous Oral Drug Absorption System), EFVAS (Effervescent Drug Absorption System). PRODAS (Programmable Oral Drug Absorption System), and DUREDAS (Dual Release Drug Absorption System) available from Elan Pharmaceutical Technologies. SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate release granulate. MODAS are controlled release single unit dosage forms. Each tablet consists of an inner core surrounded by a semipermeable multiparous membrane that controls the rate of drug release. EFVAS is an effervescent drug absorption system. PRODAS is a family of multi particulate formulations utilizing combinations of immediate release and controlled release mini-tablets. DUREDAS is a bilayer tablet formulation providing dual release rates within the one dosage form. Although these dosage forms are known to one of skill, certain of these dosage forms will now be discussed in more detail.

INDAS was developed specifically to improve the solubility and absorption characteristics of poorly water soluble drugs. Solubility and, in particular, dissolution within the fluids of the gastrointestinal tract is a key factor in determining the overall oral bioavailability of poorly water soluble drug. By enhancing solubility, one can increase the overall bioavailability of a drug with resulting reductions in dosage. INDAS takes the form of a high energy matrix tablet, production of which is comprised of two distinct steps: the drug in question is converted to an amorphous form through a combination of energy, excipients, and unique processing procedures.

Once converted to the desirable physical form, the resultant high energy complex may be stabilized by an absorption process that utilizes a novel polymer cross-linked technology to prevent recrystallization. The combination of the change in the physical state of the active agent coupled with the solubilizing characteristics of the excipients employed enhances the solubility of the active agent. The resulting absorbed amorphous drug complex granulate may be formulated with a gel-forming erodible tablet system to promote substantially smooth and continuous absorption.

IPDAS is a multi-particulate tablet technology that may enhance the gastrointestinal tolerability of potential irritant and ulcerogenic drugs. Intestinal protection is facilitated by the multi-particulate nature of the IPDAS formulation which promotes dispersion of an irritant lipoate throughout the gastrointestinal tract. Controlled release characteristics of the individual beads may avoid high concentration of drug being both released locally and absorbed systemically. The combination of both approaches serves to minimize the potential harm of an active agent with resultant benefits to patients.

IPDAS is composed of numerous high density controlled release beads. Each bead may be manufactured by a two step process that involves the initial production of a micromatrix with embedded active agent and the subsequent coating of this micromatrix with polymer solutions that form a rate-limiting semipermeable membrane in vivo. Once an IPDAS tablet is ingested, it may disintegrate and liberate the beads in the stomach. These beads may subsequently pass into the duodenum and along the gastrointestinal tract, e.g., in a controlled and gradual manner, independent of the feeding state. Release of the active agent occurs by diffusion process through the micromatrix and subsequently through the pores in the rate controlling semipermeable membrane. The release rate from the IPDAS tablet may be customized to deliver a drug-specific absorption profile associated with optimized clinical benefit. Should a fast onset of activity be necessary, immediate-release granulate may be included in the tablet. The tablet may be broken prior to administration, without substantially compromising drug release, if a reduced dose is required for individual titration.

MODAS is a drug delivery system that may be used to control the absorption of water soluble agents. Physically MODAS is a non-disintegrating table formulation that manipulates drug release by a process of rate limiting diffusion by a semipermeable membrane formed in vivo. The diffusion process essentially dictates the rate of presentation of drug to the gastrointestinal fluids, such that the uptake into the body is controlled. Because of the minimal use of excipients, MODAS can readily accommodate small dosage size forms. Each MODAS tablet begins as a core containing active drug plus excipients. This core is coated with a solution of insoluble polymers and soluble excipients. Once the tablet is ingested, the fluid of the gastrointestinal tract may dissolve the soluble excipients in the outer coating leaving substantially the insoluble polymer. What results is a network of tiny, narrow channels connecting fluid from the gastrointestinal tract to the inner drug core of water soluble drug. This fluid passes through these channels, into the core, dissolving the drug, and the resultant solution of drug may diffuse out in a controlled manner. This may permit both controlled dissolution and absorption. An advantage of this system is that the drug-releasing pores of the tablet are distributed over substantially the entire surface of the tablet. This facilitates uniform drug absorption reduces aggressive unidirectional drug delivery. MODAS represents a very flexible dosage form in that both the inner core and the outer semipermeable membrane may be altered to suit the individual delivery requirements of a drug. In particular, the addition of excipients to the inner core may help to produce a microenvironment within the tablet that facilitates more predictable release and absorption rates. The addition of an immediate release outer coating may allow for development of combination products.

Additionally, PRODAS may be used to deliver an active agent. PRODAS is a multi particulate drug delivery technology based on the production of controlled release mini tablets in the size range of 1.5 to 4 mm in diameter. The PRODAS technology is a hybrid of multi particulate and hydrophilic matrix tablet approaches, and may incorporate, in one dosage form, the benefits of both these drug delivery systems.

In its most basic form, PRODAS involves the direct compression of an immediate release granulate to produce individual mini tablets that contain an active agent. These mini tablets are subsequently incorporated into hard gels and capsules that represent the final dosage form. A more beneficial use of this technology is in the production of controlled release formulations. In this case, the incorporation of various polymer combinations within the granulate may delay the release rate of drugs from each of the individual mini tablets. These mini tablets may subsequently be coated with controlled release polymer solutions to provide additional delayed release properties. The additional coating may be necessary in the case of highly water soluble drugs or drugs that are perhaps gastroirritants where release can be delayed until the formulation reaches more distal regions of the gastrointestinal tract. One value of PRODAS technology lies in the inherent flexibility to formulation whereby combinations of mini tablets, each with different release rates, are incorporated into one dosage form. As well as potentially permitting controlled absorption over a specific period, this also may permit targeted delivery of drug to specific sites of absorption throughout the gastrointestinal tract. Combination products also may be possible using mini tablets formulated with different active ingredients.

DUREDAS is a bilayer tableting technology that may be used to formulate an active agent. DUREDAS was developed to provide for two different release rates, or dual release of a drug from one dosage form. The term bilayer refers to two separate direct compression events that take place during the tableting process. In an exemplary embodiment, an immediate release granulate is first compressed, being followed by the addition of a controlled release element which is then compressed onto this initial tablet. This may give rise to the characteristic bilayer seen in the final dosage form.

The controlled release properties may be provided by a combination of hydrophilic polymers. In certain cases, a rapid release of an active agent may be desirable in order to facilitate a fast onset of therapeutic affect. Hence one layer of the tablet may be formulated as an immediate-release granulate. By contrast, the second layer of the tablet may release the drug in a controlled manner, e.g., through the use of hydrophilic polymers. This controlled release may result from a combination of diffusion and erosion through the hydrophilic polymer matrix.

A further extension of DUREDAS technology is the production of controlled release combination dosage forms. In this instance, two different active agents may be incorporated into the bilayer tablet and the release of drug from each layer controlled to maximize therapeutic affect of the combination.

An active agent can be incorporated into any one of the aforementioned controlled released dosage forms, or other conventional dosage forms. The amount of active agent contained in each dose can be adjusted, to meet the needs of the individual patient, and the indication. One of skill in the art and reading this disclosure will readily recognize how to adjust the level of an active agent and the release rates in a controlled release formulation, in order to optimize delivery of an active agent and its bioavailability.

Inhalational Formulations

An active agent will in some embodiments be administered to a patient by means of a pharmaceutical delivery system for the inhalation route. The active agent may be formulated in a form suitable for administration by inhalation. The inhalational mute of administration provides the advantage that the inhaled drug can bypass the blood-brain barrier. The pharmaceutical delivery system is one that is suitable for respiratory therapy by delivery of an active agent to mucosal linings of the bronchi. This invention can utilize a system that depends on the power of a compressed gas to expel the active agent from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed in this invention, the aerosol contains the therapeutically active compound (e.g., active agent), which can be dissolved, suspended, or emulsified in a mixture of a fluid carrier and a propellant. The aerosol can be in the form of a solution, suspension, emulsion, powder, or semi-solid preparation. Aerosols employed in the present invention are intended for administration as fine, solid particles or as liquid mists via the respiratory tract of a patient. Various types of propellants known to one of skill in the art can be utilized. Suitable propellants include, but are not limited to, hydrocarbons or other suitable gas. In the case of the pressurized aerosol, the dosage unit may be determined by providing a value to deliver a metered amount.

An active agent can also be formulated for delivery with a nebulizer, which is an instrument that generates very fine liquid particles of substantially uniform size in a gas. For example, a liquid containing the active agent is dispersed as droplets. The small droplets can be carried by a current of air through an outlet tube of the nebulizer. The resulting mist penetrates into the respiratory tract of the patient.

A powder composition containing an active agent, with or without a lubricant, carrier, or propellant, can be administered to a mammal in need of therapy. This embodiment of the invention can be carried out with a conventional device for administering a powder pharmaceutical composition by inhalation. For example, a powder mixture of the compound and a suitable powder base such as lactose or starch may be presented in unit dosage form in for example capsular or cartridges, e.g. gelatin, or blister packs, from which the powder may be administered with the aid of an inhaler.

There are several different types of inhalation methodologies which can be employed in connection with the present invention. An active agent can be formulated in basically three different types of formulations for inhalation. First, an active agent can be formulated with low boiling point propellants. Such formulations are generally administered by conventional meter dose inhalers (MDI's). However, conventional MDI's can be modified so as to increase the ability to obtain repeatable dosing by utilizing technology which measures the inspiratory volume and flow rate of the patient as discussed within U.S. Pat. Nos. 5,404,871 and 5,542,410.

Alternatively, an active agent can be formulated in aqueous or ethanolic solutions and delivered by conventional nebulizers. In some embodiments, such solution formulations are aerosolized using devices and systems such as disclosed within U.S. Pat. Nos. 5,497,763; 5,544,646; 5,718,222; and 5,660,166.

An active agent can be formulated into dry powder formulations. Such formulations can be administered by simply inhaling the dry powder formulation after creating an aerosol mist of the powder. Technology for carrying such out is described within U.S. Pat. Nos. 5,775,320 and 5,740,794.

Dosages

Although the dosage used will vary depending on the clinical goals to be achieved, a suitable dosage range is one which provides up to about 1 μg to about 1,000 μg or about 10,000 μg of an agent that blocks a TGF-β pathway can be administered in a single dose. For example, a single dose of an active agent can include from about 1 μg to about 10 g, from about 10 μg to about 25 μg, from about 25 μg to about 50 μg, from about 50 μg to about 100 μg, from about 100 μg to about 500 μg, from about 500 μg to about 1 mg, from about 1 mg to about 5 mg, or from about 5 mg to about 10 mg, of active agent in a single dose. Alternatively, a target dosage of agent that blocks a TGF-β pathway can be considered to be about in the range of about 0.1-1000 μM, about 0.5-500 μM, about 1-100 μM, or about 5-50 μM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, multiple doses of an active agent are administered. The frequency of administration of an active agent can vary depending on any of a variety of factors, e.g., severity of the symptoms, etc. For example, in some embodiments, an active agent is administered once per month, twice per month, three times per month, every other week (qow), once per week (qw), twice per week (biw), three times per week (tiw), tour times per week, five times per week, six times per week, every other day (qod), daily (qd), twice a day (qid), or three times a day (tid). In some embodiments, an active agent is administered continuously.

The duration of administration of an active agent, e.g., the period of time over which an active agent is administered, can vary, depending on any of a variety of factors, e.g., patient response, etc. For example, an active agent can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In some embodiments, an agent that blocks a TGF-β pathway is administered for the lifetime of the individual.

In some embodiments, administration of an active agent is discontinuous, e.g., an active agent is administered for a first period of time and at a first dosing frequency; administration of the active agent is suspended for a period of time; then the active agent is administered for a second period of time for a second dosing frequency. The period of time during which administration of the active agent is suspended can vary depending on various factors, e.g., cognitive functions of the individual; and will generally range from about 1 week to about 6 months, e.g., from about 1 week to about 2 weeks, from about 2 weeks to about 4 weeks, from about one month to about 2 months, from about 2 months to about 4 months, or from about 4 months to about 6 months, or longer. The first period of time may be the same or different than the second period of time; and the first dosing frequency may be the same or different than the second dosing frequency.

Routes of Administration

An agent that blocks a TGF-β pathway is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

The agent can be administered to a host using any available conventional methods and mutes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intracranial, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral mutes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

In some embodiments, an active agent is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present invention. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of active agent can be accomplished using any of a variety of refillable, pump systems. Pumps provide consistent, controlled release over time. In some embodiments, the agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to a subdermal, subcutaneous, intramuscular, or other suitable site within a subject's body. Subcutaneous implantation sites are used in some embodiments because of convenience in implantation and removal of the drug delivery device.

Drug release devices suitable for use in the invention may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present invention. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396)). Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5.728396; and the like.

In some embodiments, the drug delivery device is an implantable device. The drug delivery device can be implanted at any suitable implantation site using methods and devices well known in the art. As noted infra, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent is delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present invention is the Synchromed infusion pump (Medtronic).

Crossing the Blood-Brain Barrier

The blood-brain barrier limits the uptake of many therapeutic agents into the brain and spinal cord from the general circulation. Molecules which cross the blood-brain barrier use two main mechanisms: free diffusion; and facilitated transport. Because of the presence of the blood-brain barrier, attaining beneficial concentrations of a given therapeutic agent in the central nervous system (CNS) may require the use of drug delivery strategies. Delivery of therapeutic agents to the CNS can be achieved by several methods.

One method relies on neurosurgical techniques. In the case of gravely ill patients such as accident victims or those suffering from various forms of dementia, surgical intervention is warranted despite its attendant risks. For instance, therapeutic agents can be delivered by direct physical introduction into the CNS, such as intraventricular or intrathecal injection of drugs. Intraventricular injection may be facilitated by an intraventricular catheter, for example, attached to a reservoir, such as an Ommaya reservoir. Methods of introduction may also be provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents such as leukotrienes. Neuwelt and Rappoport (1984) *Fed. Proc.* 43:214-219; Baba et al. (1991) *J. Cereb. Blood Flow Metab.* 11:638-643; and Gennuso et al. 1993) *Cancer Invest.* 11:638-643.

Further, it may be desirable to administer the pharmaceutical agents locally to the area in need of treatment; this may be achieved by, for example, local infusion during surgery, by injection, by means of a catheter, or by means of an implant, said implant being of a porous, non-porous, or gelatinous material, including membranes, such as silastic membranes, or fibers.

Therapeutic compounds can also be delivered by using pharmacological techniques including chemical modification or screening for an analog which will cross the blood-brain barrier. The compound may be modified to increase the hydrophobicity of the molecule, decrease net charge or molecular weight of the molecule, or modify the molecule, so that it will resemble one normally transported across the blood-brain barrier. Levin (1980) *J. Med. Chem.* 23:682-684; Pardridge (1991) in: *Peptide Drug Delivery to the Brain*; and Kostis et al. (1994) *J. Clin. Pharmacol.* 34:989-996.

Encapsulation of the drug in a hydrophobic environment such as liposomes is also effective in delivering drugs to the CNS. For example WO 91)/4014 describes a liposomal delivery system in which the drug is encapsulated within liposomes to which molecules have been added that are normally transported across the blood-brain barrier.

Another method of formulating the drug to pass through the blood-brain barrier is to encapsulate the drug in a cyclodextrin. Any suitable cyclodextrin which passes through the blood-brain barrier may be employed, including, but not limited to, α-cyclodextrin, β-cyclodextrin and derivatives thereof. See generally, U.S. Pat. Nos. 5,017,566, 5,002,935 and 4,983,586. Such compositions may also include a glycerol derivative as described by U.S. Pat. No. 5,153,179.

Delivery may also be obtained by conjugation of a therapeutic agent to a transportable agent to yield a new chimeric transportable therapeutic agent. For example, vasoactive intestinal peptide analog (VIPa) exerted its vasoactive effects only after conjugation to a monoclonal antibody (Mab) to the specific carrier molecule transferrin receptor, which facilitated the uptake of the VIPa-Mab conjugate through the blood-brain barrier. Pardridge (1991); and Bickel et al. (1993) *Proc. Natl. Acad Sci. USA* 90:2618-2622. Several other specific transport systems have been identified, these include, but are not limited to, those for transferring insulin, or insulin-like growth factors I and II. Other suitable., non-specific carriers include, but are not limited to, pyridinium, fatty acids, inositol, cholesterol, and glucose derivatives. Certain prodrugs have been described whereby, upon entering the central nervous system, the drug is cleaved from the carrier to release the active drug. U.S. Pat. No. 5,017,566.

Examples of methods of crossing the BBB include: use of vasoactive substances such as bradykinin or a bradykinin analog (where bradykinin analogs include, e.g., [Phe$^8$ψ(CH$_2$—NH)Arg$^9$]-bradykinin, N-acetyl-[Phe$^8$ψ(CH$_2$—NH)Arg$^9$]-bradykinin, desArg$^9$-bradykinin, etc.); use of nitric oxide (NO) donor drugs (see below); localized exposure to high-intensity focused ultrasound; use of endogenous transport systems, including carrier-mediated transporters such as glucose and amino acid carriers; use of liposomes loaded with nanoparticles containing an active agent, where an example of such a nanoparticle is a polyethylene glycol-coated hexadecylcyanoacrylate nanosphere (see, e.g., Silva (2008) *BMC Neurosci.* 9:S4; Brigger et al. (2002) *J. Pharm. Exp. Ther.* 303:928; Wong et al. (2(009) *Adv. Drug Del. Rev.* PMID 19914319; Khalil and Mainardes (2009) *Curr. Drug. Del.* 6:261; Modi et al. (2009) *Prog. Neurobiol.* 88:272; Barbu et al. (2009) *Expert Opin. Drug. Del.* 6:553); use of agents (e.g., Tariquidar) that inhibit P-glycoprotein at the BBB; and the like.

Suitable NO donor drugs include, e.g., organic nitrate compounds which are nitric acid esters of mono- and polyhydric alcohols, (e.g., glyceryl trinitrate (GTN) or nitroglycerin (NTG), pentaerythrityl tetranitrate (PETN), isosorbide dinitrate (ISDN), and isosorbide 5-mononitrate (IS-5-N)), S-nitrosothiol compounds (e.g., S-nitroso-N-acetyl-D, L-penicillanine (SNAP), S-nitrosoglutathione (SNOG), S-nitrosoalbumin, S-nitrosocysteine), sydnonimine compounds (e.g., molsidomine (N-ethoxycarbonyl-3-morpholino-sydnoninine), linsidomine (e.g., SIN-1; 3-morpholino-sydnoninmine or 3-morpholinylsydnoneimine or 5-amino-3-morpholinyl-1,2,3-oxadiazolium), and pirsidomine (CAS 936).

In other embodiments, an active agent conjugated to a targeting domain to form a chimeric therapeutic, where the targeting domain facilitates passage of the blood-brain barrier (as described above) and/or binds one or more molecular targets in the CNS. In some embodiments, the targeting domain binds a target that is differentially expressed or displayed on, or in close proximity to, tissues, organs, and/or cells of interest. In some cases, the target is preferentially distributed in a neurogenic region of the brain, such as the dentate gyrus and/or the SVZ. For example, in some embodiments, an active agent is conjugated or complexed with the fatty acid docosahexaenoic acid (DHA), which is readily transported across the blood brain barrier and imported into cells of the CNS.

Combination Therapies

A TGF-β pathway inhibitor (e.g., an agent that blocks a TGF-β pathway) can be administered in monotherapy, e.g., a single TGF-β pathway inhibitor is administered in the absence of administration of any other therapeutic agent for the treatment of the epilepsy or the neurodegenerative disorder. Alternatively, a TGF-β pathway inhibitor (e.g., an agent that blocks a TGF-β pathway) can be administered in combination therapy with one or more additional therapeutic agents.

For example, in the treatment of epilepsy, a TGF-β pathway inhibitor can be administered to an individual in combination therapy with one or more additional therapeutic agents for the treatment of epilepsy. Therapeutic agents that are suitable for administration in combination therapy with a TGF-β pathway inhibitor include, but are not limited to, Carbanmazepine, Carbatrol®, Clobazam, Depakene®, Depakote®, Diastat, Dilantin®, Ethosuximide, Felbatol®, Felbamate, Frisium, Gabapentin, Gabitril®, Inovelon®, Luminal, Lyrica, Mysoline®, Neurontin®, Oxcarbazepine, Phenobarbital, Phenytek®, Phenytoin, Primidone, Rufinamde, Sabril Tegretol®, Tegretol XR®, Tiagabine, Topamax®. Topiraniate, Keppra®, Keppra XR™, Klonopin, Lmaictal®, Lamotrigine, Levetiracetam, Trileptal®, Valproic Acid, Zarontin®, Zonegran®, and Zonisamide.

As another example, in the treatment of Alzheimer's Disease (AD), a TGF-β pathway inhibitor can be administered to an individual in combination therapy with one or more additional therapeutic agents for the treatment of AD. Suitable additional therapeutic agents include, but are not limited to, acetylcholinesterase inhibitors, including, but not limited to, Aricept (donepezil), Exelon (rivastigmine), metrifonate, and tacrine (Cognex); non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art. For example, Aricept is generally administered at 50 mg orally per day for 6 weeks, and, if well tolerated by the individual, at 10 mg per day thereafter.

As another example, in the treatment of stroke, a TGF-β pathway inhibitor can be administered to an individual in combination therapy with one or more additional therapeutic agents for the treatment of stroke. For example, a TGF-β pathway inhibitor can be administered to an individual in combination therapy with tissue plasminogen activator.

Subjects Suitable for Treatment

Individuals who are suitable for treatment with a TGF-β inhibitor pathway include individuals who have been diagnosed with epilepsy; individuals who have suffered a stroke; individuals who have suffered traumatic head injury; individuals who have suffered brain infection (i.e. viral or bacterial encephalitis) and individuals having a neurodegenerative disorder or neurological symptoms due to diseases of small blood vessels (vasculitis, diabetes mellitus).

Subjects suitable for treatment with a subject method include individuals having one or more of the following disorders: epilepsy, traumatic brain injury, stroke, brain infection (i.e. viral or bacterial encephalitis) and neurodegenerative diseases (including that resulted from a small vessel disease, e.g. diabetes mellitus). A subject method is suitable for treating epilepsy (including posttraumatic epilepsy), Parkinson's disease, psychosis, migraine, cerebral ischemia, Alzheimer's disease and other degenerative diseases such as Huntington's chorea, schizophrenia, obsessive compulsive disorders (OCD), neurological deficits associated with acquired immunodeficiency syndrome, traumatic brain injury, inappropriate neuronal activity resulting in neurodysthesias in diseases such as diabetes, multiple sclerosis (MS) and motor neuron disease, ataxias, muscular rigidity (spasticity), temporomandibular joint dysfunction, and amyotrophic lateral sclerosis (ALS).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pI, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: TGF-β Signaling in Epileptogenesis

Experimental Procedures
In Vivo Preparation:
All experimental procedures were approved by the ethical committees dealing with experiments on animals at Charité University Medicine, Berlin and Ben-Gurion University of the Negev, Beer-Sheva. The in vivo experiments were performed as previously described (ivens et al., 2007; Seiffert et al., 2004). Adult male Wistar rats were treated with artificial cerebrospinal fluid (aCSF, composition in mM: 129 NaCl, 21 NaHCO3, 1.25 NaH2PO4, 1.8 MgSO4, 1.6 CaCl2, 3 KCl, 10 glucose) supplemented with deoxycholic acid (DOC, 2 mM, Sigma-Aldrich, Steinheim, Germany), bovine serum albumin (BSA, 0.1 mM. Merck, Darmstadt, Germany) corresponding to 25% of serum albumin concentration, or with TGF-β1 (10 ng/ml, Peprotech, Rocky Hill, N.J.). Sham-operated animals (perfused with aCSF) served as controls. Only rats with no apparent injury to the cortical surface or bleeding from cortical vessels (as seen under the surgical microscope) at the end of the procedure were used. Animals were sacrificed 7/8, 24, or 48 hours following treatment. A second set of animals including sham-operated controls and animals treated with BSA or BSA plus TGF-βR blockers (TGF-βRII antibody, 50 μg/ml, Santa Cruz Biotechnology, Santa Cruz, Calif.; SB431542, 100 μM, Tocris. Bristol, UK) were sacrificed 24 hours following treatment. For Smad2-P immunodetection, animals were treated with 0.2 mM BSA and sacrificed 46-50 hours following treatment.

In Vitro Slice Preparation:
Brain slices for the in vitro experiments were prepared by means of standard techniques (Ivens et al., 2007; Pavlovsky et al., 2003; Seiffert et al., 2004). Slices were transferred to a recording chamber where they were incubated in aCSF containing BSA (6.7 mg/ml), TGF-β1 (10 ng/ml) or artificial serum (aSerum, composition based on aCSF with the following changes, composition in mM: 0.8 MgSO4, 1.3 CaCl2, 5.7 KCl, 1 L-glutamine, 0.1 albumin). To block the activity of TGF-β1, slices were incubated in aCSF containing SB431542 (10 μM) before the addition of TGF-β1 (10 ng/ml). To block TGF-βRs, slices were incubated in aCSF containing SB431542 (10 μM) and TGF-βRII antibody (10 μg/ml) for 30 min followed by incubation in BSA in the presence of TGF-βR blockers. For detection of epileptiform activity, field potentials were recorded >4 h following incubation in cortical layer IV using extracellular glass microelectrodes (~3 MΩ) in response to bipolar stimulation at the border of white and grey matter.

Albumin and TGF-βRII Co-Immunoprecipitation:
To prepare cortical lysates, brains were isolated from adult Wistar rats, dissected in cold saline solution and lysed in RIPA buffer. BSA (3 μg) was added to lysates to approximately match the amount of precipitating anti-albumin antibodies. Immunoprecipitation was performed using the Catch and Release® v2.0 Reversible Immunoprecipitation System (Upstate, Charlottesville, Va.) with the following modifications to the standard protocol: the starting amount of protein was increased to 1,500 μg and the incubation time with precipitating antibodies was increased to 90 minutes. Lysate samples (positive or negative for albumin) were immunoprecipitated with an anti-TGF-βRII antibody (Upstate) or an anti-albumin antibody (Biogenesis, Poole, UK).

The immunoprecipitated samples were separated with SDS-PAGE and transferred onto a nitrocellulose membrane. The membrane was stained with Ponceau S stain to confirm that the IP procedure was successful. It was then destained, and blocked with 5% BSA in standard TBS-T buffer overnight at 4° C. TGF-βRII was detected with a rabbit anti-TGF-βRII antibody (Upstate) and an AP-conjugated donkey anti-rabbit IgG secondary antibody (Jackson ImmunoResearch Laboratories, West Grove, Pa.). Chemiluminescent detection was done using Lumi-Phos WB Chemiluminescent Substrate (Pierce, Rockfort, Ill.) and standard X-ray film according to the manufacturer's instructions.

Smad2-P Western Blot Analysis:
Cortical lysate samples from sham-operated controls and animals treated with BSA were separated by SDS-PAGE and transferred onto a nitrocellulose membrane. The membrane was blocked with 5% nonfat milk overnight at 4° C., incubated with a rabbit polyclonal antibody against phospho-Smad2 (Millipore Corporation, Bedford, Mass.) for 48 hr at 4° C., and incubated with a peroxidase-conjugated goat anti-rabbit IgG secondary antibody (Jackson ImmunoResearch Laboratories) for 2 hr at room temperature.

Microarrays:
Total RNA was isolated using the TRIzol reagent (Invitrogen. Carlsbad, Calif.) and prepared using the Affymetrix GeneChip one-cycle target labeling kit (Affymetrix, Santa Clara, Calif.). Biotinylated cRNA was fragmented and hybridized to the GeneChip Rat Genome 230 2.0 Array according to company protocols (Affymetrix Technical Manual). Normalization of the array data was done using GCRMA (GC Robust Multi-Array Average) analysis. Functional annotation analysis was performed with the program Database for Annotation, Visualization, and Integrated Discovery (DAVID) 2008 (Dennis et al., 2003) (http:(double forward slash)david(dot)abcc(dot)nciferf(dot)gov). The GenMAPP 2.0 program (Salomonis et al., 2007) (http://www.genmapp.org/) was used to visualize genes involved in TGF-β signaling. For the time course analysis one array was run for each treatment (DOC, BSA, TGF-β1) for the following time points: 7/8, 24, and 48 hr. In addition a sample from a sham treated animal (24 hr) was run and used to normalize the other arrays. Pairwise Pearson correlation coefficients for the three treatments were determined with Excel (Microsoft Corp., Richmond, Wash.). Hierarchical clustering was performed with Gene Cluster and displayed with TreeView software (Eisen et al., 1998). Arrays were then run for the second set of animals sacrificed 24 hr following treatment (Sham, n=2; BSA, n=3; BSA+TGF-βR blockers, n=4). Significance analysis of microarrays (SAM) was performed with a false discovery rate (FDR) threshold of 9.2%. A 1.5 fold change cutoff was also used to filter this list. Genes which demonstrated a significant change in expression following albumin treatment and a log 2 ratio difference >0.5 between the two treatments were considered part of the attenuated response. Genes demonstrating a significant change in expression following albumin and albumin plus blocker treatments were considered part of the unattenuated response. All microarray data are available at the GEO website (http://www.ncbi.nlm.nih.gov/geo) under accession number GSE12304.

Real-Time RT-PCR:

mRNA expression levels were determined by quantitative reverse transcriptase-PCR by real-time kinetic analysis with an iQ5 detection system (Bio-Rad, Hercules, Calif.). Real-time PCR data were analyzed using the PCR Miner program (Zhao and Fernald, 2005). 18S mRNA levels were used as internal controls for variations in sample preparation. Primer sequences are provided in supplementary methods.

Statistical Analyses:

For the electrophysiological data, differences between treated and control slices were determined by the Mann-Whitney U test for two independent samples or the chi-square test using SPSS 13.0 (SPSS Inc., Chicago, Ill.). Linear regression analysis for the microarray data was performed with Graphpad Prism (GraphPad Software, Inc., San Diego, Calif.). PCR data were analyzed with an unpaired Student's t test ($p<0.05$ was considered significant) in Excel (Microsoft) or with the relative expression software tool (REST) (Pfaffl, 2001). REST determines significance of the group ratio results with a randomization test. $p<0.05$ was taken as the level of statistical significance.

Results

TGF-β Signaling is Sufficient to Induce Epileptiform Activity

Figure 1C:
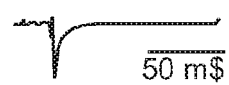
Figure 1C:
Figure 1B:
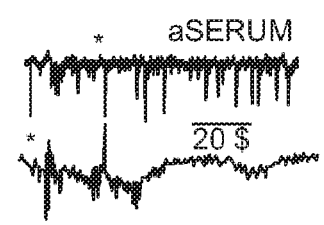
Figure 1B:
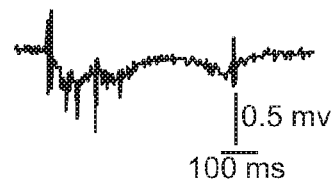
Figure 1B:

To assess the hypothesis that activation of the TGF-β signaling pathway is the mechanism underlying albumin-induced epileptogenesis, we activated this pathway directly by incubating neocortical slices with TGF-β1 (10 ng/mL) in artificial cerebrospinal fluid (aCSF) and performed electrophysiological recordings. These recordings were compared to those of slices treated with a solution containing serum levels of electrolytes and 0.1 mM albumin (aSERUM, previously shown to induce epileptogenesis; Ivens et al., 2007), albumin in aCSF, or aCSF (control). Spontaneous, prolonged and hypersynchronous interictal-like activity was observed in slices treated with aSERUM for 6-10 hours (n=6 out of 9 slices, 3 animals) but never in aCSF treated slices (FIG. 1b). When albumin was added to the control aCSF solution, epileptiform activity was recorded in response to stimulation of the white matter (n=8 out of 12 slices, 6 animals). Importantly, TGF-β1 treatment was sufficient to recapitulate epileptiform activity similar to that seen following treatment with aSERUM and albumin in aCSF (n=5 out of 5 slices, 4 animals; n=7 out of 9 slices, 3 animals; and n=8 out of 12 slices, 6 animals, respectively). In all three cases, the evoked epileptiform activity, was all-or-none in nature, paroxysmal and prolonged, similar to that seen following BBB opening with bile salts (Ivens et al., 2007; Seiffert et al., 2004) and typical to that observed in acute models of epilepsy (Gutnick et al., 1982). No activity was seen in the aCSF control treated slices.

Figure 1D:
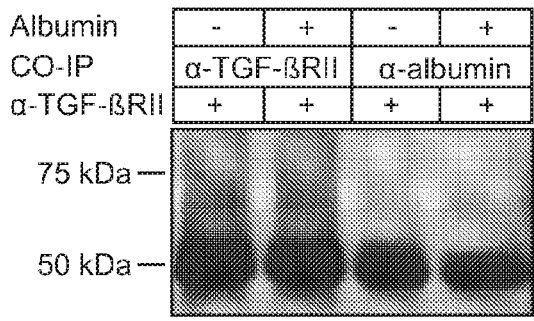
Figure 1E:
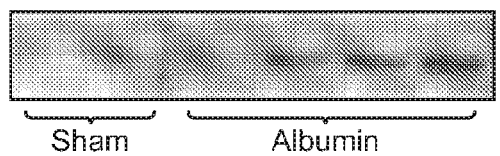

To further confirm that the TGF-β1 induced epileptiform activity was dependent on the TGF-βR mediated pathway, we performed additional trials of the above experiments in the presence of two TGF-βR blockers (SB431542, the TGF-βRI kinase activity inhibitor and TGF-βRII antibody). TGF-βR blockers prevented epileptiform activity induced by TGF-01 or albumin (FIG. 1c). The measured integral of the field potential (albumin: 117.2±35.4 mV*ms; TGF-β1: 84.1±20.1 mV*ms) was significantly lower in slices treated with albumin or TGF-β1 in the presence of TGF-βR blockers (albumin and blockers: 23.7±6.9 mV*ms, n=20 slices, 4 animals, p=0.001; TGF-β1 and blockers: 12.5±3.9 mV*ms, n=8 slices, 4 animals, p=0.005) (FIG. 1d).

Albumin Binds TGF-βRs and Activates the TGF-β Pathway

Figure 2B:
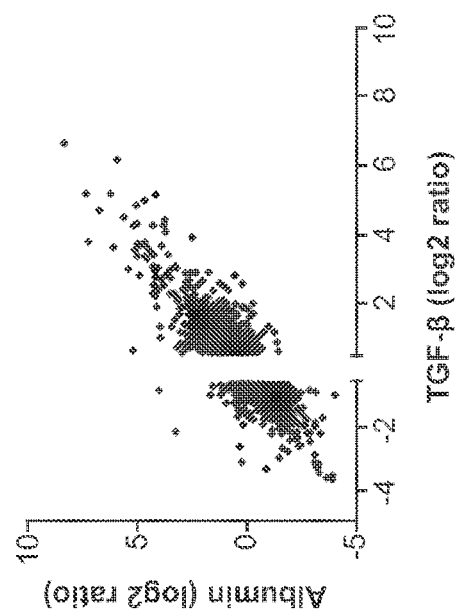
FIGS. 2A-C depict genome wide transcriptional analysis following epileptogenic treatments.
Figure 2A:
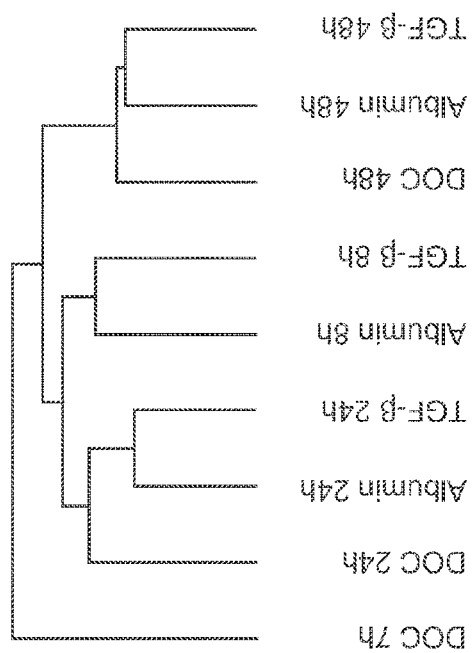
Figure 2C:
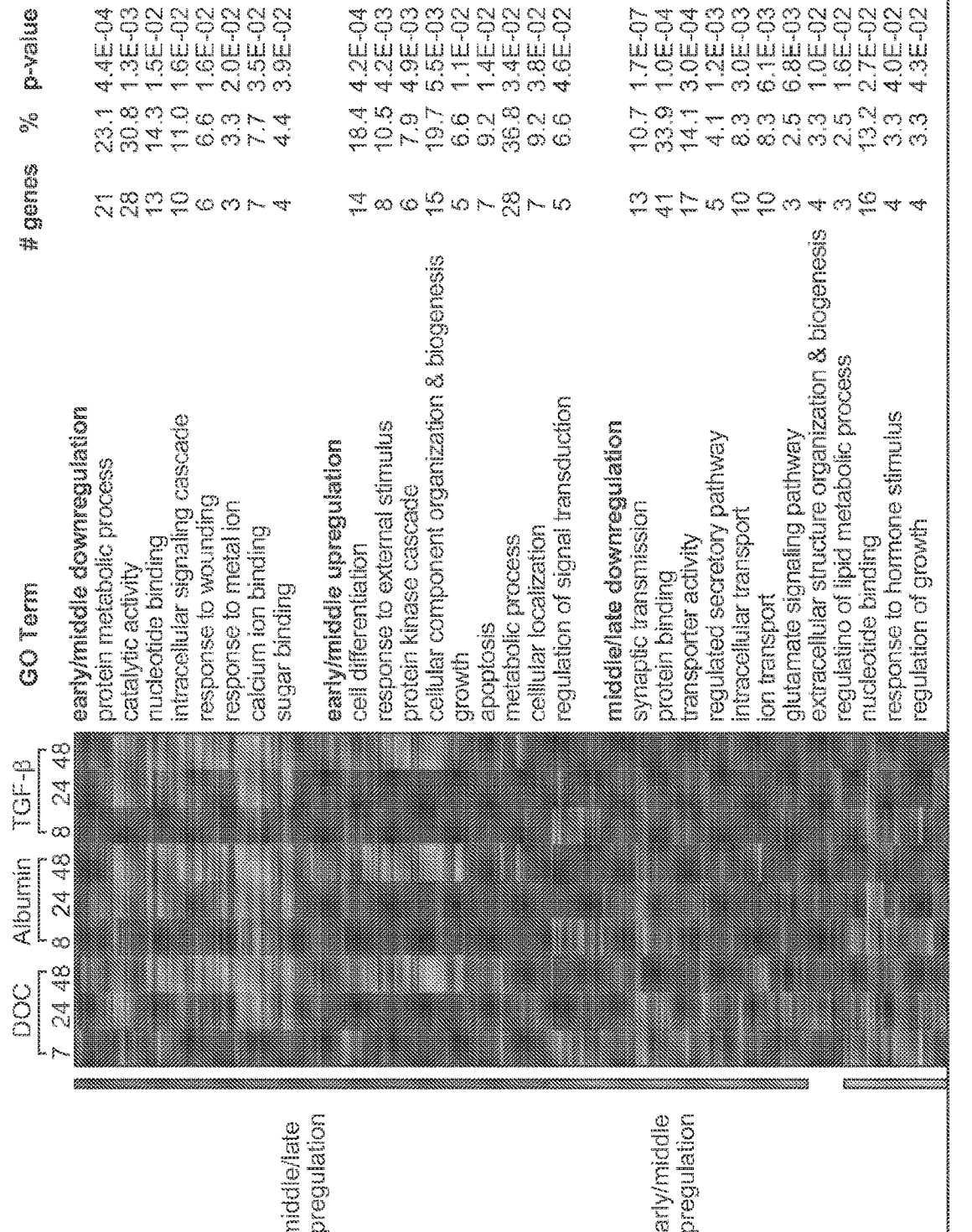
Figure 2C:
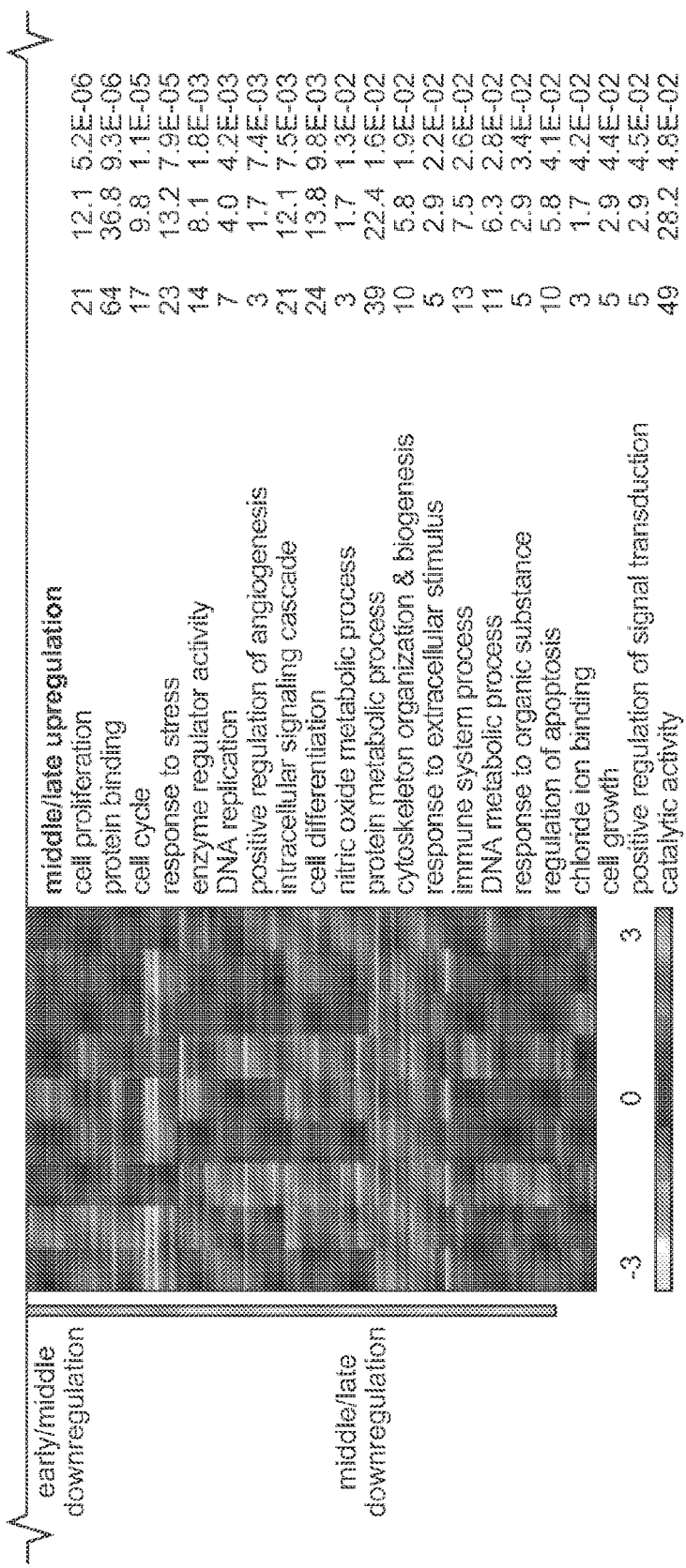
Figure 4A:
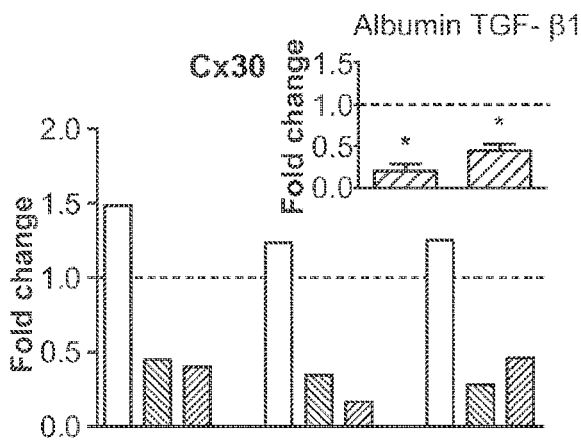
FIG. 4A-F depicts qRT-CR gene expression analysis.
Figure 4B:
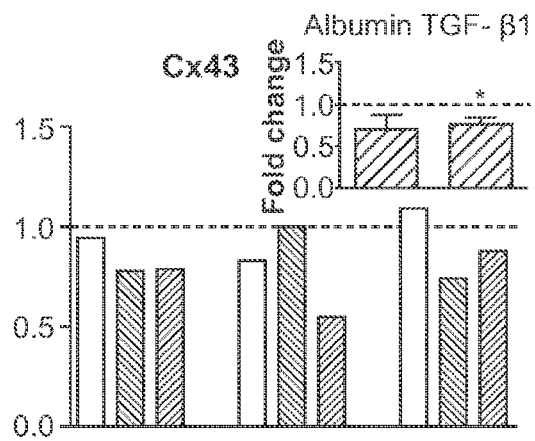
Figure 4C:
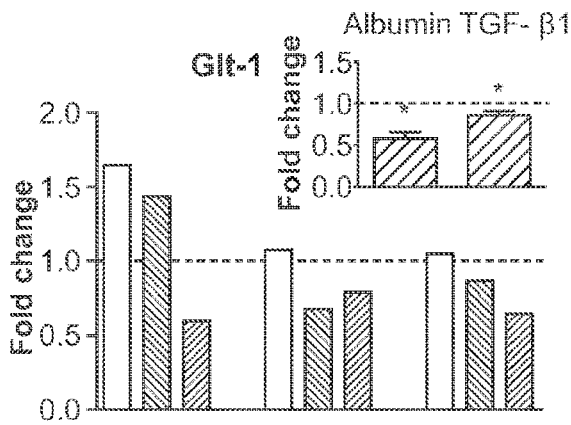
Figure 4D:
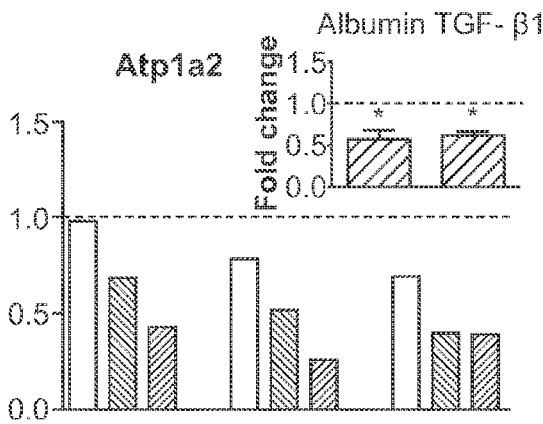
Figure 4E:
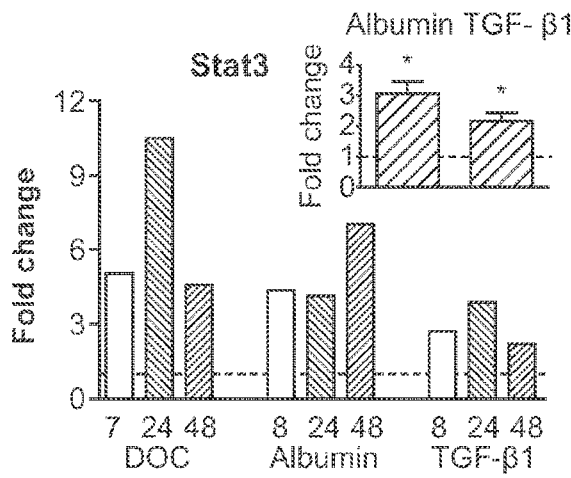
Figure 4F:
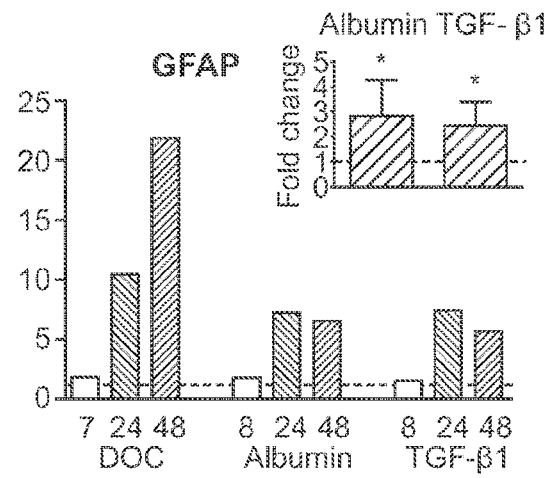

To determine whether albumin binds to TGF-β receptors, co-immunoprecipitation using antibodies against albumin or TGF-βRII was performed on cortical lysate samples treated with albumin. An expected band corresponding to TGF-βRII was detected in samples immunoprecipitated with the TGF-βRII antibody. More importantly, this band was also detected in samples pre-incubated with albumin when immunoprecipitated with the albumin antibody and probed for TGF-βRII (FIG. 2a). These results reveal a direct interaction between albumin and TGF-βRII. In the canonical TGF-β signaling pathway, Smad2 and/or 3 are phosphorylated following TGF-β receptor activation and form a complex with Smad4, which then translocates into the nucleus and activates transcription (Shi and Massague, 2003). To investigate whether albumin activates downstream components of the TGF-β pathway, Smad2 phosphorylation levels in cortical lysates were assessed by Western blot, revealing an increase in Smad2 phosphorylation in animals exposed to albumin for 48 hours as compared to sham-operated controls (FIG. 2b).

Similar Transcriptional Profiles Follow BBB Opening, Albumin and TGF-β1 Treatments BBB opening or exposure to albumin in vivo (Ivens et al., 2007), as well as in vitro exposure of neocortical slices to albumin or TGF-β1 (FIG. 1c) all result in the gradual development of hypersynchronous neuronal epileptiform activity. The delayed appearance of abnormal activity (5-7 hours in vitro and >4 days in vivo, data not shown (Ivens et al., 2007)) suggests a transcription-mediated mechanism. In search of a common pathway and transcriptional activation pattern that underlie epileptogenesis following BBB opening, we performed transcriptome analysis using Affymetrix rat microarrays. RNA was extracted from cortical regions of rats treated with sodium deoxycholate (DOC, to induce BBB opening), albumin or TGF-β1 for various durations (7/8, 24, 48 hr). Control RNA was extracted from cortical regions excised from sham-operated animals. Hierarchical clustering analysis of these arrays showed that overall the three treatments resulted in strikingly similar gene expression changes, as arrays representing similar time points clustered together regardless of the treatment (FIG. 3a)., These similarities are exemplified in FIG. 3b, which shows a high correlation between the expression profiles for the albumin and TGF-β 1 treatments at 24 hours ($r^2=0.75$, $p<0.0001$).

To identify biological themes common to the three treatments, the gene list was filtered to include genes showing at least a 1.5 fold change in expression and a Pearson correlation coefficient ≥0.95 for pair-wise comparisons between all treatments (see methods). Hierarchical clustering was performed and the main clusters were used for gene ontology (GO) analysis with DAVID (Database for Annotation, Visualization, and Integrated Discovery; Dennis et al., 2003). Molecular function and biological process GO terms with a p-value <0.05 containing at least three genes were considered significant. This analysis reveals major gene expression trends that occur in response to all three epileptogenic treatments (FIG. 3c). Early responses include genes involved in general stress-related cellular, metabolic and intracellular signaling pathways; early responses persisting to later time points include inflammatory processes as well as genes involved in induction of cell cycle, differentiation, proliferation, and apoptosis; responses at middle to late time points include repression of synaptic transmission and ion transport genes (FIG. 3c).

Gene Level Expression Profiles

Selected GO term groups were chosen for further analysis of individual gene expression profiles (FIG. 4). The most dramatic change observed in all treatments across all time points was the early and persistent upregulation of genes associated with immune response activation, including inflammatory NF-kappa B pathway related genes, cytokines and chemokines (FIG. 4a), and complement pathway genes (FIG. 4b). A significant neuronal response was prominent in the middle-late time points and included downregulation of genes associated with GABAergic (inhibitory) neurotransmission (FIG. 4c) and modulation of genes associated with glutamatergic (excitatory) neurotransmission again (FIG. 4d). Furthermore, a variety of voltage gated ion channels including calcium, sodium, chloride, and potassium channels were affected by all three epileptogenic treatments (FIG. 4e), including a noteworthy downregulation of voltage gated (Kv7.3 and Kv8.1) and inward rectifying (Kir3.1) potassium channels. We also found significant modulation of glial-specific genes beginning in the early time point (FIG. 4f): the cytoskeletal proteins GFAP and vimentin (Vim), and several calcium binding proteins (S100a6, S100a10, s100a11) were all upregulated while gap junction connexins 30 and 43 (Cx30 and Cx43) and the inward rectifying potassium channel Kir4.1 were downregulated. Microarray-based gene expression measurements for selected genes were further verified using quantitative real-time PCR. Expression patterns were similar although the magnitude of the fold changes sometimes differed.

TGF-β Pathway Activation is Required for Transcriptional Changes

Given the high correlation between expression profiles following the three epileptogenic treatments, combined with the biochemical evidence that albumin hinds to TGF-β receptors and the physiological evidence that TGF-β treatment induces epileptogenesis, we assessed the extent to which each treatment activates transcription of genes known to be associated with the TGF-β signaling pathway using GenMAPP (Saloomis et al., 2007). Genes which showed at least a 1.5 fold change in expression following albumin or TGF-β1 treatment, are highlighted in FIG. 5, demonstrating that 86% of genes modulated by TGF-β1 treatment are also modulated following albumin treatment.

The above evidence indicates that TGF-β signaling is a key mediator of albumin-induced epileptogenesis. To determine if the global transcriptional response seen following albumin treatment is dependent on activation of the TGF-β signaling pathway, we performed an additional set of microarray expression profiles using rats treated with albumin in the absence (n=3) or presence of TGF-βRI and II blockers (n-=4, TGF-βR1 kinase activity inhibitor SB431542 and anti-TGF-β RII antibody) and sacrificed 24 hours following treatment. Although some changes in gene expression resulting from albumin treatment were still present following the blocker treatment, the majority of these changes were absent or attenuated following TGF-β pathway blocker treatment (FIG. 6a), confirming dependence of the albumin-induced transcriptional response on TGF-β signaling.

Figure 6A:
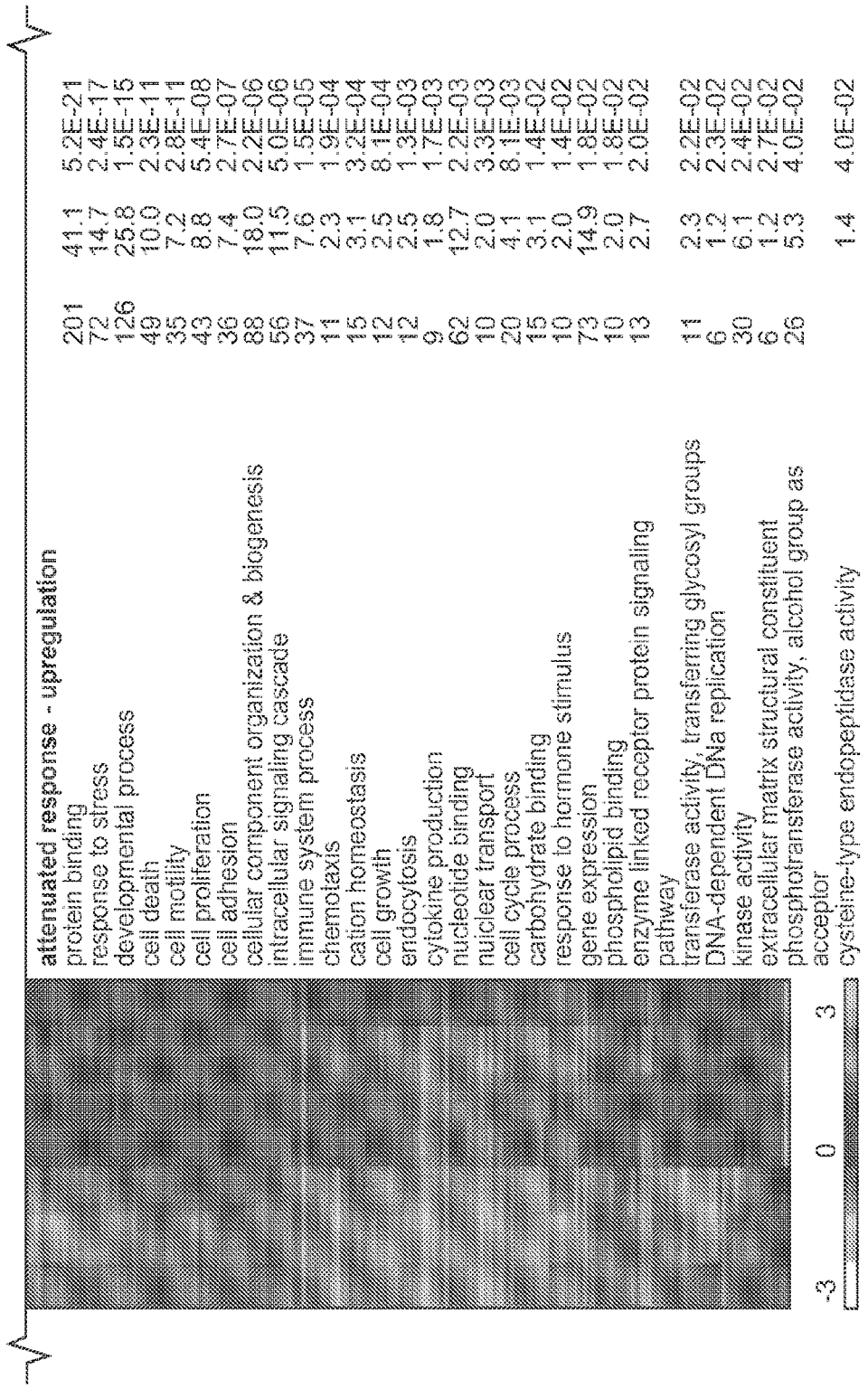

Gene ontology analysis was then used to reveal which biological processes were blocked following TGF-β pathway blocker treatment (FIG. 6a) Genes in the TGF-β signaling GO term demonstrated a dramatic suppression of the albumin-induced expression changes in the presence of TGF-β3 signaling blockers (FIG. 6b). In addition, TGF-β pathway blocker treatment prevented the albumin-induced modulation of genes involved in neuronal processes, immune response, and ion and cellular transport (FIG. 6h). Several prominent signaling pathways including the NF-kappaB cascade, Jak-Stat cascade, and MAPKKK cascade were upregulated following albumin treatment, but did not show a similar upregulation following albumin treatment in the presence of TGF-β pathway blockers. Quantitative real-time PCR was also performed with these samples to confirm the microarray results (FIG. 6c). Indeed, TGF-β pathway blocker treatment completely blocked expression changes following albumin exposure for Stat3 and Glt-1 and partially blocked changes for Cx43 and GFAP.

FIGS. 1-6

FIG. 1: Epileptiform Activity and TGF-β Pathway Activation are Induced by Serum Albumin.

(A) Photograph of a brain slice displaying electrode positioning. (B) Extracellular recordings showing spontaneous interictal-like epileptiform activity following treatment with artificial serum containing albumin (aSERUM). (C) Evoked responses from slices treated with aCSF, albumin or TGF-β1 in aCSF, or albumin in artificial serum (aSERUM). (D) Albumin and TGF-βRII immunoprecipitations. Samples treated or untreated with serum albumin were co-immunoprecipitated with antibodies directed against albumin or the TGF-β RII receptor. All samples were then probed with an anti-TGF-βRII antibody. The band at 50 kDa is the heavy chain of the precipitating antibody. (E) Western blot analysis of Smad2-P following albumin treatment.

FIG. 2: Genome Wide Transcriptional Analysis Following Epileptogenic Treatments.

(A) Hierarchical clustering of arrays corresponding to 7/8, 24 and 48 hours following DOC, albumin and TGF-β1 treatments. Note how arrays cluster together for each time point across all treatments. (B) Linear regression analysis between TGF-β1 and albumin treatments at 24 hours. Only genes with a fold change equal to or greater than 1.5 for the TGF-β1 treatment were included. (C) Hierarchical cluster analysis of genes showing correlation (>0.95) between all treatments. Selected clusters were annotated with DAVID to reveal biological themes common to all treatments. Color bar indicates range of $\log_2$ ratios.

FIG. 3: Gene Ontology (GO) Annotation Analysis.

$\log_2$ ratios for selected genes from (GO annotation analysis involved in (A) inflammation, (B) complement activation, (C) GABAergic transmission, (D) glutamatergic transmission, (E) voltage gated ion channels, and (F) Astrocytic-related genes. Numbers below data points correspond to the various treatments (7/8, 24, and 48 hours).

FIG. 4: qRT-PCR Gene Expression Analysis.

Time course analysis for selected genes following treatment with DOC, albumin or TGF-β 1 at 7/8, 24 or 48 hr. Data are expressed as fold changes relative to sham treated controls. Significance of changes was assessed for the 24 hour time point (shown in insets for albumin (n=3) and TGF-β1 (n=3) treatments; error bars indicate s.e.m. asterisks indicate $p<0.05$).

Figure 5:
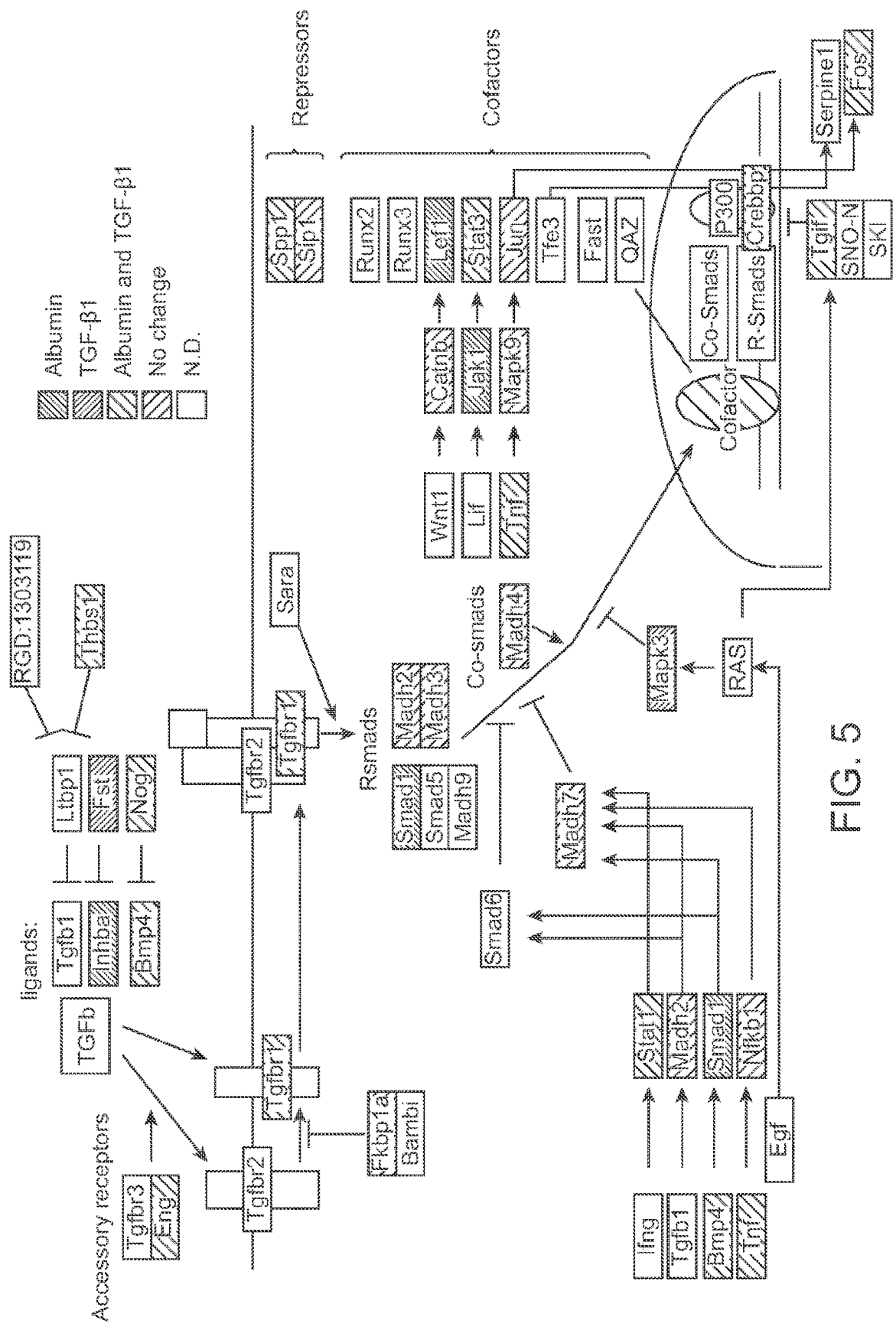
FIG. 5 depicts the effect of albumin on TGF-β pathway gene expression.

FIG. 5: Albumin Alters TGF-β Pathway Gene Expression.

TGF-β pathway map generated with GENMAPP software illustrating significant changes (>1.5 or <−1.5 fold change) in gene expression following albumin treatment in comparison to TGF-β1 treatment. Yellow labeled genes represent genes up or downregulaled following albumin treatment, blue labeled genes represent genes up or downregulated following TGF-β1 treatment, and green labeled genes represent genes up or downregulated following both treatments. Gene pathway map created by Nurit Gal and Manny Ramirez, Copyright 2002, Gladstone Institute.

FIG. 6: Blocking TGF-β Signaling Prevents Albumin-Induced Gene Expression and Epileptiform Activity.

(A) Genomic expression analysis following treatment with albumin or albumin plus TGF-β receptor blockers. Gene ontology analysis was performed with DAVID for genes showing an attenuated [(albumin log 2ratio)−(albumin+blocker log 2ratio)>0.5] or unattenuated response following treatment with albumin plus TGF-β receptor blockers in comparison to albumin treatment. (B) Fold changes for specific genes from GO analysis. (C) qPCR analysis for selected genes following albumin (n=3) or albumin plus TGF-β receptor blockers (n=4). (D and E) TGF-β receptor blockers prevent epileptiform activity induced by albumin or TGF-β1 treatment. Comparison of mean event integral in the 50-500 ms time range shows a significant increase in the field potential integral in the albumin and TGF-β1 treated slices but not in slices treated with TGF-β receptor blockers. Error bars indicate s.c.m. Asterisks indicate p<0.05.

Example 2: Effect of Losartan Potassium Treatment

Wistar male rats (160-190 g) were deeply anesthetized with Ketamin (311 mg/Kg body weight) and Xylazine (11 mg/Kg body weight) and placed in a stereotactic frame. Sagittal incision was made and a rectangular bone window was drilled over the sensory-motor cortex. The dura was removed and the underlying brain perfused for 40 minutes with aCSF for sham-operated animals (Group A; n=2); bovine serum albumin (BSA) dissolved in aCSF for treated animals (Group B; n=4); or a mixture of BSA and losartan potassium dissolved in aCSF for a second group of treated animals (Group C; n=4). BSA concentration was 0.2 mM (>98% in agarose gel electrophoresis; Sigma) and the concentration of Losartan potassium was 10 μM. The composition of the aCSF was (in mM): 129 NaCl, 21 $NaHCO_3$, 1.25 $NaH_2PO_4$, 1.8 $MgSO_4$, 1.6 $CaCl_2$, 3 KCl and 10 glucose. After perfusion, the bone window was carefully closed and the skin was sutured. Only rats with no apparent injury to the cortical surface of bleeding from cortical vessels, as seen under the surgical microscope at the end of the procedure, were included in this study.

Figure 7:
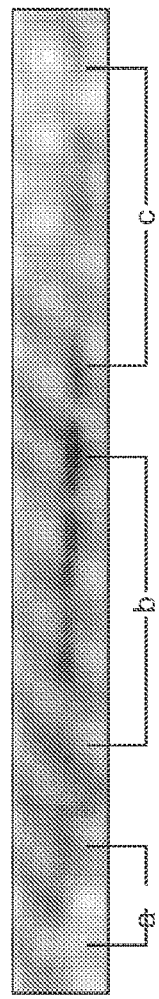
FIG. 7 depicts Western blot detection of phosphorylated Smad2 and Smad3 proteins in sham-treated (a), BSA-treated (b), and BSA+losartan treated ruts.

Animals were sacrificed 46-50 hours after surgery, the brain was removed from each animal, and the treated area was dissected. Western blot analysis was used to detect the levels of phosphorylated Smad2 and Smad3 proteins. The results are shown in FIG. 7.

Figure 8:
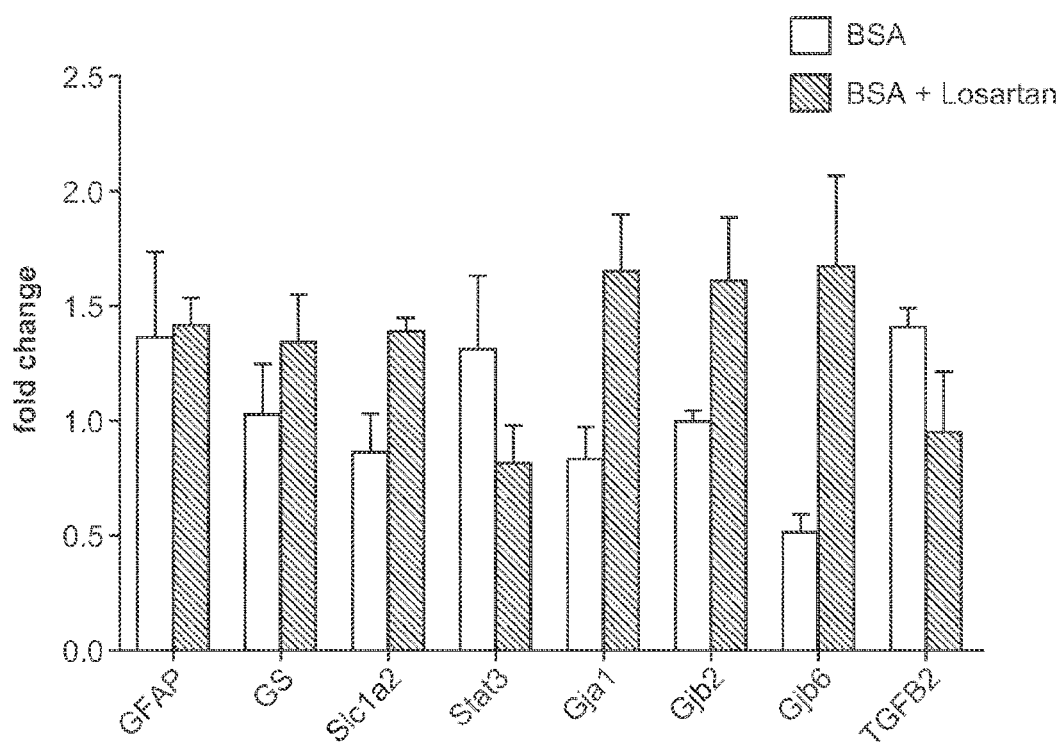
FIG. 8 depicts changes in mRNA expression levels in animals treated with BSA or BSA and losartan for 24 hours.

Changes in mRNA expression levels were determined for animals treated with BSA or BSA in addition to losartan for 24 hours. Quantitative reverse transcriptase-PCR by real-time kinetic analysis was performed with an iQ5 detection system (Bio-Rad, Hercules, Calif.). Real-time PCR data were analyzed using the PCR Miner program (Leonoudakis et al., 2008) and 18S mRNA levels were used as internal controls for variations in sample preparation. The results are shown in FIG. 8.

Brain activity was recorded from awake, behaving rats during the "epileptogenic" time window using implanted electrodes positioned on the surface of the cerebral cortex (Data Science International, USA). The EEG data is depicted in FIG. 9A-D. Signal harmony (A) and "complexity" (fractal dimension-B) were computed, and shown to increase and decrease, respectively, during albumin-induced epileptogenesis (BSA, big broken line)—indicating a gradual increase in network synchronicity. Using a "home made" automatic detection of "seizure like events" (SLEs) a sharp increase in their number one week following treatment was observed. A single, focal application of Losartan together with BSA reversed the albumin-induced EEG changes observed during epileptogenesis (A-B, small broken line) to those similar to sham-controls (unbroken line). Furthermore, the number of seizure like events (SLEs) was significantly smaller in losartan-treated rats (n=7; FIG. 9C), compared to BSA-treated ones (n=8. FIG. 9D).

REFERENCES

Abbott, N. J., Ronnback, L., and Hansson, E. (2006). Astrocyte-endothelial interactions at the blood-brain barrier. Nat Rev Neurosci 7, 41-53.

Aronica, E., Boer, K., van Vliet, E. A., Redeker, S., Baayen, J. C., Spliet, W. G., van Rijen. P. C., Troost, D., da Silva, F. H., Wadman, W. J., and Goner, J. A. (2007). Complement activation in experimental and human temporal lobe epilepsy. Neurobiol Dis 26, 497-511.

Beattie, E. C., Stellwagen, D., Morishita. W., Bresnahan, J. C., Ha. B. K., Von Zastrow, M., Beattie. M. S., and Malenka, R. C. (202). Control of synaptic strength by glial TNFalpha. Science 295, 2282-2285.

Calvo, C. F., Yoshimura, T., Gelman, M., and Mallat, M. (1996). Production of monocyte chemotactic protein-1 by rat brain macrophages. Eur J Neurosci 8, 1725-1734.

Casamenti, F., Prosperi, C., Scali, C., Giovannelli, L., Colivicchi, M. A., Faussone-Pellegrini, M. S., and Pepeu, G. (1999). Interleukin-1beta activates forebrain glial cells and increases nitric oxide production and cortical glutamate and GABA release in vivo: implications for Alzheimer's disease. Neuroscience 91, 831-842.

Choi, J. S., Kim, S. Y., Park, H. J., Cha, J. HI., Choi, Y. S., Kang, J. E., Chung, J. W., Chun, M. H., and Lee, M. Y. (2003). Upregulation of gp130 and differential activation of STAT and p42/44 MAPK in the rat hippocampus following kainic acid-induced seizures. Brain Res Mol Brain Res 119, 10-18.

Cornford, E. M. (1999). Epilepsy and the blood brain harrier: endothelial cell responses to seizures. Adv Neurol 79, 845-862.

Cornford, E. M., and Oldendorf, W. H. (1986). Epilepsy and the blood-brain barrier. Adv Neurol 44, 787-812.

Dennis, G., Jr., Sherman, B. T., Hosack, D. A., Yang, J., Gao, W., Lane, H. C., and Lempicki, R. A. (2003). DAVID: Database for Annotation, Visualization, and Integrated Discovery. Genome Biol 4, P3.

Eisen, M. B., Spellman, P. T., Brown, P. O., and Botstein, D. (1998). Cluster analysis and display of genome-wide expression patterns. Proc Natl Acad Sci USA 95, 14863-14868.

Gorter, J. A., van Vliet, E. A., Aronica, E., Breit, T., Rauwerda, H., Lopes da Silva, F. H., and Wadman, W. J. (2006). Potential new antiepileptogenic targets indicated by microarray analysis in a rat model for temporal lobe epilepsy. J Neurosci 26, 11083-11110.

Gutnick, M. J., Connors, B. W., and Prince. D. A. (1982). Mechanisms of neocortical epileptogenesis in vitro. J Neurophysiol 48, 1321-1335.

Hoffman, K. B., Pinkstaff, J. K., (Gall. C. M., and Lynch, G. (1998). Seizure induced synthesis of fibronectin is rapid and age dependent: implications for long-term potentiation and sprouting. Brain Res 812, 209-215.

Hu, S., Sheng, W. S., Ehrlich, L. C., Peterson, P. K., and Chao, C. C. (2000). Cytokine effects on glutamate uptake by human astrocytes. Neuroimmunomodulation 7, 153-159.

Ivens, S., Kaufer, D., Flores, L. P., Bechmann, I., Zumsteg, D., Tomkins, O., Seiffert, E., Heinemann. U., and Friedman. A. (2007). TGF-beta receptor-mediated albumin uptake into astrocytes is involved in neocortical epileptogenesis. Brain 130, 535-547.

Kasantikul, V., Brown. W. J., Oldendorf, W. H., and Crandall, P. C. (1983). Ultrastructural parameters of limbic microvasculature in human psychomotor epilepsy. Clin Neuropathol 2, 171-178.

Lerner. J. T., Sankar. R., and Mazarati, A. M. (2008). Galanin and epilepsy. Cell Mol Life Sci 65, 1864-1871.

Lubin, F. D., Ren, Y., Xu, X., and Anderson, A. E. (2007). Nuclear factor-kappa B regulates seizure threshold and gene transcription following convulsant stimulation. J Neurochem 103, 1381-1395.

Manley, N. C., Bertrand, A. A., Kinney, K. S., ling, T. C., and Sapolsky, R. M. (2007). Characterization of monocyte chemoattractant protein-1 expression following a kainate model of status epilepticus. Brain Res 1182, 138-143.

Marchi, N., Angelov, L., Masaryk, T., Fazio, V., Granata, T., Hemandez, N., Hallene, K., Diglaw, T., Franic, L., Najm, L, and Janigro, D. (2007). Seizure-promoting effect of blood-brain barrier disruption. Epilepsia 48, 732-742.

Neuwelt, E. A. (2004). Mechanisms of disease: the blood-brain barrier. Neurosurgery 54, 131-140; discussion 141-132.

Oby, E., and Janigro, D. (2006). The blood-brain barrier and epilepsy. Epilepsia 47, 1761-1774.

Pavlovsky, L., Browne. R. O., and Friedman, A. (2003). Pyridostigmine enhances glutamatergic transmission in hippocampal CA1 neurons. Exp Neurol 179, 181-187.

Pfaffl, M. W. (2001). A new mathematical model for relative quantification in real-time RT-PCR. Nucleic Acids Res 29, e45.

Rizzi, M., Perego, C., Aliprandi, M., Richichi, C., Ravizta, T., Colella, D., Veliskova, J., Moshe, S. L., De Simoni, M. G., and Vezzani, A. (2003). Glia activation and cytokine increase in rat hippocampus by kainic acid-induced status epilepticus during postnatal development. Neurobiol Dis 14, 494-503.

Rong, Y., and Baudry, M. (1996). Seizure activity results in a rapid induction of nuclear factor-kappa B in adult but not juvenile rat limbic structures. J Neurochem 67, 662-668.

Rozovsky, I., Morgan. T. E., Willoughby, D. A., Dugichi-Djordjevich, M. M., Pasinetti, G. M., Johnson, S. A., and Finch, C. E. (1994). Selective expression of clusterin (SGP-2) and complement C1qB and C4 during responses to neurotoxins in vivo and in vitro. Neuroscience 62, 741-758.

Salomonis, N., Hanspers, K., Zambon, A. C., Vranizan, K., Lawlor, S. C., Dahlquist, K. D., Doniger, S. W., Stuart, J., Conklin, B. R., and Pico, A. R. (2007). GenMAPP 2: new features and resources for pathway analysis. BMC Bioinformatics 8, 217.

Seiffert, E., Dreier, J. P., Ivens, S., Bechmann, I., Tomkins, O., Heinemann, U., and Friedman, A. (2004). Lasting blood-brain barrier disruption induces epileptic focus in the rat somatosensory cortex. J Neurosci 24, 7829-7836.

Shi, Y., and Massague, J. (2003). Mechanisms of TGF-beta signaling from cell membrane to the nucleus. Cell 113, 685-700.

Siddiqui, S. S., Siddiqui, Z. K., and Malik, A. B. (2004). Albumin endocytosis in endothelial cells induces TGF-beta receptor II signaling. Am J Physiol Lung Cell Mol Physiol 286, 11016-1026.

Stellwagen, D., Beattie, E. C., Seo, J. Y., and Malenka, R. C. (2005). Differential regulation of AMPA receptor and GABA receptor trafficking by tumor necrosis factor-alpha. J Neurosci 25, 3219-3228.

Stevens. B., Allen, N. J., Vazqucz, L. E., Howell. G. R., Christopherson, K. S., Nouri, N., Micheva, K. D., Mehalow, A. K., Huberman, A. D., Stafford, B., et al. (2007). The classical complement cascade mediates CNS synapse elimination. Cell 131, 1164-1178.

Tian, G. F., Azmi, H., Takano, T., Xu, Q., Peng, W., Lin, J., Oberheim, N., Lou, N., Wang, X., Zielke. H. R., et al. (2005). An astrocytic basis of epilepsy. Nat Med 11, 973-981.

Tomkins, O., Friedman, O., Ivens, S., Reiffurth, C., Major, S., Dreier, J. P., Heinemann, U., and Friedman, A. (2007). Blood-brain barrier disruption results in delayed functional and structural alterations in the rat neocortex Neurobiol Dis 25, 367-377.

Tomkins, O., Kaufer, D., Korn, A., Shelef, L, Golan, H., Reichenthal, E., Soreq, H., and Friedman, A. (2001). Frequent blood-brain barrier disruption in the human cerebral cortex. Cell Mol Neurobiol 21, 675-691.

Town, T., Laouar. Y., Pittenger, C., Mori, T., Szckely. C. A., Tan, J., Duman. R. S., and Flavell, R. A. (2008). Blocking TGF-beta-Smad2/3 innate immune signaling mitigates Alzheimer-like pathology. Nat Med 14, 681-687.

van Vliet E. A., da Costa Araujo. S., Redeker, S., van Schaik. R., Aronica, E., and Gorter, J. A. (2007). Blood-brain barrier leakage may lead to progression of temporal lobe epilepsy. Brain 130, 521-534.

Vezzani, A., and Granata, T. (2005). Brain inflammation in epilepsy: experimental and clinical evidence. Epilepsia 46, 1724-1743.

Viviani, B., Barlesaghi, S., Gardoni. F., Veiiani, A., Behrens, M. M., Bartfai, T., Binaglia, M., Corsini, E., Di Luca. M., Galli, C. L., and Marinovich, M. (2003). Interleukin-1beta enhances NMDA receptor-mediated intracellular calcium increase through activation of the Src family of kinases. J Neurosci 23, 8692-8700.

Wetherington, J., Serrano, G., and Dingledine, R. (2008). Astrocytes in the epileptic brain. Neuron 58, 168-178.

Yanagisawa, M., Nakashima, K., and Taga, T. (1999). STAT3-mediated astrocyte differentiation from mouse fetal neuroepithelial cells by mouse oncostatin M. Neurosci Lett 269, 169-172.

Zhao, S., and Fernald. R. D. (2005). Comprehensive algorithm for quantitative real-time polymerase chain reaction. J Comput Biol 12, 1047-1064.

Zlokovic, B. V. (2008). The blood-brain barrier in health and chronic neurodegenerative disorders. Neuron 57, 178-201.

Example 3: Astrocyte Dysfunction in Epileptogenesis

Materials and Methods

Animals were housed and handled according to the directives of the internationally accredited Animal Care and Use Committees (IACUC) at Charité University Medicine, Berlin, and Ben-Gurion University of the Negev, Beer-Sheva. All experimental procedures were approved by the ethical committees supervising experiments on animals at Charité University Medicine (in-vivo approval no.: G0104/05, in-vitro: T0228/04) and Ben-Gurion University of the Negev (approval no.: BGU-R-71-2006).

In-Vivo Experiments.

The in-vivo experiments were performed as previously described in Seiffert et al. (2004). In brief, adult male Wistar rats (120-250 g) were anesthetized using ketamine and xylazine and placed in a stereotactic frame. A 4-mm diameter bone window was drilled over the somatosensory cortex, the dura was opened and the underlying cortex was perfused with artificial cerebrospinal fluid (ACSF). For the "treated" rats group, the BBB-disrupting agent deoxycholic acid sodium salt (DOC, 2 mM, Sigma-Aldrich, Steinheim, Germany) or bovine serum albumin (0.1 mM, >98% in agarose cell electrophoresis; catalogue no. A7906, Sigma Aldrich, Steinheim, Germany) was added to the ACSF. Albumin concentrations corresponded to 25% of the normal serum concentration [determined to be 0.4 mM for 10 rats, see also Geursen and Grigor (1987); final osmolarity of 303-305 mOsmol/l]. For the sham-operated control group, the cortex was perfused with ACSF. The composition of the ACSF was (in mM): 129 NaCl, 21 NaHCO$_3$, 1.25 NaH$_2$PO$_4$, 1.8 MgSO$_4$, 1.6 CaCl$_2$. 3 KCl, and 10 glucose. Rats were sacrificed at 7-8, 24, or 48 h following treatment, before the onset of epileptiform activity (>4 days, see Seiffert et al., 2004).

Microarrays.

Total RNA from animals treated with DOC or with albumin was isolated from the somatosensory cortex, directly under the craniotomy area, using the TRIzol® reagent (Invitrogen, Carlsbad, Calif.), and prepared using the Affymetrix GeneChip one-cycle target labeling kit (Affymetrix, Santa Clara, Calif.). Biotinylated cRNA was then fragmented and hybridized to the GeneChip Rat Genome 230 2.0 Array according to manufacturer's protocols (Affymetrix Technical Manual). The array data was normalized by using GCRMA (GC Robust Multi-Array Average) or RMA (Robust Multi-Array Average) analysis. One array was run for each treatment (DOC and albumin) and for every contralateral hemisphere for the following time points: 7/8, 24, and 48 h. The data from a sham-treated animal (24 h) was used to normalize the other arrays. To identify genes involved in astrocytic functions, GeneCards (http://www-.genecards.org), querying for "astrocyte", was used. For comparison of the relative changes in the expression of astrocytic vs. neuronal genes, gene sets of astrocytic and neuronal enriched genes (expressed by S100β+ and S100β-/PDGFRα-/MOG-cells, respectively) were used (Cahoy et al. J Neurosci 28:264-278, 2008). Cluster analysis was performed with MATLAB by assessing the expression relationship as the Euclidean distance in N-dimensional space between measurements (N denotes number of gene transcripts). Arrays were then clustered according to distance data, by using the Unweighted Pair Group Method with Arithmetic mean method (UPGMA, Gronau and Moran, 2007).

In-Vitro Astrocytic and Neuronal Culture Preparations.

Primary neuronal cortical cultures were prepared from embryonic day 18 rats as reported previously (Kaufer et al., 2004). Briefly, cells were dissociated with a papain solution for 20 min at 37° C., After the removal of the papain solution, the tissue was resuspended in growth medium [MEM with Earle's salts containing 2.5% B27 supplement, 0.1% mito serum extender, 5% fetal bovine serum (FBS), 20 mM glucose, and 5 mM L-glutamine] and dissociated by mechanical trituration. The cells were plated, and after 4 h in vitro the cell culture medium was replaced with neurobasal medium supplemented with 2% B27 supplement and 0.5 mM GlutaMAX™. The cells were maintained in 5% CO$_2$ at 37° C. After 7 days in vitro, cytosine arabinofuranoside (AraC) (10 μM) was added to the cultures. After 10 days in vitro, the cells were incubated with 0.4 mM albumin for 24 h at 37° C. For astrocytic cultures, astrocytes were isolated from the cerebral cortices of P0 rat pups. Cells were dissociated with papain and mechanical trituration. The cells were cultured in high-glucose Dulbecco's modified eagle medium supplemented with 10% FBS and 1% penicillin/streptomycin at 37° C. and in 5% C02 (medium was replaced every 3-4 days). After 10 days in vitro, the culture medium was replaced with serum-free high-glucose DMEM (containing 1% penicillin/streptomycin) for 18 h. The cells were then incubated in scrum-free medium containing 0.4 mM albumin for 24 h at 37° C. For immunostainings cells were washed with phosphate buffered saline (PBS) and fixed in 4% paraformaldehyde for 15 min. The cells were permeabilized with 0.2% Triton X-100 in PBS for 5 min and washed in PBS. They were then incubated with 5% normal donkey serum in PBS for one hour at room temperature followed by overnight incubation at 4° C. with either mouse anti-NeuN (1:1000: Chemicon, Temecula, Calif.) or mouse anti-GFAP (1:1000: Cell Signaling Technology, Beverly, Mass.). The cells were washed in PBS, incubated with donkey anti-mouse Cy3 (1:1000; Jackson ImmunoResearch. West Grove, Pa.) for 1 hour at room temperature, and then counterstained with DAPI.

Real-Time Polymerase Chain Reaction.

Total RNA was isolated from the somatosensory cortices of animals treated with DOC or albumin (24 h treatment; n=3) or from primary cultures (astrocytic and neuronal, n=3 independent experiments). Expression levels were determined by real-time reverse transcriptase-PCR (RT-PCR) with an iQ5 detection system (Bio-Rad, Hercules, Calif.) using gene-specific primer pairs. RT-PCR data were analyzed using the PCR Miner program (Zhao and Fernald, 2005), and fold changes in gene expression were represented relative to sham-operated controls (in-vivo samples) or serum-deprived controls (in-vitro, samples). Ribosomal 18S RNA (18S rRNA) was used as an internal control for variations in sample preparation. For samples from in-vivo treatments, RT-PCR was performed with the iScript one-step RT-PCR kit (Bio-Rad). Control RT-PCR reactions were performed without reverse transcriptase to verify amplification of genomic DNA. For in-vitro samples, DNase treatment was applied, followed by first-strand cDNA synthesis (iScript cDNA Synthesis kit, Bio-Rad). PCR reactions were carried out with iQ SYBR Green Supermix (Bio-Rad). Primer specificity was verified by melt curve analysis. The amplification cycles for 18S, Gja1, GS, SLC1A2, SLC1A3 (GLAST) and Kenj10 consisted of 40 cycles of 10 s at 95° C., 30 s at 55° C., and 30 s at 72° C. The amplification cycles for Gjb2 and Gjb6 consisted of 40 cycles of 10 s at 95° C., 30 s at 60° C., and 30 s at 72° C.

Primer sequences (forward, reverse) were as follows:

```
18S rRNA (GenBank accession number M11188.1,
5'-CCATCCAATCGGTAGTAGCG-3',    (SEQ ID NO: 1)

5' GTAACCCGTTGAACCCCATT-3';    (SEQ ID NO: 2))

SLC1A3 (GenBank accession number NM_019225.1;
5'-GAGGCCATGGAGACTCTGAC-3',    (SEQ ID NO: 3)

5'-CGAAGCACATGGAGAAGACA-3';    (SEQ ID NO: 4))

GS (GenBank accession number NM_0170713;
5'-AGCGACATGTACCTCCATCC-3',    (SEQ ID NO: 5)

5' TACAGCTGTGCCTCAGGTTG-3';    (SEQ ID NO: 6))
```

-continued

```
Kcnj10 (GenBank accession number X83585.1;
5'-GAGACGACGCAGACAGAGAG-3',    (SEQ ID NO: 7)

5' CCACTGCATGTCAATGAAGG-3';    (SEQ ID NO: 8))

Gjb2 (GenBank accession number NM_001004099.1;
5'-GGTTTGTGATGTGAGCATGG-3',    (SEQ ID NO: 9)

5'-CTCAGCACACCAAGGATGAA-3';    (SEQ ID NO: 10))

Gjb6 (GenBank accession number NM_053388.1;
5'-GCCAAGATGAGTCACAGCAA-3',    (SEQ ID NO: 11)

5'-TCAGAGCTGGATCACAATCG-3';    (SEQ ID NO: 12))

Gja1 (GenBank accession number NM_012567.2;
5'-TCCTTGGTGTCTCTCGCTTT-3',    (SEQ ID NO: 13)

5'-TTTGGAGATCCGCAGTCTTT-3';    (SEQ ID NO: 14))

SLC1A2 (GenBank accession number NM_017215.2;
5'-GGTCAATGTAGTGGGCGATT-3',    (SEQ ID NO: 15)

5'-GGACTGCGTCTTGGTCATTT-3'.    (SEQ ID NO: 16))
```

In-Vitro Electroplysiological Recordings.

For electrophysiological experiments, rats were deeply anesthetized with isoflurane and then decapitated. Brains were quickly removed, and transverse hippocampal-cortical slices (400 m thick) were prepared using a vibratome (Campden Instruments, Loughborough, UK). Slices were maintained in a humidified, carbogenated (5% $CO_2$ and 95% $O_2$) gas atmosphere at 36±1° C. and perfused with ACSF in a standard interface chamber (Seiffert et al., 2004; Ivens et al., 2007). To mimic the altered ionic environment during BBB disruption, recordings were acquired in a serum-adapted electrolyte solution (sACSF; see Seiffert et al. 2004). sACSF was similar in composition to the ACSF except for different concentrations of $MgSO_4$ (0.8 mM), $CaCl_2$ (1.3 mM), KCl (5.7 mM) and glutamine (1 mM). "Treated" slices were incubated with sACSF containing 0.1 mM bovine serum albumin for 2 h before transfer to the perfusion chamber.

Electrophysiological recordings were obtained 6-10 h following perfusion with sACSF. Control slices were treated similarly, using sACSF without albumin. For extracellular recordings, glass microelectrodes (~3 MΩ, 154 mM NaCl) were positioned in layer 4 of the neocortex. Slices were stimulated with brief (100 µs) pulses, by using bipolar stimulation electrodes placed at the border between white and gray matter in the same conical column. Trains of 50 stimuli were applied at 2, 5, 10, 20, 50 and 100 Hz, at 2.5× threshold stimulation intensity. Signals were amplified (SEC-10L; NPI Electronics, Tamm, Germany), filtered at 2 kHz, displayed on an oscilloscope, digitized on-line (CED)-1401 micro; Cambridge Electronics Design, Cambridge, UK) and stored for off-line analysis. Extracellular potassium concentrations ($[K+]_o$) were measured with ion-sensitive microelectrodes (ISMEs; Lux and Neher, 1973: Jauch et al., 2002).

In vitro intracellular recordings were obtained from pyramidal neurons (layer 2-3) 23-28 h following the in vivo treatment with albumin or from control rats. Currents were recorded using the whole cell patch configuration, as described previously (Pavlovsky et al., 2003). In brief, glass pipettes were pulled from capillaries using a vertical puller (Narashige, Greenvale, N.Y.) and filled with a solution comprising (in mM): 150 CsCl, 1 $MgCl_2$, 10 HEPES, 4 $Na_2ATP$, 0.1 $CaCl_2$, and 1.1 mM EGTA, pH adjusted to 7.2 with a final osmolarity of 290-310 mOsm. Cells were visualized using infrared differential interference phase contrast video-microscopy. Recordings were performed using AxoPatch 700B (Axon Instruments, Foster City, Calif.), digitized at 10 kHz and recorded using pClamp 9.2 (Axon Instruments, Foster City, Calif.). Patch pipette's resistance was 4-5 MΩ. Series resistance was not electronically compensated; however, cells in which series resistance varied by more than 25% were excluded from the analysis. Stimulation protocols were started at least 5 min following impalement to allow intracellular dialysis with the pipette solution. Excitatory post-synaptic currents (EPSCs) were evoked—using a bipolar stimulating electrode positioned <200 µm from the recorded cell—at 75% of the intensity producing maximal EPSCs. N-methyl-D-aspartic acid (NMDA) currents were recorded in the presence of blockers of α-amino-3-hydroxy-5-methyl-4-isoxazole-propionic acid (AMPA)/kainate (i.e., 30 µM CNQX) and of gamma-aminobutyric acid A ($GABA_A$) receptors (i.e., 10 µM bicuculine methiodide). Cells were voltage clamped to +40 mV to alleviate NMDA receptor blockade and inactivate fast $Na^+$ currents. In some experiments, dihydrokainic acid (DHK, Tocris, Bristol, UK), 100 µM, was added to the extracellular solution to selectively block the astrocyte specific glutamate transporter, SLC1A2 (see Arriza et al., 1994).

Computer Simulations.

A computer model was implemented using the NEURON modeling environment (Hines and Carnevale, 1997) with 20-µs time steps. The model consisted of a multi-compartment isolated cell, simulating a layer 2/3 cortical neuron, using only passive membrane properties. Geometric parameters and spatial relationships of the 74 compartments were modeled after Traub and colleagues (2003). Resting membrane potential was set at −65 mV (determined by $Na^+$ and $K^+$ conductance); membrane capacitance $C_m$ was 0.9 µF/cm$^2$; and the cytoplasmic resistance was set at 250 Ω/cm$^2$. Simulated excitatory inputs consisted of eight synapses on apical dendrites (located 1368 µm from the soma), contributing currents with AMPA and NMDA kinetics modeled after Saftenku (2005) and Kampa et al. (2004), respectively. AMPA to NMDA maximal current ratios were set at 1 (Myme et al., 2003). Synaptic currents were triggered by a surge of 'glutamate', decaying with first-order kinetics (baseline time constant=1.2 ms). Down-regulation of uptake mechanisms was simulated by changing the time constant of the decay function, similar to the effect of the application of DL-threo-β-benzyloxyaspartate (DL-TBOA, Diamond, 2005). To investigate the effects of altered $[K^+]_o$, each compartment was enveloped by a fixed space in which potassium was allowed to accumulate. $[K^+]_o$ 'diffused' either into the bathing solution or into astrocytes with $K_{IR}$ kinetics. Since $K_{IR}$ channel conductance is proportional to $[K^+]_o$ (Sakmann and Trube, 1984), $K^+$ influx into 'astrocytes' was determined by the local potassium gradient ($[K^+]_o - [K^+]_{bath}$) modulated by $K_{IR}$ conductance (log $[K^+]_o$; adapted from Ciani et al., 1978).

$$\frac{\Delta [K^+]_c}{\Delta t} = \frac{3(I_k - I_k^{rest})}{VF} (1 \ C) \frac{[K^+]_o - [K^+]_{bath}}{\tau_{ECS}} - C \frac{([K^+]_o - [K^+]_{bath})}{\tau_{astrocytic}} \log [K^+]_o,$$

where $I_k$—momentary $K^+$ flux (nA/cm$^2$), $I_k^{rest}$—resting $K^+$ flux (nA/cm$^2$), $\tau_{ECS}$—time constant for potassium diffusion into the extracellular space, $\tau_{astrocytic}$—time constant for potassium diffusion into astrocytes. F—Faraday constant, C—ratio of astrocytic $K^+$ uptake relative to extracellular diffusion, and V—radius of enveloping extracellular space, set at 20 nm (Egelman and Montague, 1999; Savtchenko et al., 2000). The ionic flux equation describes first-order potassium clearance by both free diffusion and 'astrocytic' uptake (see Kager et al., 2000). Lateral diffusion of $K^+$ ions was not taken into account. To simulate a decrease in astrocytic potassium clearance, $\tau_{astrocytic}$ was increased to mimic a reduction in astrocytic $K_{IR}$ channels. "Resting" ion concentrations were set at (in [mM]): $[Na^+]_o$, 145; $[Na^+]_i$, 12; $[K^+]_o$, 3.5; $[K^+]_i$, 140.

Statistical Analysis.

Data are expressed as means±SEM. Differences between treated and control slices were determined by the Mann-Whitney U test for two independent samples. Statistical tests were performed using SPSS 13.0 for Windows. The level of statistical significance was set at $p<0.05$, unless otherwise stated.

Results

Astrocytic Transcriptional Changes Following BBB Opening or Exposure to Albumin

Figure 10A:
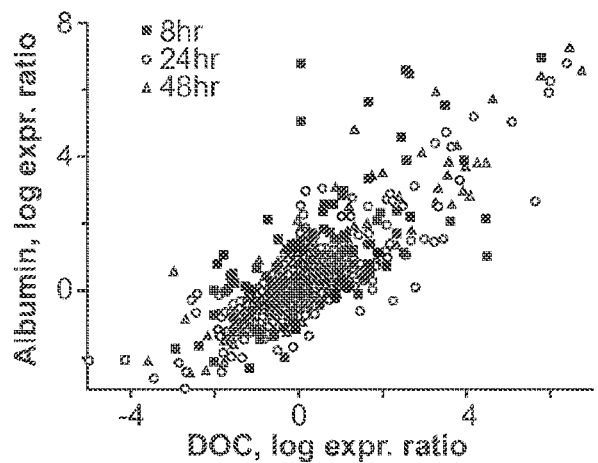
FIGS. 10*a-d* depict transcriptional changes in astrocytes following exposure to albumin or BBB disruption.
Figure 10B:
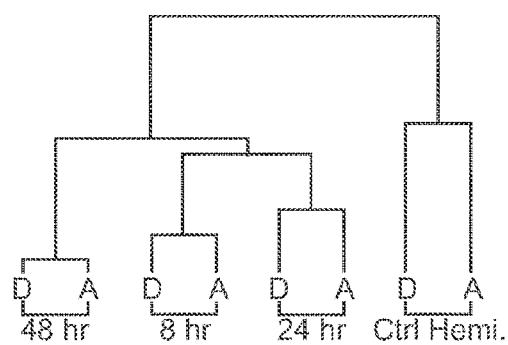

To explore changes in astrocytic gene expression during epileptogenesis, gene-array data from DOC- and albumin-treated brains (n=3 from each treatment) were analyzed during the first 48 h after treatment and prior to the development of epileptiform activity (Ivens et al., 2007; Seiffert et al., 2004). When compared to sham-operated controls, the two treatments, at each time point, resulted in similar changes in expression of astrocytic-enriched genes with a correlation coefficients between the different treatments (see Methods) of $r^2$=0.69, 0.82, 0.85 for 8, 24 and 48 h following treatment, respectively, $p<0.0001$, FIG. 10a). Unsupervised hierarchical cluster analysis revealed further similarities between changes in transcripts levels in treated cortices (which cluster according to time after treatment) (FIG. 10b) while transcripts changes in the contralateral, untreated, hemispheres are relatively dissimilar and cluster together.

Figure 10C:
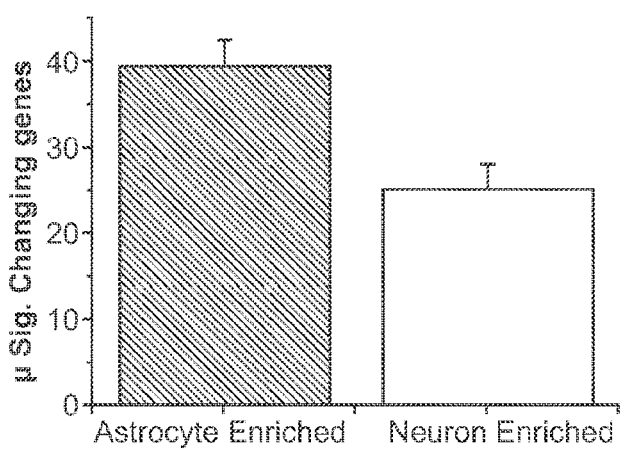
Figure 10D:
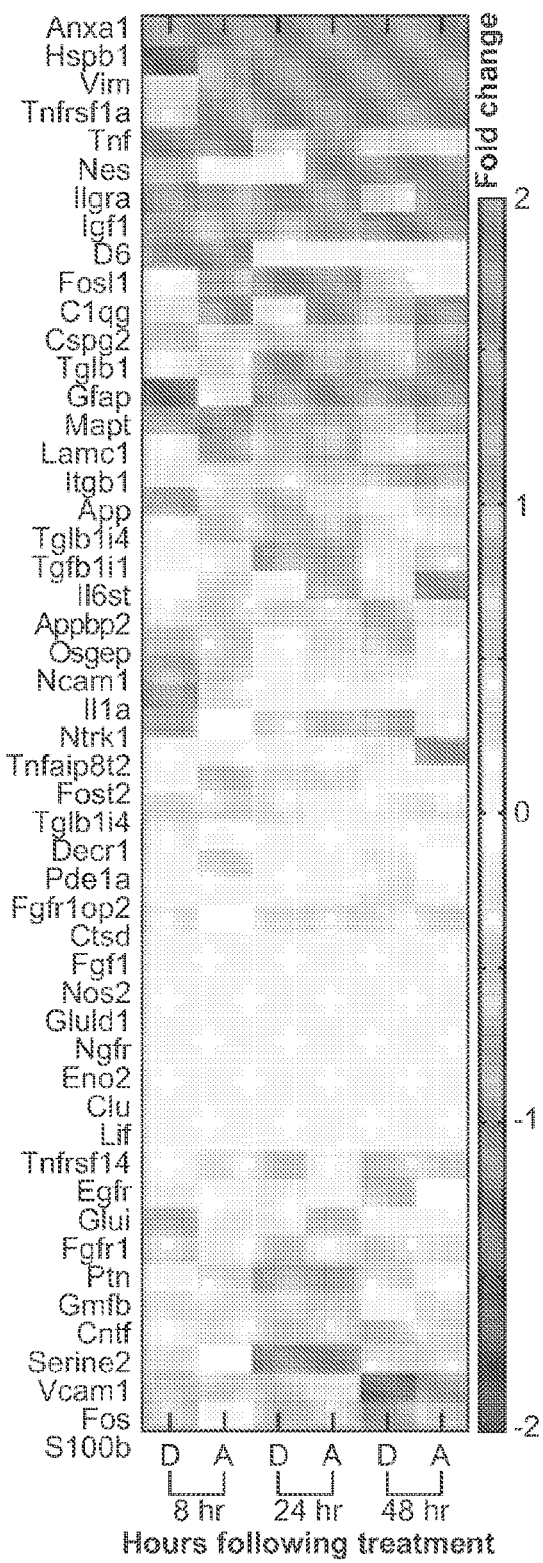

In a recent study, Cahoy and colleagues (2008) created a transcriptome database reflecting cell type-specific, comprehensive mRNA expression levels in astrocytes, neurons and oligodendrocytes. We used these gene lists to classify genes into "astrocytic" or "neuronal" categories. When compared with the "neuronal" category at all examined lime points, the "astrocytic" category included a higher average number of genes that underwent a change in expression of more than ±150% (FIG. 10c). Comparison between the results at 8 and 48 h after treatment showed an increase in the average number of genes that reached 150% change in both groups (34 vs. 40 for astrocytes and 21 vs. 28 for neurons, 8 and 48 h after treatment, respectively). The expression levels of genes reported as over-expressed in reactive astrocytes (Ridet et al., 1997) was also examined and found to show a large overlap with over-expressed genes 8, 24 and 48 h following both treatments (FIG. 10d). These results are consistent with the hypothesis that an early and prominent change in astrocytic gene expression is an important early feature of BBB-breakdown or albumin-induced epileptogenesis.

Altered Expression of Astrocytic Potassium and Glutamate Regulating Genes

Figure 11A:
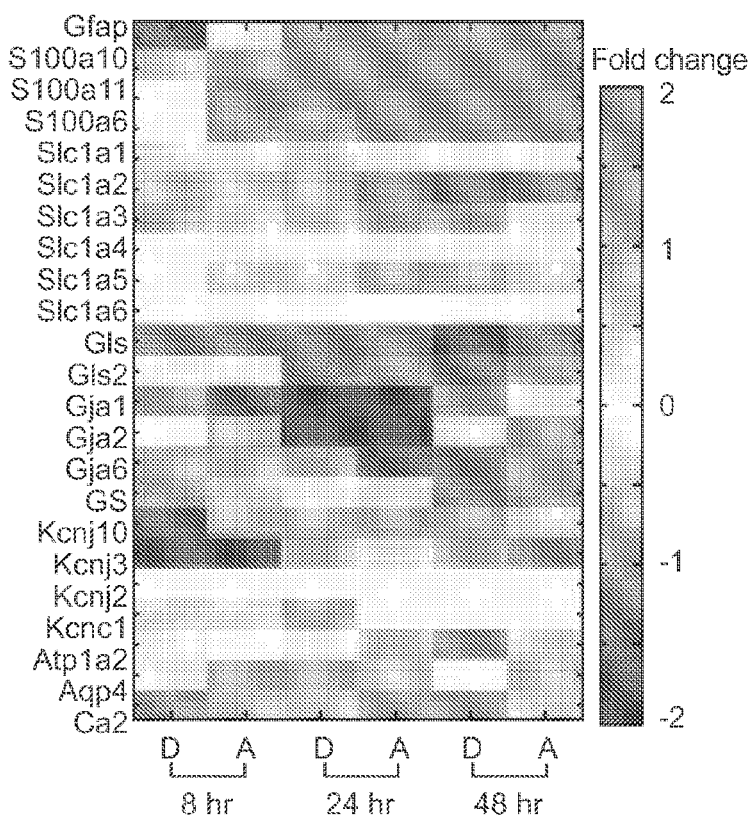
FIGS. 11*a-d* depict alterations in astrocytic potassium and glutamate regulating genes.
Figure 11B:
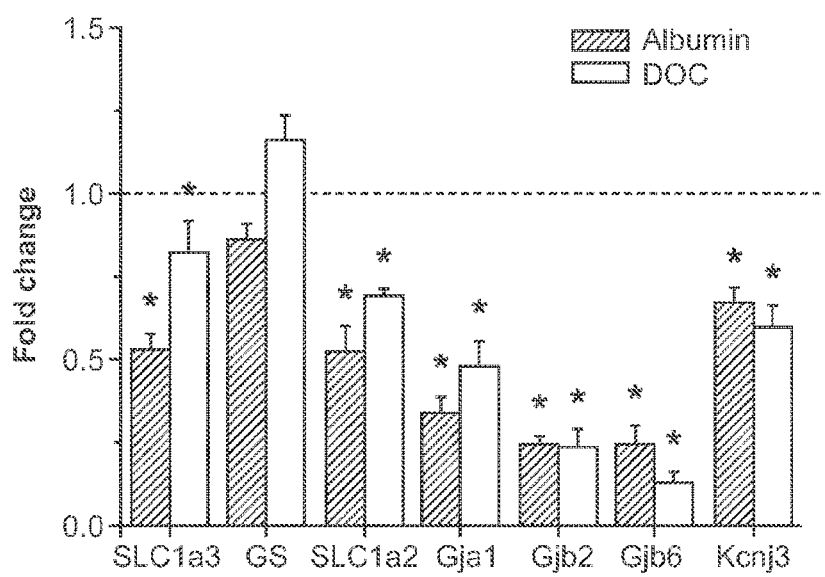

In their pioneering study, Kuffler and Potter (1964) established that astrocytes are crucial for the control of the brain's extracellular environment. Specifically, these cells limit the accumulation of $[K^+]_o$ and glutamate (Oliet et al., 2001: Newman et al., 2004), thus potentially contributing to the regulation of neuronal excitability. The gene array results were searched for changes in the level of expression of several potassium and glutamate homeostasis-related genes. Transcripts coding for the predominantly astrocytic (Kenj10), but not neuronal (e.g. Kenj2 or Kene1, see Butt and Kalsi, 2006) inward-rectifying $K^+$ channel ($K_{IR}$) were found to be down-regulated. In addition, the mRNA coding for the astrocytic glutamate transporters of the solute carrier family 1, subfamily A members SLC1A2 and SLC1A3 (see Su et al., 2003; Chaudhry et al., 1995), but not for SLC1A4, was down-regulated. In contrast, SLC1A1 (preferentially expressed in neurons; see Rothstein et al., 1994) did not show significant changes in expression levels. Glutaminase (Gls, Gls2) and glutamine synthetase (GS), both of which are predominantly expressed in astrocytes (Derouiche and Frotscher, 1991) and are responsible for regulating glutamate levels, were also down-regulated (FIG. 11a). Furthermore, the gene arrays showed that at most time points there was a significant down-regulation of gap junction proteins (Gja1, Gjb2, Gjb6) 24 h following treatment, a finding that indicates reduced spatial buffering capacity (see Wallraff et al, 2006). Real-time RT-PCR confirmed the main observations obtained from the gene arrays, i.e., significant up-regulation of GFAP, and down-regulation of KCNJ10 ($K_{IR}$ 4.1) as well as KCNJ3, SLC1A2 and SLC1A3, Gja1, Gjb2 and Gjb6 at all time points (connexins 43, 26 and 30, respectively, FIG. 11b). In contrast, glutamine synthetase did not show significant down-regulation (FIG. 11b).

Figure 11C:
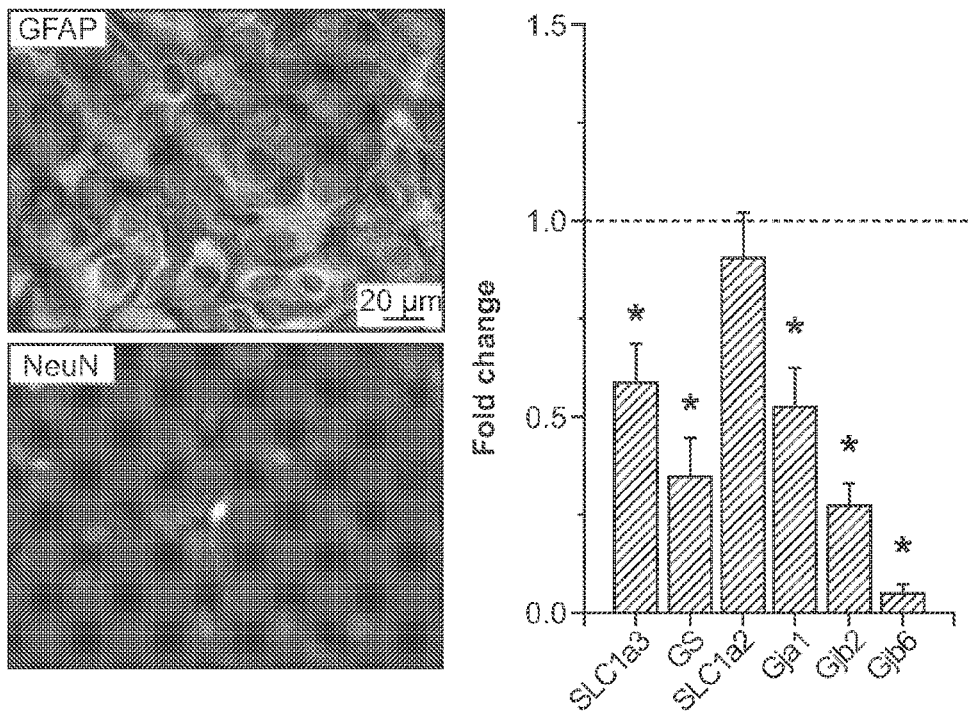
Figure 11D:
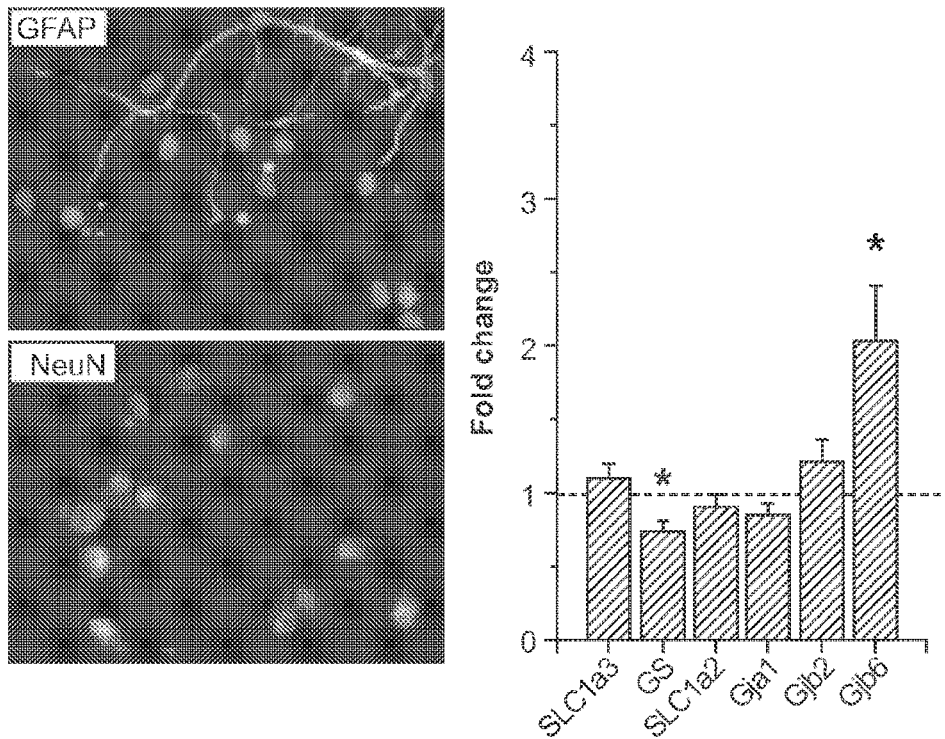

The microarray results indicated a rapid and robust change in astrocytic gene expression in vivo following BBB breakdown or brain exposure to serum albumin. To further validate the specificity of the astrocytic response to albumin, cell cultures enriched with either astrocytes or neurons were exposed (see Methods) to albumin for 24 h. Significantly, the astrocytic cultures responded with significant down-regulation of the same transcripts found to respond in vivo to albumin (S1C1A3, GS, Gja1, Gjb2 and Gjb6, FIG. 11c). No significant differences in expression levels of the same transcripts were found in the neuronal-enriched culture (except for downregulation of GS and upregulation of Gjb6 mRNA levels, FIG. 11d), confirming that the changes observed in-vivo do indeed reflect an astrocytic response.

Epileptogenesis Involves Reduced Glutamate and Potassium Clearance

Figure 12A:
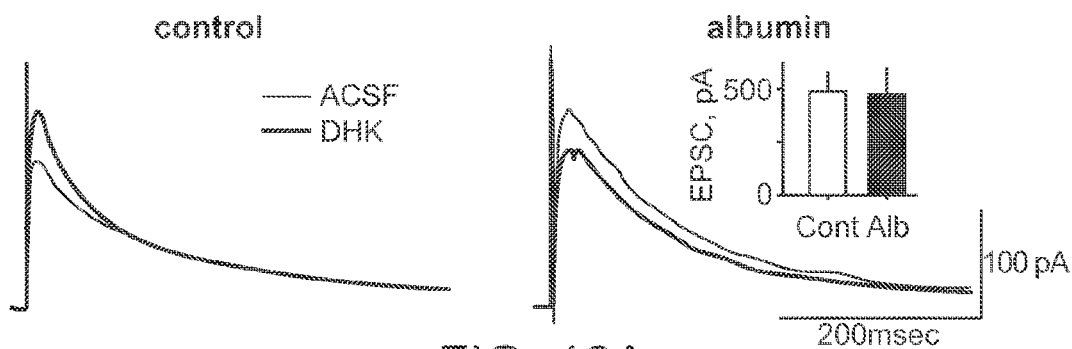
FIGS. 12*a-e* depict electrophysiological evidence for reduced glutamate and potassium buffering during epileptogenesis.
Figure 12B:
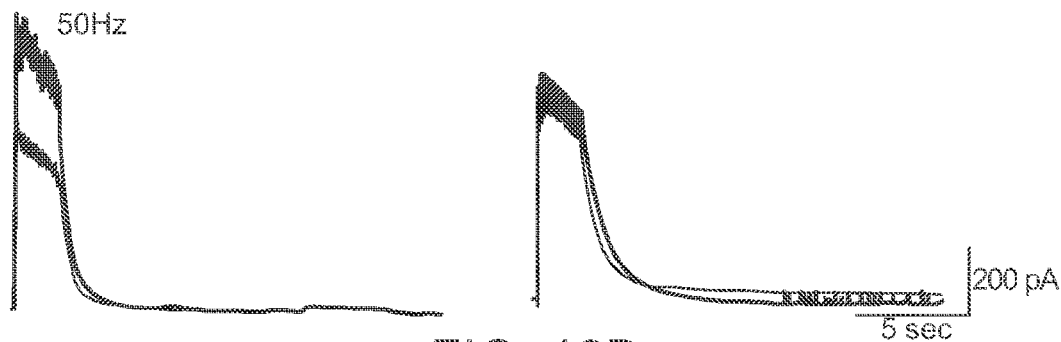
Figure 12C:
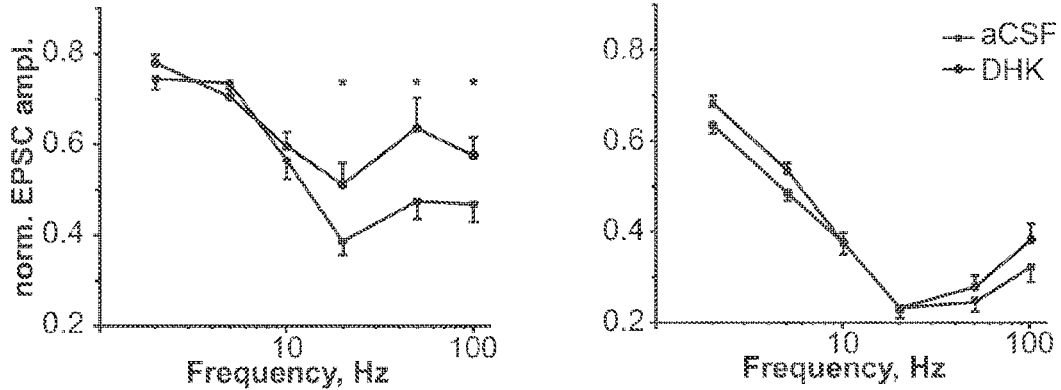

To confirm that the transcriptional changes induced by albumin were associated with altered cellular functions, the clearance of extracellular glutamate and potassium in cortical slices 24 hours following albumin treatment in vivo was investigated. To measure synaptic glutamate levels during neuronal activation, the slowly inactivating (Lester et al., 1990) NMDA currents in cortical neurons were recorded by using the whole-cell patch configuration (in the presence of non-NMDA glutamate and GABA receptor blockers, see Methods). Cells were clamped at +40 mV to prevent a potential confounding effect of post-synaptic depolarization due to the accumulation of synaptic $[K^+]_o$. Mean single EPSC rise-time and amplitude were similar in both control and albumin-treated groups [14.5±0.5 vs. 13.2±0.7 ms and 505±100 vs. 492±140 pA, for rise-time (not shown) and amplitude, respectively in treated vs. controls, FIG. 12a, inset], suggesting that no changes in post-synaptic NMDA receptor density or properties at this time point (data not shown). Synaptic glutamate elicited by 50 extracellular stimulations at 2, 5, 10, 20, 50 and 100 Hz before and after adding the astrocytic SLC1A2 specific inhibitor, DHK was measured. In neurons from control animals, DHK had no effect on single EPSCs or EPSCs elicited at low stimulation frequencies (<20 Hz). In contrast, stimulation frequencies >20 Hz resulted in increased NMDA currents (or reduced depression when normalized to the first stimulus, FIG. 12b-c, left), suggesting that astrocytic glutamate transporters efficiently reduce synaptic glutamate levels at high frequencies of neuronal activation. The same experiments were then repeated 24 h following cortical application of albumin (i.e. during epileptogenesis). In contrast to the control experiments, DHK had no effect on EPSC amplitude in treated slices (FIG. 13b-c, right), supporting reduced expression of the astrocytic transporter SLC1A2. Repetitive stimulation, however, resulted in a stronger depression of EPSC amplitude in treated slices as compared to controls.

Figures 12D, 12E:
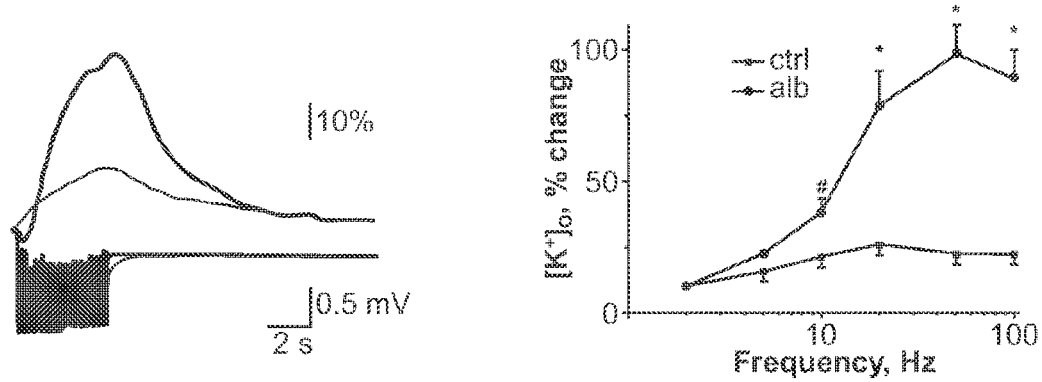

To study $K^+$ clearance from the extracellular space, K clearance was recorded from control and treated slices (24 h following treatment with albumin) by using ISMEs. Slower decay kinetics of $[K^+]_o$ in response to pressure application in BBB-treated animals has been reported (Ivens et al., 2007). Here, $[K]_o$ accumulation during neuronal activation at different frequencies of stimulation was tested. In slices from control animals, the increase in $[K^+]_o$ was limited to 25% of baseline levels (<3.75 mM) at all stimulation frequencies with the employed stimulation intensities and number of stimuli. In contrast, in treated slices $[K^+]_o$ accumulation was significantly higher at frequencies ≥10 Hz, reaching 6.7 mM (FIG. 12d-e).

Figure 13B:
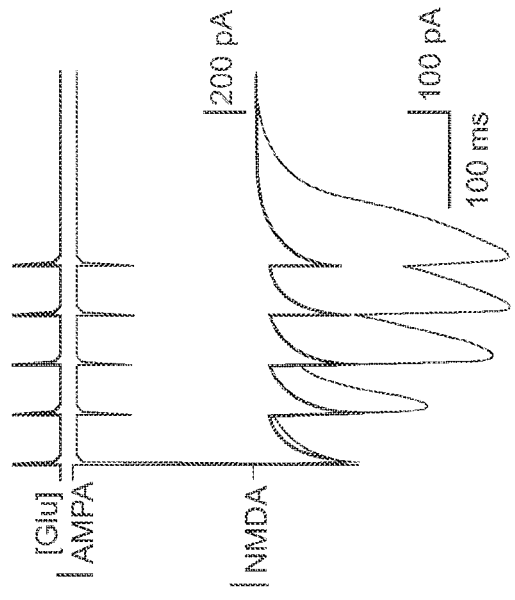
Figure 13A:
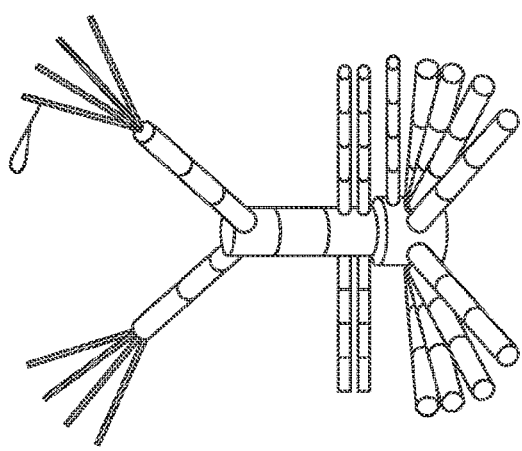
Figure 13D:
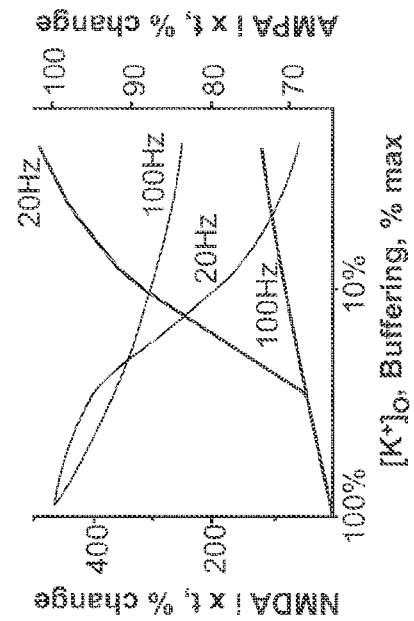
Figure 13C:
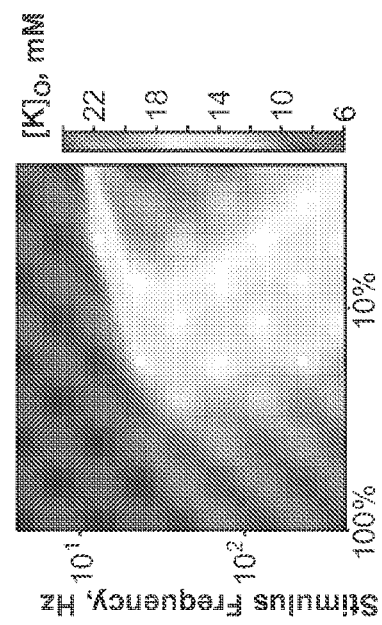
Figure 14A:
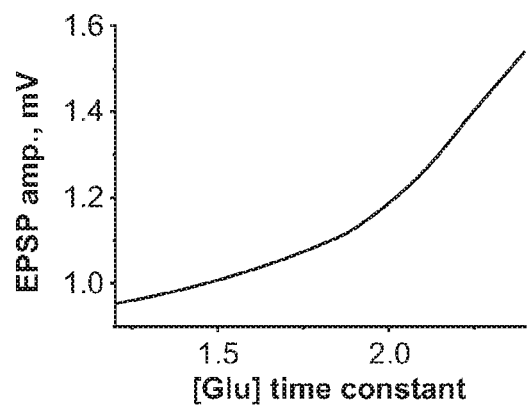
FIGS. 14*a-d* illustrate application of NEURON-based model to determine the effects of glutamate accumulation.
Figure 14B:
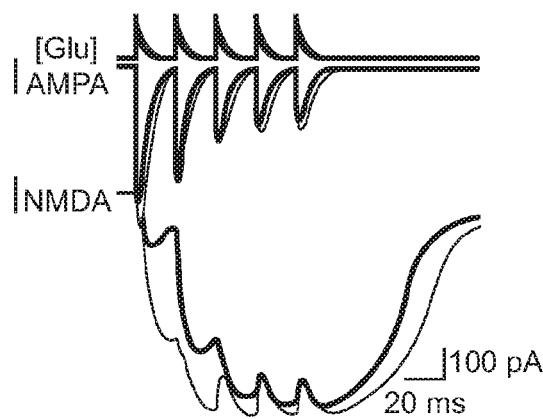
Figure 14C:
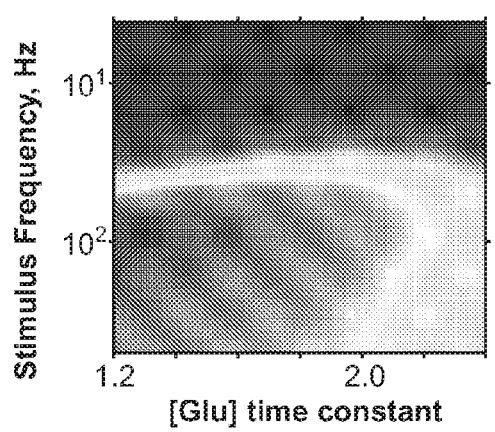
Figure 14D:
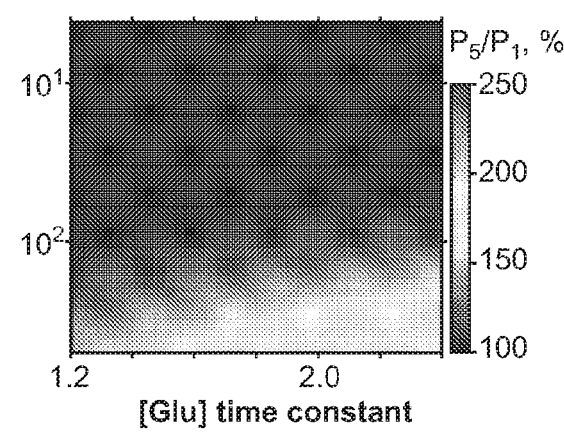

Modeling Reduced $K^+$ Clearance Results in Frequency-Dependent Facilitation of Excitatory Post-Synaptic Potentials To elucidate the possible contribution of astrocytic dysfunction to neuronal excitability, a NEURON-based model of a post-synaptic neuron and an astrocyte was developed. To evaluate the role of increased $[K^+]_o$ accumulation and glutamate accumulation, changes to excitatory synaptic currents in the post-synaptic neuron were examined (see Methods). Excitatory synaptic input was simulated by simultaneous application of glutamate at all 8 distal dendritic processes (FIG. 13a). The reduction in $K^+$ clearance was simulated by manipulating a $[K^+]_o$-regulated potassium removal mechanism ($I_{KIR}$), while keeping the diffusion component constant. In the absence of neuronal activity, reducing $K_{IR}$-mediated potassium clearance had no effect on resting $[K^+]_o$ and thus had a negligible effect on the rising phase and maximal amplitude of a single excitatory post-synaptic potential (EPSP) (FIG. 13b). Reducing potassium buffering and consequent increased $K^+$ accumulation during repetitive stimulation resulted in enhanced EPSP duration due to slower repolarization (due to a reduced driving force for $K^+$ and a slight increase in NMDA-mediated current, see below and FIG. 14b). During repetitive activation, the accumulation of $[K^+]_o$ near the dendritic compartment reached a maximum of 8.7 (and 16 mM) for reduction to 50% (and 10%) of astrocytic $[K^+]_o$ buffering capacity, respectively (FIG. 13c). $[K^+]_o$ accumulation during repetitive stimulation had a differential effect on AMPA- and NMDA-mediated currents: while the AMPA current showed frequency-dependent depression due to receptor desensitization, the NMDA component was strongly facilitated due to membrane depolarization (FIG. 14b). Reducing astrocytic potassium uptake from the extracellular space to 10% of control values resulted in an increase in total charge transfer mediated by the NMDA component of 44, 344 and 84% at 10, 20 and 100 Hz, respectively, while the AMPA charge transfer decreased by 5, 24, and 15%, respectively (FIG. 14d). Overall, there was a frequency-dependent increase in EPSP amplitude (FIG. 14e) associated with longer decay time (FIG. 13f). Repeated simulations with no NMDA conductance ($G_{NMDA}$=0, with concomitant increased AMPA conductance, to achieve similar depolarization for a single stimulus) resulted in a much smaller facilitation (compare FIGS. 13g and h).

Modeling Reduced Glutamate Clearance Results in Frequency-Dependent Depression of Excitatory Post-Synaptic Potentials The NEURON model and simulation paradigms described above were used to test the expected effect of reduced glutamate uptake. The reduction in glutamate uptake was simulated by slowing the transmitter's synaptic decay function. A twofold increase in the glutamate decay time constant resulted in a 48% increase in EPSP amplitude (from 25 to 37 mV) at a single post-synaptic dendrite and a 60% increase in the amplitude of the summated somatic EPSP (FIG. 14a). While for a single stimulation both AMPA and NMDA-components were increased, with repetitive activation, a marked decrease in the AMPA current (due to receptor desensitization, see Otis et al., 1996) and a strong facilitation of the NMDA current (due to post-synaptic depolarization, see Mayer et al., 1984 and FIG. 14b-c) were measured. Somatic EPSP facilitation (ratio of $5^{th}$ to $1^{st}$ EPSP amplitude, FIG. 15c) was maximal at 100 Hz with our initial conditions for glutamate clearance. Inhibiting glutamate clearance did not affect EPSP facilitation at low stimulation frequencies (<20 Hz) but reduced it at high stimulation frequencies (>80 Hz). The decreased facilitation was due to a reduced AMPA current through the desensitized receptors, thus keeping the membrane potential below the threshold for NMDA receptor activation. In simulations performed in the absence of NMDA conductance, EPSP facilitation was reduced at most stimulation frequencies, with only a small (<150%) residual facilitation measured at high stimulation frequencies (>100 Hz, FIG. 14d).

Modeling the Concerted Effect of Reduced Potassium and Glutamate Clearance

Figure 15A:
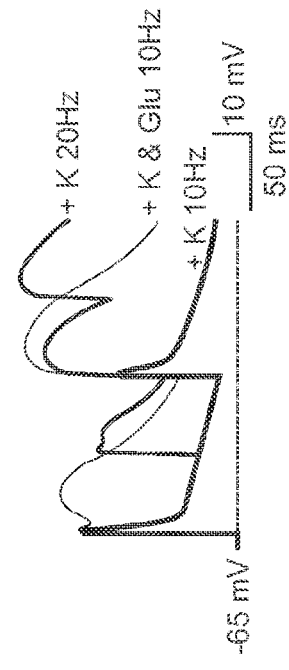
FIGS. 15*a-d* illustrate modelling effect of reduced potassium and glutamate clearance.
Figure 15C:
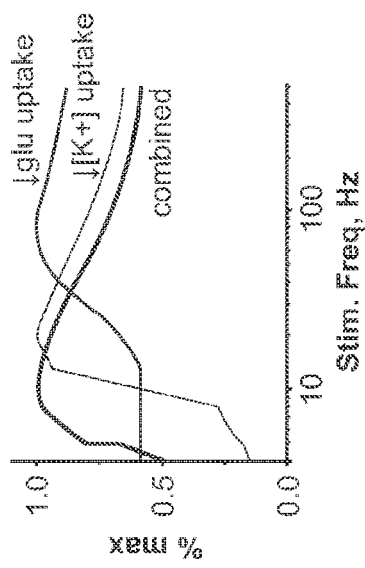
Figure 15B:
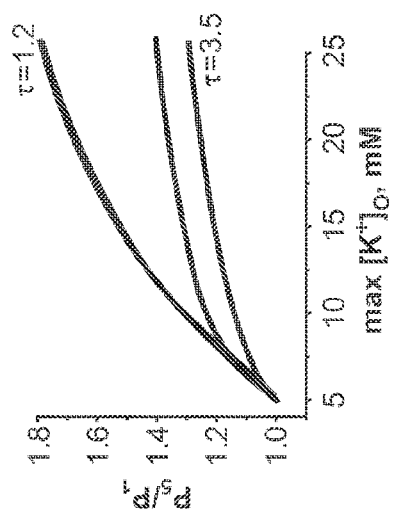
Figure 15D:
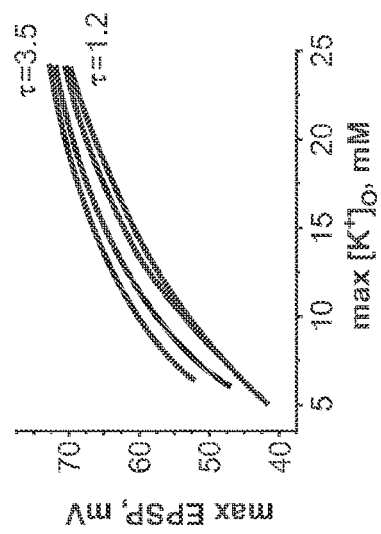

The simulations showed that while synaptic glutamate levels mainly affected the $1^{st}$ EPSP in the train, an activity-dependent increase in $[K^+]_o$ mainly enhanced EPSP facilitation in a frequency-dependent manner. Since the molecular data indicated a decrease in both potassium and glutamate buffering mechanisms, their joint effect on synaptic transmission was simulated. Decreasing the clearance of $[K^+]_o$ led to maximal EPSP facilitation when stimulating at 20 Hz, while a concurrent twofold reduction in glutamate uptake shifted the optimal frequency for maximal facilitation to 10 Hz (FIG. 15a). Concurrent reductions in glutamate and $[K^+]_o$ clearance led to increases in the duration of the $1^{st}$ EPSP, which in turn elicited increased and longer NMDA receptor activation per stimulus. The longer EPSPs allowed for a larger charge transfer with longer inter-stimulus intervals (i.e., reduced frequency. FIG. 15b) thus lowering the optimal stimulation frequency. To assess the sensitivity of the synaptic response during repetitive stimulation (at 20 Hz), several glutamate decay time constants and varying levels of $[K^+]_o$ uptake was used. We plotted the maximal EPSP amplitude as a function of $[K^+]_o$; FIG. 15c demonstrates that increasing synaptic glutamate led to small increases in the maximal EPSP amplitudes for all levels of $[K^+]_o$. However, synaptic facilitation was decreased with reduced glutamate uptake: thus, synaptic $[K^+]_o$ accumulation to 10 mM was associated with 40% EPSP facilitation (upon the $5^{th}$ stimulation) under baseline glutamate clearance, but with only 22% facilitation when glutamate decay time was doubled (FIG. 15d).

Electrophysiological Evidence for Frequency-Dependent Synaptic Facilitation During Epileptogenesis The simulation data presented above predicted maximal EPSP facilitation at 20 Hz when $[K^+]_o$ clearance is reduced and decreased facilitation (at 50-100 Hz) when the only change induced is glutamate accumulation in the synaptic cleft. Field potentials in response to stimulation at various frequencies in brain slices during "epileptogenesis" (exposure to albumin in sACSF) compared to controls (sACSF alone) were therefore measured. Comparison of the field potential amplitude and absolute integral during the first five stimuli revealed a significant reduction in both measures only under 100 Hz stimulation [amplitude: 1.13±0.12 vs. 0.46±0.03 mV, 1.44±0.36 vs. 0.47±0.09 mV and area: 2.4±0.2 vs. 0.9±0.02 V*s, 4.4*1.1 vs. 0.5±0.7 V*s, $1^{st}$ vs. $5^{th}$ stimulus, control (n=5) and treated (n=4), respectively, p<0.05]. Comparing field potential duration (measured at ⅓ maximal amplitude) for the $1^{st}$ vs. the $5^{th}$ stimulus among different frequencies did not reveal any changes in control slices. In contrast, in treated slices the field potential was significantly prolonged at 10 and 20 Hz (10 Hz: 7.5±0.4 vs. 9.4±5.5 ms, 6.5±0.7 vs. 13.1±2.6 ms, 20 Hz: 6.0±0.9 vs. 6.8±0.8 ms, 6.6±0.8 vs. 12.9±2.9 ms for $1^{st}$ vs. $5^{th}$ stimulus in control and treated, respectively, p<0.05. FIG. 16c). Interestingly, in the "treated" group, stimulation-induced frequency-dependent, long-lasting epileptiform discharges occurred most reliably during 10-Hz stimulation (4 of 4 slices, n=3 animals), and sometimes at 20 Hz (3 of 4 slices) and 5 Hz (2 of 4 slices), but never at higher frequencies (FIG. 16d). Epileptiform discharges were observed in one control slice without any apparent frequency dependence (5 to 50 Hz, 1 of 5 slices, n=3 animals, FIG. 16d).

Taken together, these experiments show that exposure to albumin in-vitro induces changes in neuronal excitability and that evoked network activity facilitates, and often turns into, robust epileptiform discharges upon repetitive stimulation. 10-20 Hz was found to be the most reliable frequency, as was also predicted by the $K^+$ recording data (FIG. 12d) and by the model shown above in the case of reduction in $[K^+]_o$ clearance with or without glutamate accumulation (see FIG. 13g).

FIGS. 10-16

FIG. 10. Transcriptional Changes in Astrocytes Following Exposure to Albumin or BBB Disruption.

(a) Sham-normalized expression levels of mRNA for genes preferentially expressed in astrocytes at 8, 24, and 48 h following treatment with the BBB disrupting agent DOC (D) or albumin (A). (b) Hierarchical cluster analysis comparing astrocytic gene expression for DOC-treated and albumin-treated cortices at 8, 24, and 48 h following treatment, and the contralateral, non-treated hemisphere (Ctrl Hemi.). (c) Average number of gene transcripts up- or down-regulated by more than 150% grouped by cell-type across all time points. (d) Sham normalized mRNA expression levels of genes coding for known astrocytic activation markers.

FIG. 11. Alterations in Astrocytic Potassium and Glutamate Regulating Genes.

(a) Sham-normalized mRNA expression levels for genes associated with K+ and glutamate homeostasis at 8, 24, and 48 h following in-vivo treatment with DOC (D) and albumin (A). (b) Sham-normalized mRNA expression levels for selected transcripts (see Results) obtained by real-time RT-PCR 24 h following DOC (grey bars) or albumin (black bars) treatments. (c) Astrocyte enriched cell cultures immunostained for GFAP (red) or NeuN (green). Nuclei visualized with DAPI staining (blue). The graph shows mRNA expression levels in albumin-exposed cultures compared to controls. (d) same as c, for neuron enriched cultures. Abbr.: SLC1a2-GLT-1, SLC1a3-GLAST, Gja1, Gjn2, Gjb6, -connexins 43, 26, 30 respectively, Kenj3-KIR3.1

FIG. 12. Electrophysiological Evidence for Reduced Glutamate and Potassium Buffering During Epileptogenesis.

(a) Single NMDA-mediated EPSCs in control slices and 24 h following albumin treatment in vivo in ACSF (gray) and 10 min following DHK (black). Inset shows mean EPSC amplitude in ACSF. (b) NMDA-mediated EPSCs during train stimulation at 50 Hz in control animals and treated animals. (c) Mean evoked NMDA-mediated EPSC at different stimulation frequencies. (d) [K+]o levels in control and treated slices during 20 Hz stimulation (e) Mean [K+]o levels during extracellular stimulation at 2-100 Hz (right). #, p<0.03, *, p<0.001 (n=6 albumin-treated cells, 5 animals, n=9 control cells, 7 animals).

FIG. 13. Application of NEURON-Based Model to Determine the Effects or [K+]o Accumulation.

(a) Schematic diagram of the modeled layer 2/3 pyramidal neuron containing 74 compartments with 8 synapses (with AMPA and NMDA currents), one at each distal dendrite. (b) Increasing glutamate levels at each of the 8 synapses (top trace representing kinetics of synaptic glutamate level) elicits AMPA-mediated (middle trace) and NMDA-mediated (bottom trace) currents under control conditions (black) and under reduced astrocytic potassium clearance (under a 10-fold decrease of astrocytic K+ clearance, blue trace). (c) Maximal K+ concentrations recorded in the vicinity of a distal dendritic compartment during repetitive stimulation as a function of [K+]o clearance and stimulation frequency. (d) Percent change of total charge transfer by NMDA (black) and AMPA (blue) channels during stimulation at 20 and 100 Hz. (e). Somatic EPSPs under control conditions (black) and under reduced astrocytic potassium clearance (10-fold reduction of control levels, blue trace). (f) 5th EPSP (elicited by stimulation at 4, 20, and 100 Hz) decay time constant at different levels of astrocytic potassium clearance rates. (g) Ratio of 5th to 1st EPSP amplitude (P5/P1) at stimulation frequencies of 4-500 Hz at different levels of astrocytic potassium clearance rates. (h) Same as in (g) with GNMDA=0.

FIG. 14. Application of NEURON-Based Model to Determine the Effects of Glutamate Accumulation.

(a) Somatic EPSP amplitudes for different glutamate time constants. (h) Simultaneous glutamate "application" (kinetics represented in the upper trace) at each of the 8 synapses elicits AMPA-mediated (middle) and NMDA-mediated (bottom) currents under control conditions (black) and a twofold increase in glutamate decay time constant (blue). (c) Ratio of 5th to 1st EPSP amplitude (P5/P1) at different stimulation frequencies and varying glutamate decay time constants (values related to control). (d) Same as in (c) with GNMDA=0.

FIG. 15. Modeling the Concerted Effect of Reduced Potassium and Glutamate Clearance.

(a) EPSP facilitation (relative to maximal value) for a 10-fold decrease in [K+]o clearance (black), a twofold slowing of glutamate decay time constant (red) and for down regulation of both uptake mechanisms (blue) as a function of stimulation frequency. (b) EPSP traces for 10- and 20-Hz trains under a 10-fold decrease in astrocytic K+ clearance (gray and blue traces, respectively) and with both uptake mechanisms down regulated (at 10 Hz, black). Dashed line marks resting potential. (c) Maximal EPSP amplitude elicited by a train of five stimuli as a function of maximal [K+]o for different glutamate uptake decay time constants (for 1.2, 2.2, 3.2 and 3.5 ms). (d) EPSPs facilitation [ratio of 5th to 1st EPSP amplitude (P5/P1)] for 20 Hz stimulation for different glutamate decay time constants (as in c).

FIG. 16. Recording In Vitro Shows Frequency-Dependent Increased Neuronal Excitability and Hyper-Synchronous Network Activity During Albumin-Mediated Epileptogenesis.

(a, b) Neocortical field potential recordings of brain slices during stimulation trains of 50 pulses at 2, 10 and 100 Hz. Field responses were facilitated in the albumin-treated slices, observed as increased duration of the population spikes (see inset in a, b). (c) Comparison of the average field potential duration (at ⅓ maximal amplitude) for the 5th to the 1st evoked response reveals maximal facilitation at 10 Hz. (d) Percentage of slices showing prolonged, paroxysmal discharges.

REFERENCES

Abbott, N.J., Rönnbäck, L. & Hansson, E. (2006) Astrocyte-endothelial interactions at the blood-brain barrier. Nature Neurosci. Rev. 7:41-53.

Araque A, Carmignoto G, Haydon P G (2001) Dynamic signaling between astrocytes and neurons. Annual Review of Physiology 63:795-813.

Arnth-Jensen N, Jabaudon D, Scanziani M (2002) Cooperation between independent hippocampal synapses is controlled by glutamate uptake. Nat Neurosci 5:325-331.

Arriza J L, Fairman W A, Wadiche J I, Murdoch G H, Kavanaugh M P, Amara S G (1994) Functional comparisons of three glutamate transporter subtypes cloned from human motor cortex. J Neurosci 14: 5559-5569.

Barres B A, Chun L L, Corey D P (1990) Ion channels in vertebrate glia. Annu Rev Neurosci 13:441-474.

Bergles D E, Jahr C E (1998) Glial contribution to glutamate uptake at Schaffer collateral-commissural synapses in the hippocampus. J Neurosci 18:7709-7716.

Bordey A, Lyons S A, Hablitz J J, Sontheitner H (2001) Electrophysiological characteristics of reactive astrocytes in experimental cortical dysplasia. J Neurophysiol 85:1719-1731.

Bordey A. Sontheimer H (1998) Properties of human glial cells associated with epileptic seizure foci. Epilepsy Res 32:286-303.

Butt A M, Kalsi A (2006) Inwardly rectifying potassium channels (Kir) in central nervous system glia: a special role for Kir4.1 in glial functions. J Cell Mol Med 10:33-44.

Cahoy J D, Emery B, Kaushal A. Foo L C, Zamanian J L. Christopherson K S, Xing Y, Lubischer J L. Krieg P A, Krupenko S A, Thompson W J, Barres B A (2008) A transcriptome database for astrocytes, neurons, and oligodendrocytes: A new resource for understanding brain development and function. J Neurosci 28:264-278.

Chaudhry F A, Lehre K P, Lookeren Campagne Mv, Ottersen O P, Danbolt N C, Storm-Mathisen J (1995) Glutamate transporters in glial plasma membranes: Highly differentiated localizations revealed by quantitative ultrastructural immunocytochemistry. Neuron 15:711-720.

Chen K C, Nicholson C (2000) Spatial buffering of potassium ions in brain extracellular space. Biophys J 78:2776-2797.

Ciani S, Krasne S, Miyazaki S, Hagiwara S. (1978) A model for anomalous rectification: electrochemical-potential-dependent gating of membrane channels. J Membr Biol 44:103-34.

D'Ambrosio R, Maris D O, Grady M S, Winn H R, Janigro D (1999) Impaired K(+) homeostasis and altered electrophysiological properties of post-traumatic hippocampal glia. J Neurosci 19:8152-8162.

Derouiche A, Frotscher M (1991) Astroglial processes around identified glutamatergic synapses contain glutamine synthetase: evidence for transmitter degradation. Brain Research 552:346-350.

Diamond J S (2005) Deriving the glutamate clearance time course from transporter currents in CA1 hippocampal astrocytes: Transmitter uptake gets faster during development. J Neurosci 25:2906-2916.

Diamond J S, Jahr C E: (2000) Synaptically released glutamate does not overwhelm transporters on hippocampal astrocytes during high-frequency stimulation. Journal of Neurophysiology 83:2835-2843.

Ding S, Fellin T, Zhu Y, Lee S Y, Auberson Y P, Meaney D F, Coulter D A, Carmignoto G, Haydon P G (20(71) Enhanced astrocytic Ca2+ signals contribute to neuronal excitotoxicity after status epilepticus. J Neurosci 27:10674-10684.

Djukic B. Casper K B, Philpot B D, Chin L S, McCarthy K D (2007) Conditional knock-out of Kir4.1 leads to glial membrane depolarization, inhibition of potassium and glutamate uptake, and enhanced short-term synaptic potentiation. journal of neuroscience 27:11354-11365.

Egelman Dm, Montague P R (1999) Calcium dynamics in the extracellular space of mammalian neural tissue. Biophys J 76:1856-1867.

Eid T, Williamson A, Lee T S, Petroff O A, de Lanerolle N C (2008) Glutamate and astrocytcs—key players in human mesial temporal lobe epilepsy? Epilepsia 49 Suppl 2:42-52.

Fertziger A P, Ranck J B (1970) Potassium accumulation in interstitial space during epileptiform seizures. Experimental Neurology 26:571-585.

Gabriel S, Eilers A, Kivi A, Kovacs R, Schulze K, Lehmann T N, Heinemann U (1998) Effects of barium on stimulus induced changes in extracellular potassium concentration in area CA1 of hippocampal slices from normal and pilocarpine-treated epileptic rats. Neurosci Lett 242:9-12.

Geursen A, Grigor M R (1987) Serum albumin secretion in rat milk. J Physiol 391:419-427.

Gronau I, Moran S (2007) Optimal implementations of UPGMA and other common clustering algorithms. Information Processing Letters 104:205-210.

Heinemann U, Gabriel S, Schuchmann S, Eder C (1999) Contribution of astrocytes to seizure activity. Adv Neurol 79:583-590.

Heinemann U, Schaible H G, Schmidt R F (1990) Changes in extracellular potassium concentration in cat spinal cord in response to innocuous and noxious stimulation of legs with healthy and inflamed knee joints. Exp Brain Res 79:283-292.

Herman S T (2002) Epilepsy after brain insult: Targeting epileptogenesis. Neurology 59:21-6.

Hestrin S, Sah P, Nicoll R A (1990) Mechanisms generating the time course of dual component excitatory synaptic currents recorded in hippocampal slices. Neuron 5:247-253.

Hibino H, Fujita A. Iwai K, Yamada M, Kurachi Y (2004) Differential assembly of inwardly rectifying K+ channel subunits. Kir4.1 and Kir5.1, in brain astrocytes. J Biol Chem 279:44065-44073.

Hickenbottom S L, Grotta J (1998) Neuroprotective therapy. Semin Neurol 18:485-492.

Higashi K, Fujita A, Inanobe A, Tanemoto M, Doi K, Kubo T, Kurachi Y (2001) An inwardly rectifying K(+) channel, Kir4.1, expressed in astrocytes surrounds synapses and blood vessels in brain. Am J Physiol Cell Physiol 281:C922-C931.

Hines M L, Carnevale NT (1997) The NEURON Simulation Environment. Neural Comp 9:1179-1209.

Hinterkeuser S, Schroder W, Hager G, Seifert G, Blumcke I, Elger C E, Schramm J, Steinhauser C (2000) Astrocytes in the hippocampus of patients with temporal lobe epilepsy display changes in potassium conductances. Eur J Neurosci 12:2087-2096.

Iscrhot, C. Gebhardt, D. Schmitz and U. Heinemann (2004) Glutamate transporters and metabotropic receptors regulate excitatory neurotransmission in the medial entorhinal cortex of the rat. Brain Res 1027:151-160.

Ivens S, Kaufer D, Flores L P, Bechmann I, Zumsteg D, Tomkins O, Seiffert E. Heinemann U, Friedman A (2007) TGF-beta receptor-mediated albumin uptake into astrocytes is involved in neocortical epileptogenesis. Brain 130.535-547.

Jansen L A, Uhlmann E J, Crino P B, Gutmann D H, Wong M (2005) Epileptogenesis and reduced inward rectifier potassium current in tuberous sclerosis complex-1-deficient astrocytes. Epilepsia 46:1871-1880.

Jauch R, Windmuller O, Lehmann T N, Heinemann U, Gabriel S (2002) Effects of barium, furosemide, ouabaine and 4,4'-diisothiocyanatostilbene-2,2'-disulfonic acid (DIDS) on ionophoretically-induced changes in extracellular potassium concentration in hippocampal slices from rats and from patients with epilepsy. Brain Res 925:18-27.

Kager H, Wadman W J, Somjen G G (2000) Simulated seizures and spreading depression in a neuron model incorporating interstitial space and ion concentrations. J Neurophysiol 84:495-512.

Kampa B M, Clements J, Jonas P, Stuart G J (2004) Kinetics of Mg2+ unblock of NMDA receptors: Implications for spike-timing dependent synaptic plasticity. J Physiol 556:337-345.

Kaufer D, Ogle W O, Pincus Z S, Clark K L, Nicholas A C, Dinkel K M, Dumas T C, Ferguson D, Lee A L, Winters M A, Sapolsky R M (2004) Restructuring the neuronal stress response with anti-glucocorticoid gene delivery. Nat Neurosci 7:947-953.

Kivi A, Lehmann T N, Kovacs R, Filers A, Jauch R, Meencke H J, von Deimling A, Heinemann U, Gabriel S (2000) Effects of barium on stimulus-induced rises of [K+]o in human epileptic non-sclerotic and sclerotic hippocampal area CA1. Eur J Neurosci 12:2039-2048.

Koller H, Schroeter M, Jander S, Stoll G, Siebler M (2000) Time course of inwardly rectifying K(+) current reduction in glial cells surrounding ischemic brain lesions. Brain Res 872:194-198.

Kuffler S W, Potter D D (1964) Glia in the leech central nervous system: Physiological properties and neuron-glia relationship. J Neurophysiol 27:290-320.

Lehre K P. Danbolt N C (1998) The number of glutamate transporter subtype molecules at glutamatergic synapses: Chemical and stereological quantification in young adult rat brain. J Neurosci 18:8751-8757.

Lester R A J, Clements J D, Westbrook G L, Jahr C E (1990) Channel kinetics determine the time course of NMDA receptor-mediated synaptic currents. Nature 346:565-567.

Li H, Prince D A (2002) Synaptic activity in chronically injured, epileptogenic sensory-motor neocortex. J Neurophysiol 88:2-12.

Lux H D, Neher E. The equilibration time course of [K+]o in cat cortex. Exp Brain Res 1973; 17: 190-205.

Marchi N, Angelov L., Masaryk T, Fazio V. Granata T, Hernandez N, Hallene K, Diglaw T, Franic L, Najm I, Janigro D (2007) Seizure-promoting effect of blood-brain barrier disruption. Epilepsia 48:732-742.

Mayer M L, Westbrook G L, Guthrie P B (1984) Voltage-dependent block by Mg2+ of NMDA responses in spinal cord neurones. Nature 309:261-263.

Myme C I, Sugino K, Turrigiano G G, Nelson S B (2003) The NMDA-to-AMPA ratio at synapses onto layer 2/3 pyramidal neurons is conserved across prefrontal and visual cortices. J Neurophysiol 90:771-779.

Neuwelt E A (2004) Mechanisms of disease: the blood-brain barrier. Neurosurgery 54:131-140.

Newman E A, Frambach D A, Odette L L (1984) Control of extracellular potassium levels by retinal glial cell K+ siphoning. Science 225:1174-1175.

Newman E A (1993) Inward-rectifying potassium channels in retinal glial (Muller) cells. J Neurosci 13:3333-3345.

Oliet S H R, Piet R, Poulain D A (2001) Control of glutamate clearance and synaptic efficacy by glial coverage of neurons. Science 292:923-926.

Otis T, Zhang S, Trussell L O (1996) Direct measurement of AMPA receptor desensitization induced by glutamatergic synaptic transmission. J Neurosci 16:7496-7504.

Pasler D, Gabriel S, Heinemann U (2007) Two-pore-domain potassium channels contribute to neuronal potassium release and glial potassium buffering in the rat hippocampus. Brain Res 1173:14-26.

Pavlovsky L, Browne R O, Friedman A (2003) Pyridostigmine enhances glutamatergic transmission in hippocampal CA1 neurons. Experimental Neurology 179:181-187.

Pfaffl M W, Horgan G W, Demptle L (2002) Relative expression software tool (REST) for group-wise comparison and statistical analysis of relative expression results in real-time PCR. Nucleic Acids Res 30:e36.

Proper E A, Hoogland G. Kappen S M, Jansen G H, Rensen M G A, Schrama L H, van Veelen C W M, van Rijen P C, van Nieuwenhuizen O, Gispen W H, de Graan P N E (2002) Distribution of glutamate transporters in the hippocampus of patients with pharmaco-resistant temporal lobe epilepsy. Brain 125:32-43.

Rebhan M. Chalifa-Caspi V, Prilusky J, Lancet D (1998) GeneCards: A novel functional genomics compendium with automated data mining and query reformulation support. Bioinformatics 14:656-664.

Ridet J L, Malhotra S K, Privat A, Gage F H (1997) Reactive astrocytes: Cellular and molecular cues to biological function. Trends Neurosci 20:570-577.

Rothstein J D, Martin L, Levey A I, Dykes-Hoberg M, Jin L, Wu D, Nash N, Kuncl R W (1994) Localization of neuronal and glial glutamate transporters. Neuron 13:713-725.

Rothstein J D, Martin L J, Kuncl R W (1992) Decreased glutamate transport by the brain and spinal cord in amyotrophic lateral sclerosis. N Engl J Med 326:1464-1468.

Saftenku E E (2005) Modeling of slow glutamate diffusion and AMPA receptor activation in the cerebellar glomerulus. Journal of Theoretical Biology 234:363-382.

Sakai K, Shimizu H, Koike T, Furuya S, Watanabe M (2003) Neutral amino acid transporter ASCT1 is preferentially expressed in L-Ser-synthetic/storing glial cells in the mouse brain with transient expression in developing capillaries. J Neurosci 23:550-560.

Sakmann B, Trube G (1984) Conductance properties of single inwardly rectifying potassium channels in ventricular cells from guinea-pig heart. J Physiol 347:641-657.

Sarantis M, Ballerini L, Miller B, Silver R A. Edwards M, Attwell D (1993) Glutamate uptake from the synaptic cleft does not shape the decay of the non-NMDA component of the synaptic current. Neuron 11:541-549.

Savtchenko L P, Antropov S N, Korogod S M (2000) Effect of voltage drop within the synaptic cleft on the current and voltage generated at a single synapse. Biophys J 78:1119-1125.

Scanziani M, Salin P A, Vogt K E, Malenka R C, Nicoll R A (1997) Use-dependent increases in glutamate concentration activate presynaptic metabotropic glutamate receptors. Nature 385:630-634.

Schroder W, Hager G, Kouprijanova E. Weber M. Schmitt A B, Seifert G, Steinhauser C (1999) Lesion-induced changes of electrophysiological properties in astrocytes of the rat dentate gyrus. Glia 28:166-174.

Schroder W, Hinterkeuser S, Seifert G, Schramm J, Jabs R, Wilkin G P, Steinhauser C (2000) Functional and molecular properties of human astrocytes in acute hippocampal slices obtained from patients with temporal lobe epilepsy. Epilepsia 41:S181-S184.

Schwarcz R (2008) Early glial dysfunction in epilepsy. Epilepsia 49 Suppl 2:1-2.

Seifert G, Schilling K, Christian Steinhauser (2006) Astrocyte dysfunction in neurological disorders: a molecular perspective. Nature Reviews Neuroscience 7:194-206.

Seiffert E, Dreier J P, Ivens S, Bechnann I, Tonkins O, Heinemann U, Friedman A (2004) Lasting blood-brain barrier disruption induces epileptic focus in the rat somatosensory cortex. J Neurosci 24:7829-7836.

Shao L R, Dudek F E (2004) Increased excitatory synaptic activity and local connectivity of hippocampal CA1 pyramidal cells in rats with kainate-induced epilepsy. J Neurophysiol 92:1366-1373.

Somjen G G, Kager 11. Wadman W J (2008) Computer simulations of neuron-glia interactions mediated by ion flux. J Comput Neurosci.

Sonkusare S K, Kaul C L Ramarao P (2005) Dementia of Alzheimer's disease and other neurodegenerative disorders—memantine, a new hope. Pharmacol Res 51:1-17.

Su Z Z, Leszczyniecka M, Kang D C, Sarkar D, Chao W, Volsky D J, Fisher P B (2003) Insights into glutamate transport regulation in human astrocytes: Cloning of the promoter for excitatory amino acid transporter 2 (EAAT2). Proc Natl Acad Sci USA 100:1955-1960.

Szatkowski M, Barbour B, Attwell D (1990) Non-vesicular release of glutamate from glial cells by reversed electrogenic glutamate uptake Nature 348:443-446.

Takayasu Y, Iino M. Ozawa S (2004) Roles of glutamate transporters in shaping excitatory synaptic currents in cerebellar Purkinje cells. European Journal of Neuroscience 19:1285-1295.

Tanaka K, Watase K, Manahe T, Yamada K. Watanabe M, Takahashi K, Iwama I I, Nishikawa T, Ichihara N, Kikuchi T, Okuyama S. Kawashima N, Hori S, Takimoto M, Wada K (1997) Epilepsy and exacerbation of brain injury in mice lacking the glutamate transporter GLT-1. Science 276:1699-1702.

Tessler S, Danbolt N C, Faull R L, Storm-Mathisen J, Emson P C (1999) Expression of the glutamate transporters in human temporal lobe epilepsy. Neuroscience 88:1083-1091.

Tian G F, Azmi H, Takano T, Xu Q W, Peng W G, Lin J. Oberheim N, Lou N H, Wang X H, Zielke H R, Kang J, Nedergaard M (2005) An astrocytic basis of epilepsy. Nature Medicine 11:973-981.

Tomkins O, Friedman O, Ivens S, Reiffurth C, Major S, Dreier J P, Heinemann U. Friedman A (2007) Blood-brain barrier disruption results in delayed functional and structural alterations in the rat neocortex. Neurobiol Dis 25:367-377.

Tomkins O, Kaufer D, Korn A. Shelef I, Golan H. Reichenthal E, Soreq H, Friedman A (2(001) Frequent blood-brain barrier disruption in the human cerebral cortex. Cell Mol Neurobiol 21:675-691.

Traub R D, Buhl E H, Gloveli T, Whittington M A (2003) Fast rhythmic bursting can be induced in layer 2/3 cortical neurons by enhancing persistent Na+ conductance or by blocking BK channels. Journal of Neurophysiology 89:909-921.

Turecek R, Trussell L O (2000) Control of synaptic depression by glutamate transporters. J Neurosci 20:2054-2063.

van der Hel W S, Notenboom R G E, Bos I W M, van Rijen P C, van Veelen C W M, de Graan P N E (2005) Reduced glutamine synthetase in hippocampal areas with neuron loss in temporal lobe epilepsy. Neurology 64:326-333.

van Vlict E A, da Costa A S, Redeker S, van S R, Aronica E, Gorter J A (2007) Blood-brain barrier leakage may lead to progression of temporal lobe epilepsy. Brain 130:521-534.

Vives V, Alonso G, Solal A C, Joubert D, Legraverend C (2003) Visualization of S100B-positive neurons and glia in the central nervous system of EGFP transgenic mice. J Comp Neurol 457:404-419.

Wallraff A, Kohling R, Heinemann U, Theis M, Willecke K, Steinhauser C (2006) The impact of astrocytic gap junctional coupling on potassium buffering in the hippocampus. J Neurosci 26:5438-5447.

Wetherington J. Serrano G, Dingledine R. (2008) Astrocytes in the epileptic brain. Neuron. 58:168-178. Zhao S, Fernald R D (2005) Comprehensive algorithm for quantitative real-time polymerase chain reaction. J Comput Biol 12:1047-1064.

Zlokovic B V (2008) The blood-brain barrier in health and chronic neurodegenerative disorders. Neuron 57:178-201.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating cognitive decline in an individual, the method comprising administering to the individual an effective amount of a transforming growth factor-beta (TGF-β) pathway blocker that specifically inhibits kinase activity of TGF-βI receptor, wherein the blocker is not an interfering nucleic acid.

2. The method of claim 1, wherein the cognitive decline is due to traumatic brain injury.

3. The method of claim 1, wherein said administering is effective to increase cognitive function in the individual by at least about 10%, compared to the cognitive function in the individual in the absence of treatment with the TGF-β pathway blocker.

4. The method of claim 1, wherein said administering is effective to increase cognitive function in the individual by at least 2-fold, compared to the cognitive function in the individual in the absence of treatment with the TGF-β pathway blocker.

5. The method of claim 1, wherein a single TGF-β pathway blocker is administered in monotherapy.

6. The method of claim 1, wherein a single TGF-β pathway blocker is administered in combination therapy with at least one additional therapeutic agent other than a TGF-β pathway blocker.

7. The method of claim 1, wherein the TGF-β pathway blocker is administered via injection.

8. The method of claim 1, wherein the TGF-β pathway blocker is administered orally.

9. The method of claim 1, wherein the TGF-β pathway blocker is administered intracranially.

10. The method of claim 1, wherein the TGF-β pathway blocker is administered together with an agent that facilitates crossing the blood-brain barrier.

11. The method of claim 1, wherein said administering is discontinuous.

12. The method of claim 1, wherein the TGF-β pathway blocker is administered:
 a) for a first period of time and at a first dosing frequency; and
 b) for a second period of time at a second dosing frequency.

13. The method of claim 12, wherein said administering is suspended for a period of time between the first period of time and the second period of time.

14. The method of claim 13, wherein the period of time the TGF-β pathway blocker is suspended ranges from 1 week to 6 months, from 1 week to 2 weeks, from 2 weeks to 4 weeks, from one month to 2 months, from 2 months to 4 months, or from 4 months to 6 months, or longer.

15. The method of claim 12, wherein the first period of time is the same as the second period of time.

16. The method of claim 12, wherein the first period of time is different than the second period of time.

* * * * *

UNITED STATES PATENT AND TRADEMARK OFFICE
CERTIFICATE OF CORRECTION

| | |
|---|---|
| PATENT NO. | : 10,668,049 B2 |
| APPLICATION NO. | : 15/258862 |
| DATED | : June 2, 2020 |
| INVENTOR(S) | : Daniela Kaufer et al. |

It is certified that error appears in the above-identified patent and that said Letters Patent is hereby corrected as shown below:

In the Specification

At Column 1, Line 59, "qRT-CR gene" should read --qRT-PCR gene--

At Column 4, Line 32, "antyotrophic" should read --amyotrophic--

At Column 6, Line 15, "(H-imidazol-4-yl)methyl]-3-phenlylpropionamide and" should read --(1H-imidazol-4-yl)methyl]-3-phenlylpropionamide and--

At Column 10, Line 4, "ribotnucleases" should read --ribonucleases--

At Column 11, Line 4, "IIoogsteen" should read --Hoogsteen--

At Column 16, Lines 52-53, "carboxym-ethylethylycellulose" should read --carboxymethylethylcellulose--

At Column 20, Line 2, "mute" should read --route--

At Column 21, Line 33, "tour" should read --four--

At Column 22, Line 14, "mutes" should read --routes--

At Column 22, Line 30, "mutes" should read --routes--

At Column 23, Line 65, "harrier" should read --barrier--

At Column 25, Line 34, "L-penicillanine" should read --L-penicillamine--

At Column 25, Line 37, "pholino-sydnoninine" should read --pholino-sydnonimine--

Signed and Sealed this
Second Day of March, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,668,049 B2

At Column 25, Line 38, "pholino-sydnoninmine" should read --pholino-sydnonimine--

At Column 26, Line 10, "Topiraniate" should read --Topiramate--

At Column 27, Line 12, "as" should read --aa--

At Column 29, Line 63, "01" should read --β1--

At Column 30, Line 7, "hand" should read --band--

At Column 31, Line 34, "hinds" should read --binds--

At Column 37, Line 66, "astrocytcs" should read --astrocytes--

At Column 38, Line 8, "scrum" should read --serum--

At Column 39, Line 23, "Electroplysiological" should read --Electrophysiological--

At Column 39, Line 48, "conical" should read --cortical--

At Column 41, Line 44, "lime" should read --time--

At Column 42, Line 4, "(Kenj10), but not neuronal (e.g. Kenj2 or Kene1,)" should read --(Kcnj10), but not neuronal (e.g. Kcnj2 or Kcnc1,)--

At Column 46, Line 3, "Kenj3" should read --Kcjn3--

At Column 46, Line 18, "or" should read --of--

At Column 47, Line 38, "Sontheitner" should read --Sontheimer--

At Column 48, Line 32, "astrocytcs" should read --astrocytes--

At Column 49, Line 46, "Filers" should read --Eilers--

At Column 50, Line 36, "Demptle" should read --Dempfle--

At Column 51, Line 29, "Bechnann I, Tonkins" should read --Bechmann I, Tomkins--

At Column 51, Lines 54, "Manahe" should read --Manabe--

At Column 51, Line 53, "I, Nishikawa" should read --H, Nishikawa--